(12) United States Patent
Pimenta et al.

(10) Patent No.: US 7,905,840 B2
(45) Date of Patent: Mar. 15, 2011

(54) SURGICAL ACCESS SYSTEM AND RELATED METHODS

(75) Inventors: Luiz Pimenta, Sao Paulo (BR); Patrick Miles, San Diego, CA (US); Scot Martinelli, San Diego, CA (US); Eric Finley, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1803 days.

(21) Appl. No.: 10/967,668

(22) Filed: Oct. 18, 2004

(65) Prior Publication Data

US 2005/0149035 A1 Jul. 7, 2005

Related U.S. Application Data

(60) Provisional application No. 60/512,594, filed on Oct. 17, 2003.

(51) Int. Cl.
*A61B 5/05* (2006.01)
(52) U.S. Cl. .................................................. 600/554
(58) Field of Classification Search .................. 600/545, 600/546, 547, 554, 210, 221
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |

(Continued)

FOREIGN PATENT DOCUMENTS

DE 299 08 259 7/1999

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Max Hindenburg
*Assistant Examiner* — Fangemonique Smith
(74) *Attorney, Agent, or Firm* — Jonathan Spangler; Rory Schermerhorn; Fish & Richardson P.C.

(57) ABSTRACT

A surgical access system including a tissue distraction assembly and a tissue retraction assembly, both of which may be equipped with one or more electrodes for use in detecting the existence of (and optionally the distance and/or direction to) neural structures before, during, and after the establishment of an operative corridor to a surgical target site. Some embodiments of the surgical access system may be particularly suited for establishing an operative corridor to a surgical target site in the spine. Such an operative corridor may be established through the retroperitoneal space and the psoas muscle during a direct lateral, retroperitoneal approach to the spine.

30 Claims, 50 Drawing Sheets

U.S. PATENT DOCUMENTS

| | | |
|---|---|---|
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,611,597 A | 9/1986 | Kraus |
| 4,633,889 A | 1/1987 | Talalla |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,913,134 A | 4/1990 | Luque |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,171,279 A | 12/1992 | Mathews |
| 5,195,541 A | 3/1993 | Obenchain |
| 5,196,015 A | 3/1993 | Neubardt |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,450,845 A | 9/1995 | Axelgaard |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,509,893 A | 4/1996 | Pracas |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,571,149 A | 11/1996 | Liss et al. |
| 5,579,781 A | 12/1996 | Cooke |
| 5,593,429 A | 1/1997 | Ruff |
| 5,599,279 A | 2/1997 | Slotman et al. |
| 5,630,813 A | 5/1997 | Kieturakis |
| 5,667,508 A | 9/1997 | Errico et al. |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,792,044 A | 8/1998 | Foley et al. |
| 5,797,854 A | 8/1998 | Hedgecock |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,891,147 A * | 4/1999 | Moskovitz et al. ............ 606/79 |
| 5,902,231 A | 5/1999 | Foley et al. |
| 5,928,139 A | 7/1999 | Koros |
| 5,928,158 A | 7/1999 | Aristides |
| 5,935,131 A | 8/1999 | Bonutti et al. |
| 5,938,688 A | 8/1999 | Schiff |
| 5,944,658 A | 8/1999 | Koros et al. |
| 5,976,094 A | 11/1999 | Gozani et al. |
| 6,004,262 A | 12/1999 | Putz et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,120,503 A | 9/2000 | Michelson |
| 6,126,660 A | 10/2000 | Dietz |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,146,335 A | 11/2000 | Gozani |
| 6,152,871 A | 11/2000 | Foley et al. |
| 6,161,047 A | 12/2000 | King et al. |
| 6,181,961 B1 | 1/2001 | Prass |
| 6,206,826 B1 | 3/2001 | Mathews et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,308,712 B1 * | 10/2001 | Shaw ............................ 128/869 |
| 6,312,392 B1 | 11/2001 | Herzon |
| 6,325,764 B1 | 12/2001 | Griffith et al. |
| 6,334,068 B1 | 12/2001 | Hacker |
| 6,425,859 B1 | 7/2002 | Foley et al. |
| 6,425,901 B1 | 7/2002 | Zhu et al. |
| 6,451,015 B1 | 9/2002 | Rittman, III et al. |
| 6,466,817 B1 | 10/2002 | Kaula et al. |
| 6,468,205 B1 * | 10/2002 | Mollenauer et al. .......... 600/201 |
| 6,468,207 B1 | 10/2002 | Fowler, Jr. |
| 6,500,128 B2 | 12/2002 | Marino |
| 6,524,320 B2 | 2/2003 | DiPoto |
| 6,535,759 B1 | 3/2003 | Epstein et al. |
| 6,564,078 B1 | 5/2003 | Marino et al. |
| 6,579,244 B2 | 6/2003 | Goodwin |
| 6,620,157 B1 | 9/2003 | Dabney et al. |
| 6,719,692 B2 | 4/2004 | Kleffner et al. |
| 6,760,616 B2 | 7/2004 | Hoey et al. |
| 6,796,985 B2 | 9/2004 | Bolger et al. |
| 6,810,281 B2 | 10/2004 | Brock et al. |
| 6,819,956 B2 | 11/2004 | DiLorenzo |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,902,569 B2 | 6/2005 | Parmer et al. |
| 6,926,728 B2 | 8/2005 | Zucherman et al. |
| 6,929,606 B2 | 8/2005 | Ritland |
| 6,945,933 B2 | 9/2005 | Branch |
| 7,047,082 B1 | 5/2006 | Schrom et al. |
| 7,050,848 B2 | 5/2006 | Hoey et al. |
| 7,079,883 B2 | 7/2006 | Marino et al. |
| 7,089,059 B1 | 8/2006 | Pless |
| 7,177,677 B2 | 2/2007 | Kaula et al. |
| 7,207,949 B2 | 4/2007 | Miles et al. |
| 7,261,688 B2 | 8/2007 | Smith et al. |
| 7,582,058 B1 | 9/2009 | Miles et al. |
| 2001/0039949 A1 | 11/2001 | Loubser |
| 2001/0056280 A1 | 12/2001 | Underwood et al. |
| 2002/0007129 A1 | 1/2002 | Marino |

| | | |
|---|---|---|
| 2002/0010392 A1 | 1/2002 | Desai |
| 2002/0072686 A1 | 6/2002 | Hoey et al. |
| 2002/0123780 A1 | 9/2002 | Grill et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0105503 A1 | 6/2003 | Marino |
| 2003/0149341 A1 | 8/2003 | Clifton |
| 2003/0225405 A1 | 12/2003 | Weiner |
| 2003/0236544 A1* | 12/2003 | Lunsford et al. ............ 606/190 |
| 2004/0199084 A1 | 10/2004 | Kelleher et al. |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimenta et al. |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 | 1/2007 | Farquhar et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2009/0124860 A1 | 5/2009 | Miles et al. |
| 2009/0138050 A1 | 5/2009 | Ferree |
| 2009/0192403 A1 | 7/2009 | Gharib et al. |
| 2009/0204016 A1 | 8/2009 | Gharib et al. |

FOREIGN PATENT DOCUMENTS

| | | |
|---|---|---|
| EP | 0972538 A2 | 1/2000 |
| FR | 2 795 624 | 1/2001 |
| WO | WO-0038574 A1 | 7/2000 |
| WO | WO 00/67645 | 11/2000 |
| WO | WO-0066217 A1 | 11/2000 |
| WO | WO-0137728 A1 | 5/2001 |
| WO | WO 02/054960 | 7/2002 |
| WO | WO 03/005887 | 1/2003 |
| WO | WO 03/026482 | 4/2003 |
| WO | WO-03037170 A3 | 5/2003 |
| WO | WO-2005013805 A3 | 2/2005 |
| WO | WO 2005/030318 | 4/2005 |
| WO | WO-2006042241 A2 | 4/2006 |
| WO | WO 2006/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDisectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re US Patents 7207949; 7470236 and 7582058, Sep. 18, 2009, 19 pages.
Plaintiffs' Preliminary Invalidity Contentions-Appendices, Sep. 18, 2009, 191 pages.
Plaintiffs' Supplemental Preliminary Invalidity Contentions re US Patents 7207949, 7470236, and 7582058, Sep. 29, 2009, 21 pages.
Plaintiffs' Supplemental Preliminary Invalidity Contentions-Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "Union™ / Union-L™ Anterior & Lateral Impacted Fusion Devices: Clear choice of stabilization," *Medtronic Sofamor Danek*, 2000, 4 pages.
NuVasive Vector™ Cannulae, 1 page (prior to Sep. 25, 2003).
NuVasive Triad™ Tri-Columnar Spinal EndoArthrodesis™ via Minimally Invasive Guidance, 1 page (prior to Sep. 25, 2003).
NuVasive Triad™ Cortical Bone Allograft, 1 page (prior to Sep. 25, 2003).
NuVasive Vertebral Body Access System, 1 page (prior to Sep. 25, 2003).
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasive™ Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
NuVasive letter re 510(k) Premarket Notification INS-1 Intraoperative Nerve Surveillance System, Aug. 24, 2000, 81 pages.
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.
Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
Medtronic Sofamor Danek "Union™ / Union-L™ Anterior & Lateral Impacted Fusion Devices: Surgical Technique" *Medtronic Sofamor Danek*, 2001, 20 pages.
Defendant's Disclosure of Asserted Claims and Preliminary Infringement Contentions Regarding USP 7207949; 7470236 and 7582058, Aug. 31, 2009, 21 pages.
Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine, 1998*, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine, 1998*, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Crock, H. V., M.D.., "Anterior Lumbar Interbody Fusion ," Clinical Orthopaedics and Related Research, No. One Hundred Sixty Five, 1982, pp. 157-163. 13 pages.

"Brackmann II EMG System", *Medical Electronics* (1999),4 pages.

"Electromyography System", *International Search Report*, International Application No. PCT/US00/32329,(Apr. 27, 2001),9 pages.

"Nerve Proximity and Status Detection System and Method", *International Search Report*, International Application No. PCT/US01/18606,(Oct. 18, 2001),6 pages.

"Neurovision SE Nerve Locator/Monitor", *RLN Systems, Inc. Operators Manual*, (1999),22 pages.

"Relative Nerve Movement and Status Detection System and Method", *International Search Report*, International Application No. PCT/US01/18579,(Jan. 15, 2002),6 pages.

"System and Method for Determining Nerve Proximity, Direction, and Pathology During Surgery", *International Search Report*, International Application No. PCT/US02/22247,(Mar. 27, 2003),4 pages.

"System and Methods for Determining Nerve Direction to a Surgical Instrument", *International Search Report*, International Application No. PCT/US03/02056,(Aug. 12, 2003),5 pages.

"Systems and Methods for Performing Percutaneous Pedicle Integrity Assessments", *International Search Report*, International Application No. PCT/US02/35047,(Aug. 11, 2003),5 pages.

"Systems and Methods for Performing Surgery Procedures and Assessments", *International Search Report*, International Application No. PCT/US02/30617,(Jun. 5, 2003),4 pages.

"The Brackmann II EMG Monitoring System", *Medical Electronics Co. Operator's Manual Version 1.1*, (1995),50 pages.

"The Nicolet Viking IV", *Nicolet Biomedical Products*, (1999),6 pages.

Anderson, D. G., et al., "Pedicle screws with high electrical resistance: a potential source of error with stimulus-evoked EMG", *Spine*. 27(14):, Department of Orthopaedic Surgery, University of Virginia,(Jul. 15, 2002),1577-1581.

Bose, Bikash, et al., "Neurophysiologic Monitoring of Spinal Nerve Root Function During Instrumented Posterior Lumbar Spine Surgery", *Spine*, 27(13), (2002),1444-1450.

Calancir, Blair, et al., "Stimulus-Evoked EMG Monitoring During Transpedicular Lumbosacral Spine Instrumentation", *Spine*, 19(24), (1994),2780-2786.

Clements, David, et al., "Evoked and Spontaneous Electromyography to Evaluate Lumbosacral Pedicle Screw Placement", *Spine*, 21(5), (1996),600-604.

Danesh-Clough, T., "The use of evoked EMG in detecting misplaced thoracolumbar pedicle screws", *Spine*. 26(12), Orthopaedic Department, Dunedin Hospital,(Jun. 15, 2001),1313-1316.

Darden, B. V., et al., "A comparison of impedance and electromyogram measurements in detecting the presence of pedicle wall breakthrough", *Spine*. 23(2). Charlotte Spine Center, North Carolina,(Jan. 15, 1998),256-262.

Ebraheim, N. A., et al., "Anatomic relations between the lumbar pedicle and the adjacent neural structures", *Spine*. 22(20), Department of Orthopaedic Surgery, Medical College of Ohio,(Oct. 15, 1997),2338-2341.

Ford, Douglas, "Electrical Characteristics of Peripheral Nerve Stimulators Implications for Nerve Localization", *Regional Anesthesia*, 9, (1984),73-77.

Glassman, Steven, "A Prospective Analysis of Intraoperative Electromyographic Monitoring of Pedicle Screw Placement With Computed Tomographic Scan Confirmation", *Spine* , 20(12), (1995),1375-1379.

Greenblatt, Gordon, "Needle Nerve Stimulator-Locator: Nerve Blocks with a New Instrument for Locating Nerves", *Anesthesia & Analgesia*, 41(5), (1962),599-602.

Haig, A. J., et al., "The relation among spinal geometry on MRI, paraspinal electromyographic abnormalities, and age in persons referred for electrodiagnostic testing of low back symptoms", *Spine*. 27(17), Department of Physical Medicine and Rehabilitation, University of Michigan,(Sep. 1, 2002),1918-1925.

Holland, N. R., et al., "Higher electrical stimulus intensities are required to activate chronically compressed nerve roots. Implications for intraoperative electromyographic pedicle screw testing", *Spine*. 23(2), Department of Neurology, Johns Hopkins University School of Medicine,(Jan. 15, 1998),224-227.

Holland, Neil, "Intraoperative Electromyography During Thoracolumbar Spinal Surgery", *Spine*. 23(17), (1998),1915-1922.

Journee, H. L., et al., "System for Intra-Operative Monitoring of the Cortical Integrity of the Pedicle During Screw Placement in Low-Back Surgery: Design and Clinical Results", *Sensory and neuromuscular diagnostic instrumentation and data analysis, 18th Annual International Conference on Engineering in Medicine and Biology Society*, 1(31), (Oct. 1996),144-145.

Lenke, Lawrence, "Triggered Electromyographic Threshold for Accuracy of Pedicle Screw Placement", *Spine*, 20 (14), (1995),1585-1591.

Maguire, J., et al., "Evaluation of Intrapedicular Screw Position Using Intraoperative Evoked Electromyography", *Spine*, 20(9), (1995),1068-1074.

Martin, David, et al., "Initiation of Erection and Semen Release by Rectal Probe Electrostimulation (RPE)", *The Williams & Wilkins Co.*, (1983),637-642.

Minahan, R. E., et al., "The effect of neuromuscular blockade on pedicle screw stimulation thresholds", *Spine.* 25(19), Department of Neurology, Johns Hopkins University, School of Medicine,(Oct. 1, 2000),2526-2530.

Pither, Charles, et al., ""The Use of Peripheral Nerve Stimulators for Regional Anesthesia: Review of Experimental Characteristics, Technique, and Clinical Applications"", *Regional Anesthesia* (1985),10:47-53.

Raj, P. , et al., "Infraclavicular Brachial Plexus Block—A New Approach", *Anesthesia and Analgesia*, (52)6, (1973),897-904.

Raj, P. , et al., "The Use of Peripheral Nerve Stimulators for Regional Anesthesia", *Clinical Issues in Regional Anesthesia*, 1 (4), (1985),1-6.

Raj, P. , et al., "Use of the nerve Stimulator of Peripheral Blocks", *Regional Anesthesia* , (Apr.-Jun. 1980),14-21.

Raymond, Stephen, et al., "The Nerve Seeker: A System for Automated Nerve Localization", *Regional Anesthesia*, 17(3), (1992),151-162.

Shafik, Ahmed, "Cavernous Nerve Simulation through an Extrapelvic Subpubic Approach: Role in Pencil Erection", *Eur. Urol*, 26, (1994),98-102.

Toleikis, J., et al., "The Usefulness of Electrical Stimulation for Assessing Pedicle Screw Replacements", *Journal of Spinal Disorder*, 13(4), (2000),283-289.

\* cited by examiner

SURGICAL ACCESS SYSTEM AND RELATED METHODS

CROSS REFERENCE TO RELATED APPLICATIONS

The present application claims the benefit of priority from commonly owned and co-pending U.S. Provisional Patent Application Ser. No. 60/512,594 (filed on Oct. 17, 2003 by Curran et al.) entitled "System and Methods for Performing Lateral Lumbar Surgery," the entire contents of which is hereby expressly incorporated by reference into this disclosure as if set forth fully herein. The present application also incorporates by reference the following co-pending and co-assigned patent applications in their entireties: PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003 (collectively "NeuroVision PCT Applications").

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire, an initial dilator of split construction, and one or more dilators of traditional (that is, non-split) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't infringe upon the region of the exiting nerve roots.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue.

In a preferred embodiment, only the posterior retractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

According to another aspect of the invention, a minimally invasive lateral lumber surgery may be performed using various embodiments of the surgical access system. The surgical method may be accomplished by guiding at least a portion of the tissue distraction assembly to the surgical target site using a lateral, retroperitoneal approach. According to some embodiments, the access system is used to access the lumbar spine via a direct lateral, retroperitoneal approach. In such embodiments, blunt finger dissection may be used to safely enter the retroperitoneal space posteriorly and sweep the peritoneal cavity anteriorly. A distal end of the K-wire, and possibly other components of the tissue distraction assembly, are then escorted through the retroperitoneal space to the psoas muscle utilizing finger dissection. In some instances, the initial dilator is guided through the retroperitoneal space by a finger in contact with the distal end, so the potential of peritoneal disruption may be reduced.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
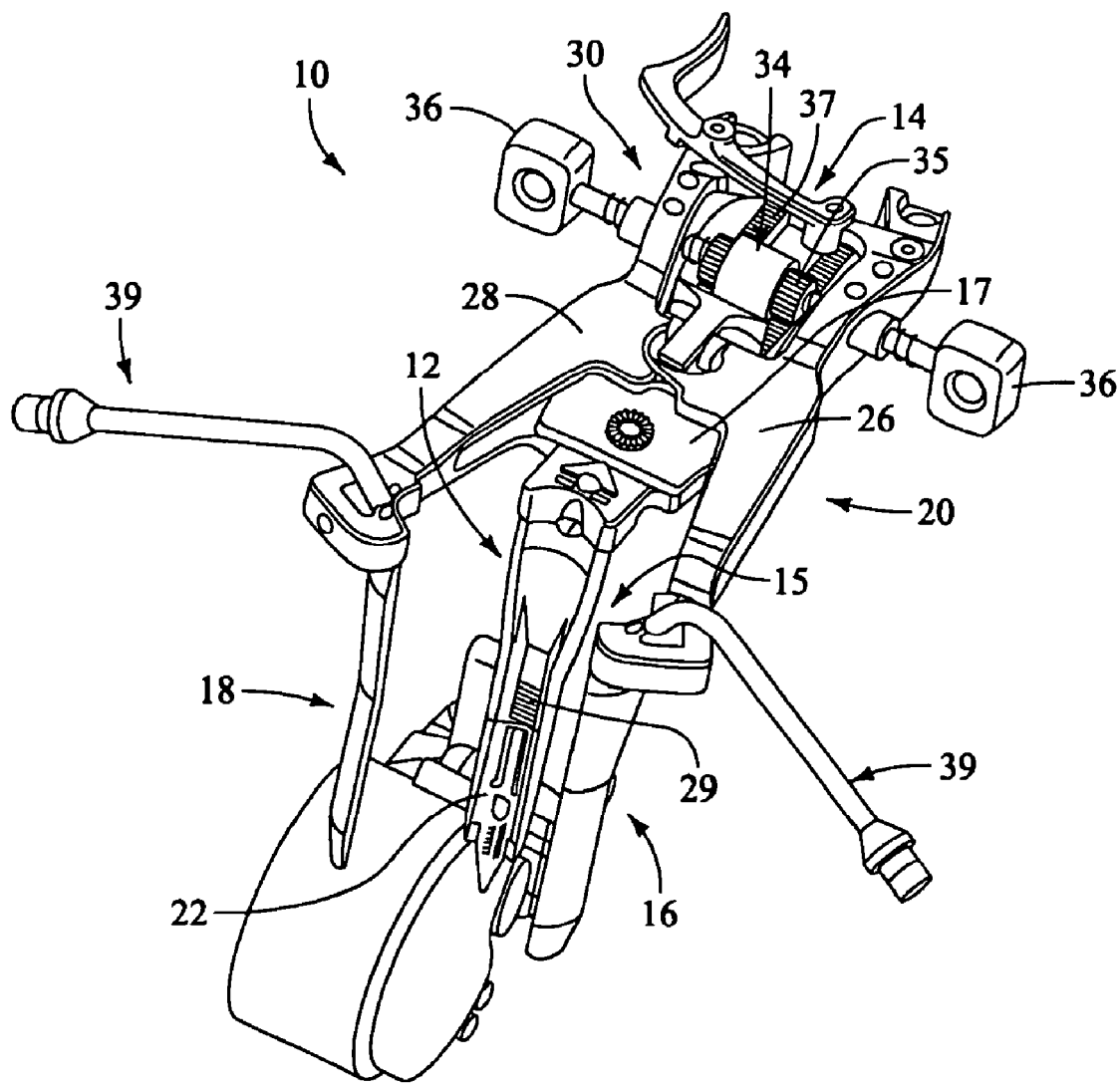
FIG. 1 is a perspective view of a tissue retraction assembly (in use) forming part of a surgical access system according to the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures. In some embodiments, the surgical access system may be used access a surgical target site on the spine via a substantially lateral, retroperitoneal approach (as shown, for example, in FIGS. 23-50).

These electrodes are preferably provided for use with a nerve surveillance system such as, by way of example, the type shown and described in the co-pending and commonly assigned NeuroVision PCT Applications referenced above, the entire contents of which are expressly incorporated by reference as if set forth herein in their entirety. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc). A secondary distraction assembly (i.e. a plurality of sequentially dilating cannulae) may optionally be employed after the initial distraction assembly to further distract the tissue. Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slideably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (i.e. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (i.e. nerves, vasculature, etc. . . . ) into or out of the operative corridor. Once the operative corridor is established, any of a variety of surgical instruments, devices, or implants may be passed through and/or manipulated within the operative corridor depending upon the given surgical procedure.

FIG. 1 illustrates a tissue retraction assembly 10 forming part of a surgical access system according to the present invention. The retraction assembly 10 includes a plurality of retractor blades extending from a handle assembly 20. By way of example only, the handle assembly 20 is provided with a first retractor blade 12, a second retractor blade 16, and a third retractor blade 18. The retractor assembly 10 is shown in a fully retracted or "open" configuration, with the retractor blades 12, 16, 18 positioned a distance from one another so as to form an operative corridor 15 there between and extending to a surgical target site (e.g. an annulus of an intervertebral disc). Although shown and described below with regard to the three-bladed configuration, it is to be readily appreciated that the number of retractor blades may be increased or decreased without departing from the scope of the present invention. Moreover, although described and shown herein, for example in FIGS. 1, 9-18, and 23-50, with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the retractor assembly 10 of the present invention may find use in any number of different surgical approaches, including generally posterior, generally postero-lateral, generally anterior and generally antero-lateral.

Figure 2:
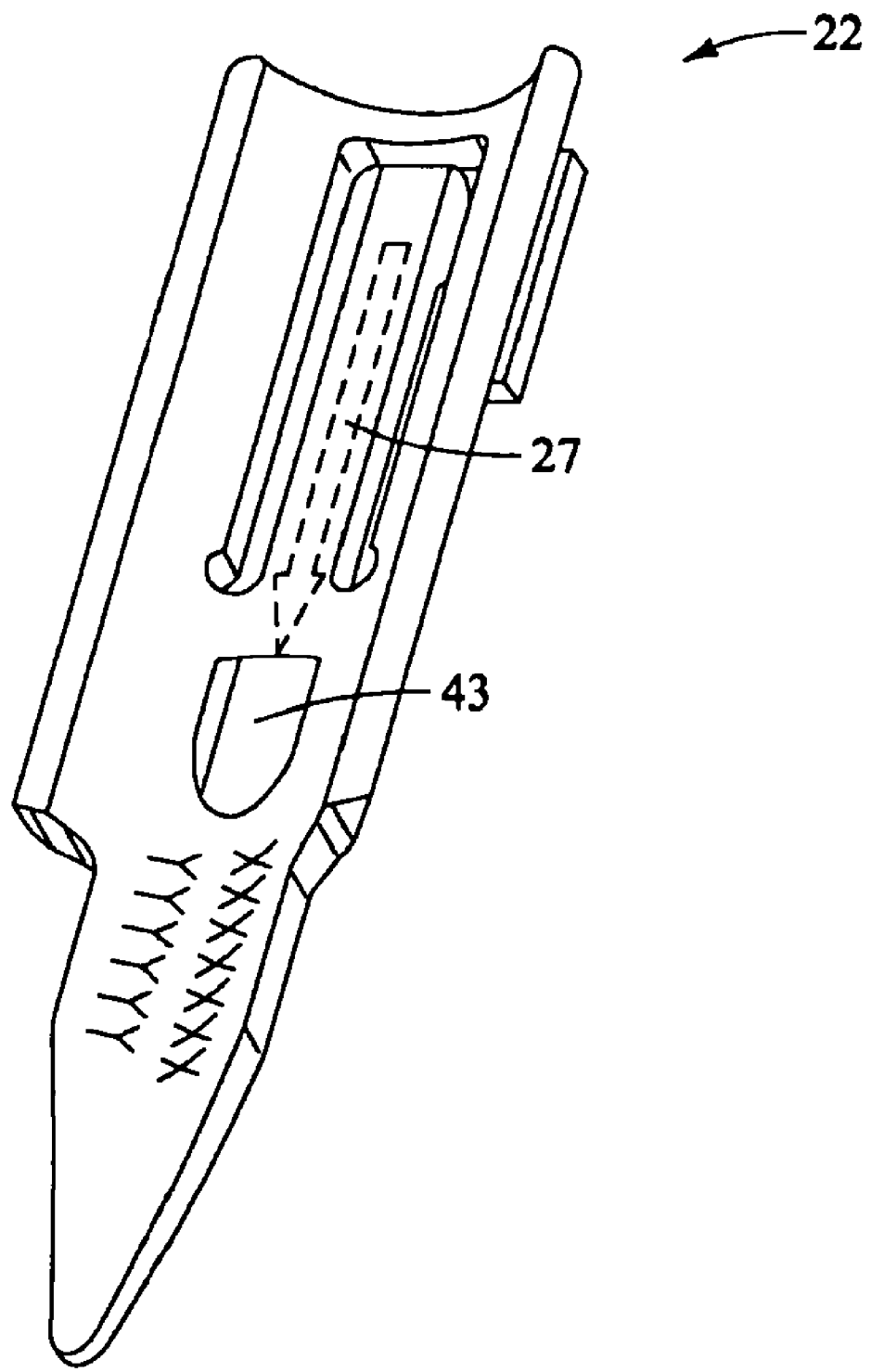
FIGS. 2-3 are perspective views illustrating the front and back of a shim element for use with a posterior retractor blade of the retractor according to the retractor of the present invention.
Figure 3:
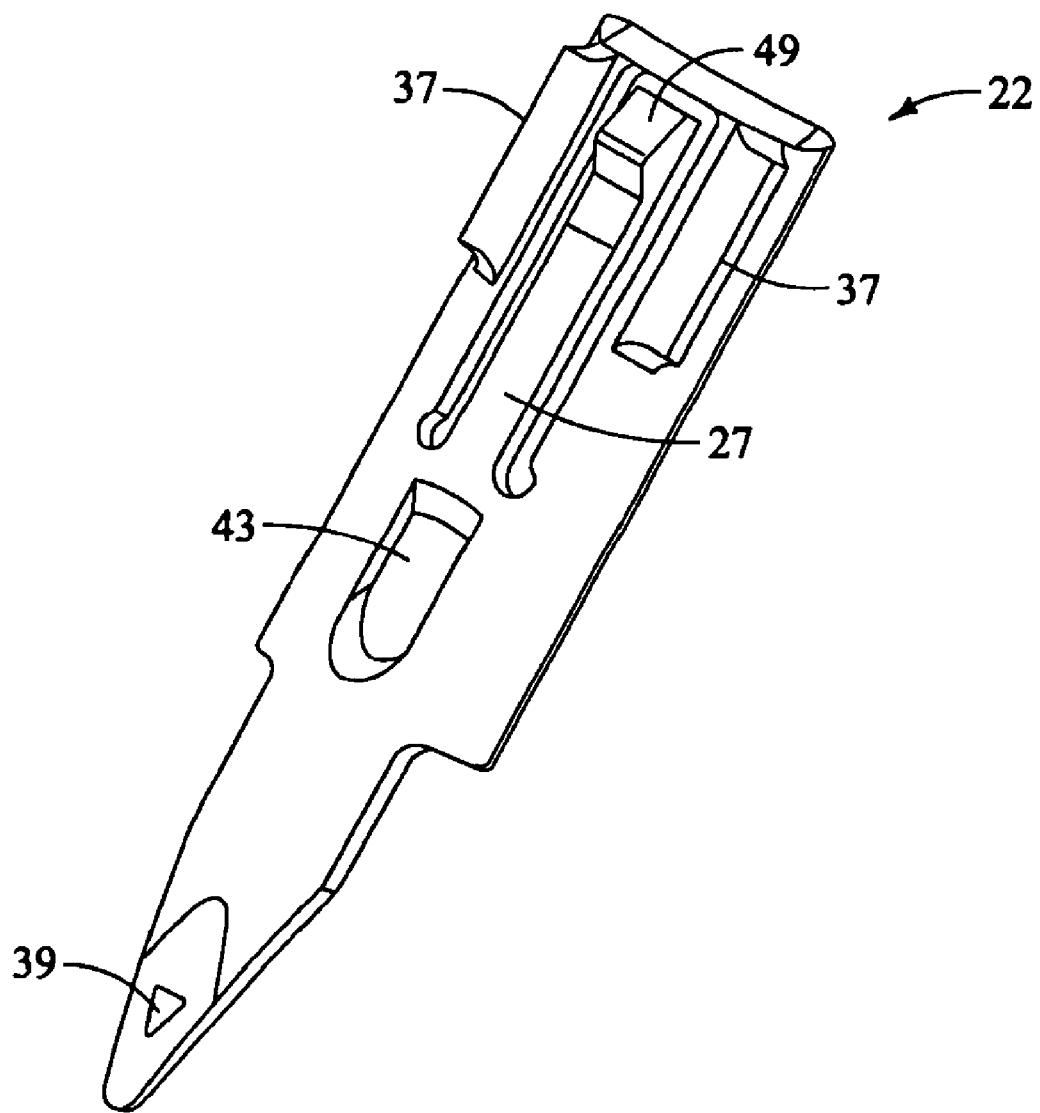
Figure 4:
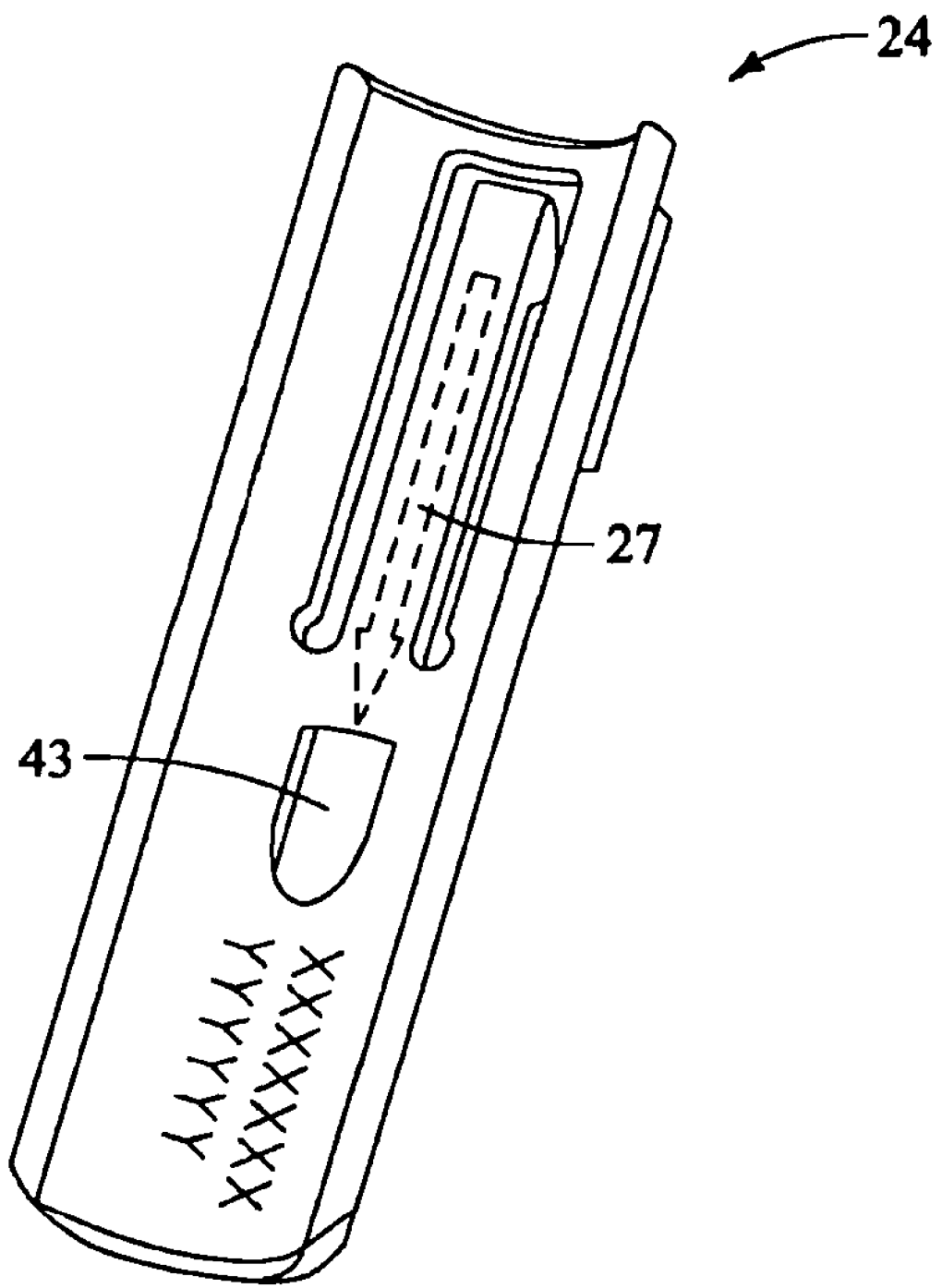
FIGS. 4-5 are perspective views illustrating the front and back of a narrow retractor extender for use with one of a cephalad and caudal retractor blade according to the retractor of the present invention.
Figure 5:
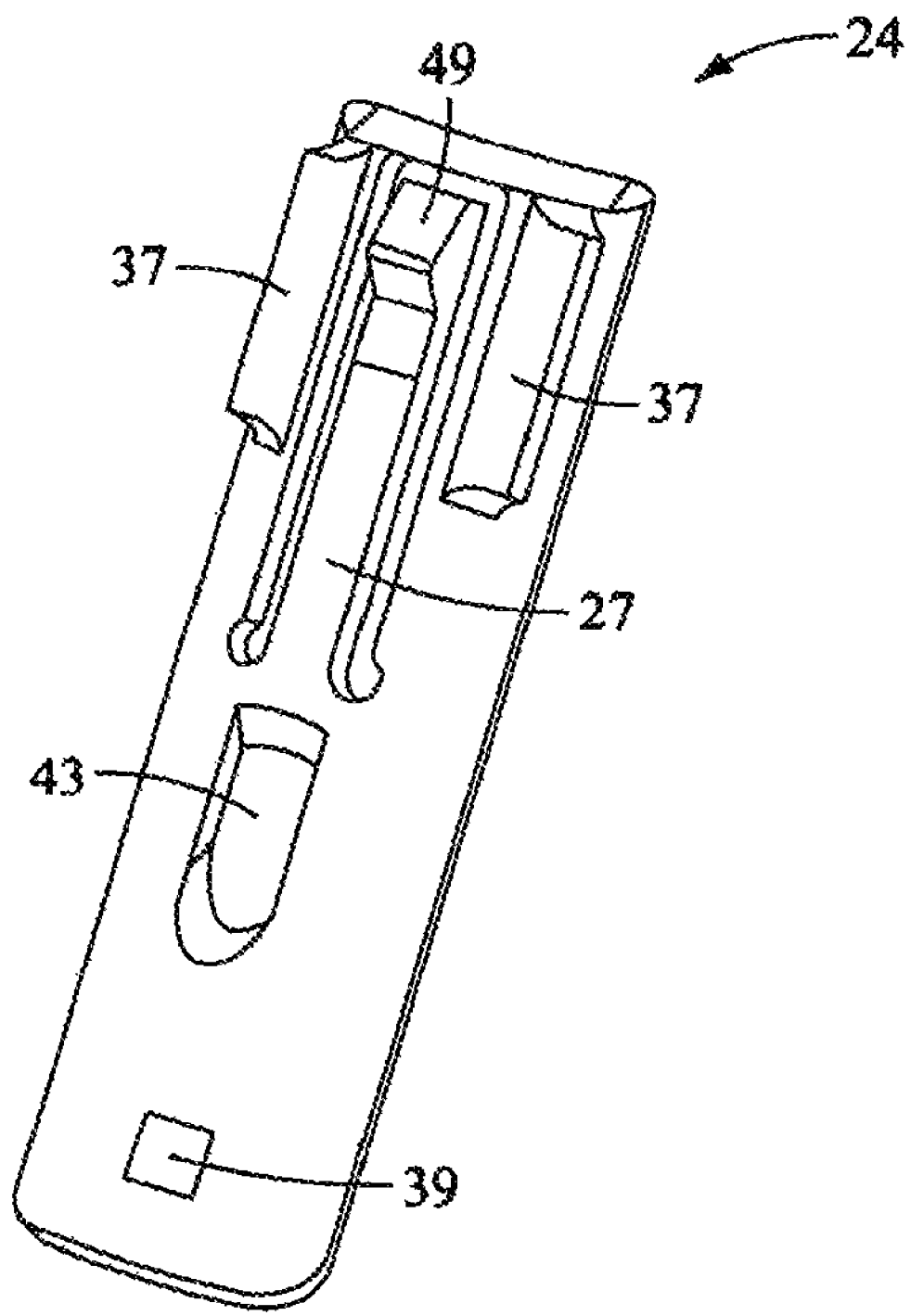
Figure 6:
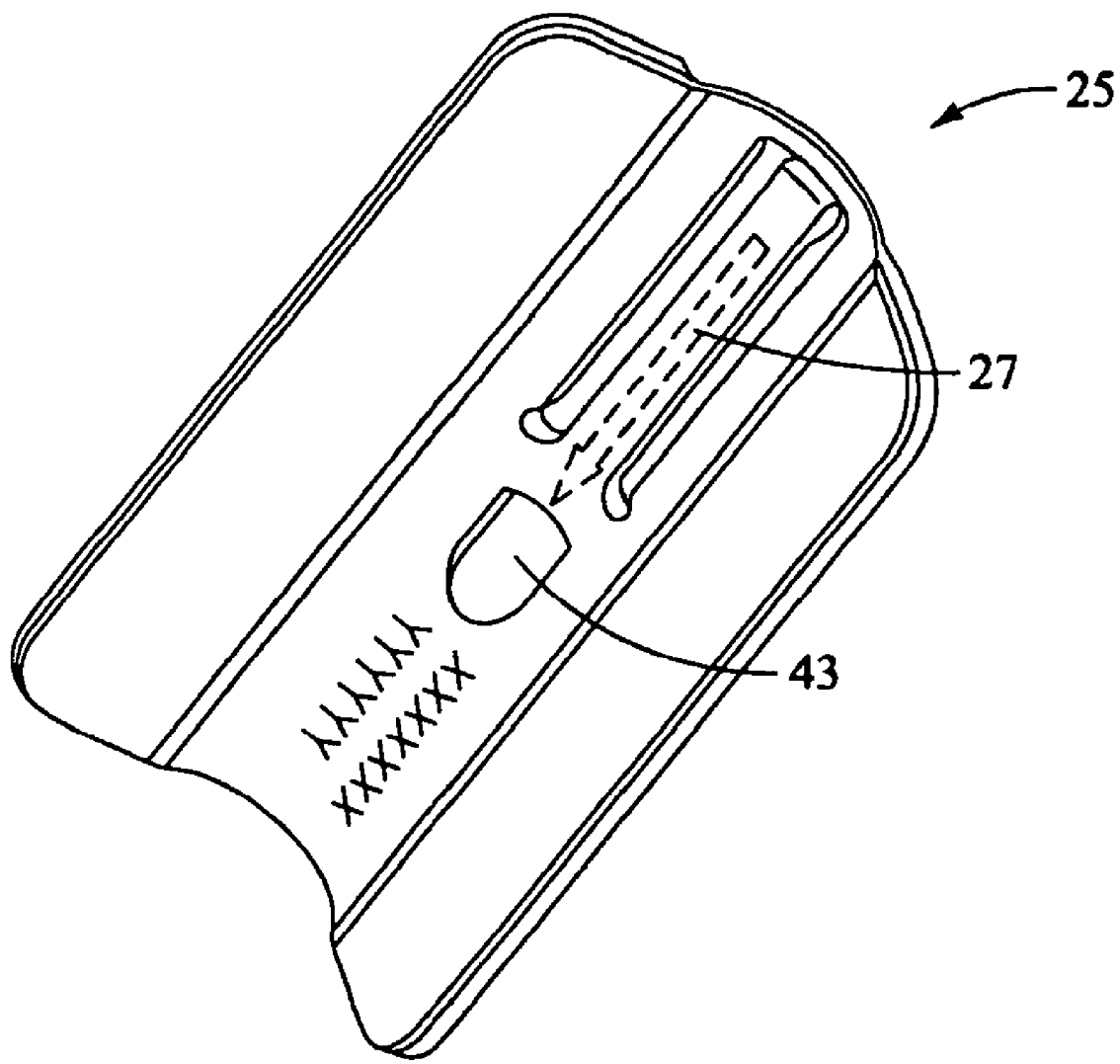
FIGS. 6-7 are perspective views illustrating the front and back of a wide retractor extender for use with one of a cephalad and caudal retractor blade according to the retractor of the present invention.
Figure 7:
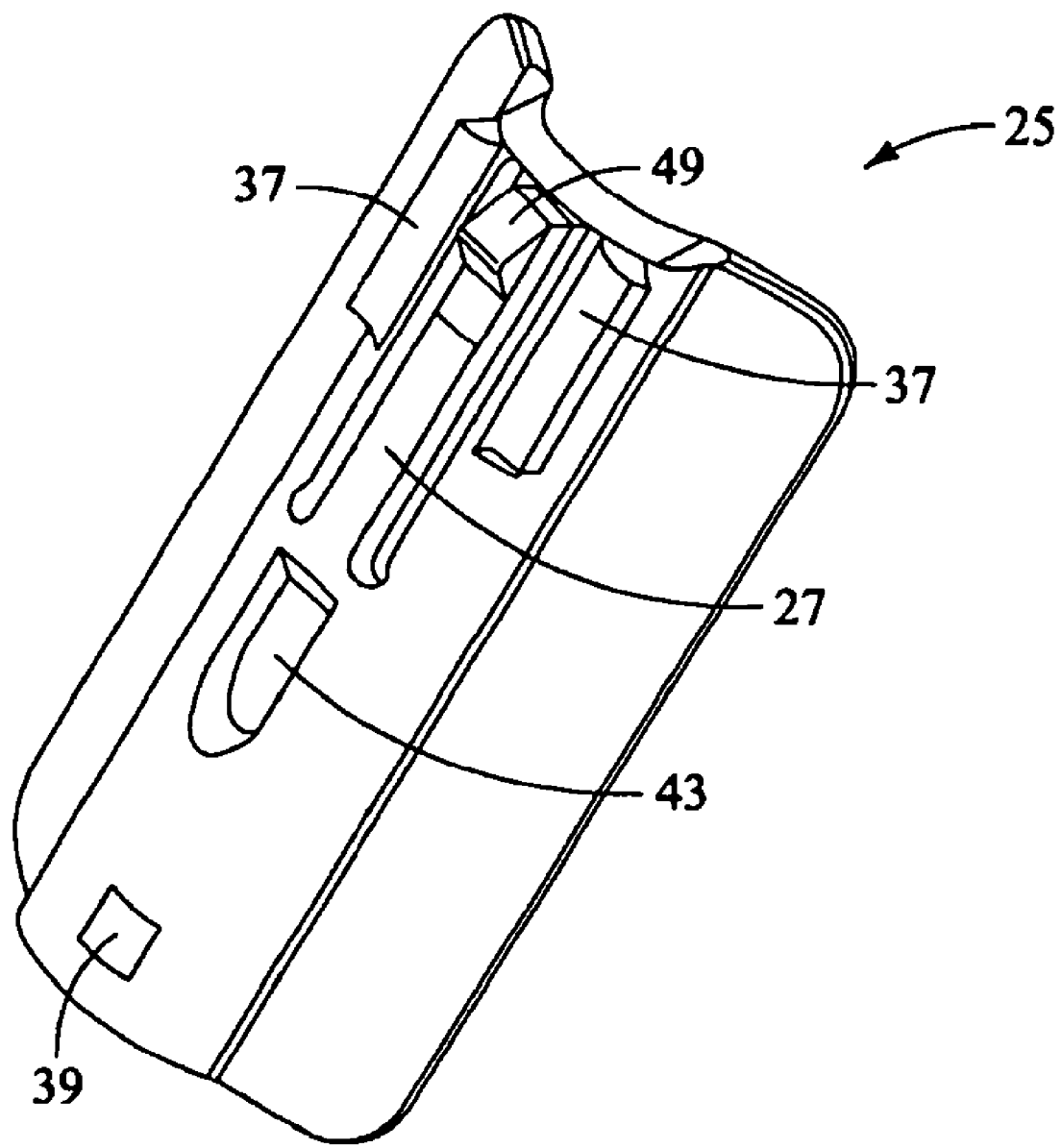

The retractor blades 12, 16, 18 may be equipped with various additional features or components. By way of example only, posterior retractor blade 12 may be equipped with a shim element 22 (shown more clearly in FIGS. 2-3). Shim element 22 serves to distract the adjacent vertebral bodies (thereby restoring disc height), helps secure the retractor assembly 10 relative to the surgical target site, and forms a protective barrier to prevent the ingress or egress of instruments or biological structures (i.e. nerves, vasculature, etc. . . . ) into or out of the operative corridor. Each of the remaining retractor blades (cephalad-most blade 16 and caudal-most blade 18) may be equipped with a retractor extender, such as the narrow retractor extender 24 shown in FIGS. 4-5 or the wide retractor extender 25 shown in FIGS. 6-7. The retractor extenders 24/25 extend from the cephalad-most and caudal-most retractor blades 16, 18 to form a protective barrier to prevent the ingress or egress of instruments or biological structures (i.e. nerves, vasculature, etc. . . . ) into or out of the operative corridor 15.

According to the present invention, any or all of the retractor blades 12, 16, 18, the shim element 22 and/or the retractor extenders 24/25 may be provided with one or more electrodes 39 (preferably at their distal regions) equipped for use with a nerve surveillance system, such as, by way of example, the type shown and described in the NeuroVision PCT Applications. Each of the shim element 22 and/or the retractor extenders 24/25 may also be equipped with a mechanism to selectively and releasably engage with the respective retractor blades 12, 16, 18. By way of example only, this may be accomplished by configuring the shim element 22 and/or the retractor extenders 24/25 with a tab element 27 capable of engaging with corresponding rachet-like grooves (shown at 29 in FIG. 1) along the inner-facing surfaces of the retractor blades 12, 16, 18. Each of the shim element 22 and/or the retractor extenders 24/25 is provided with a pair of engagement elements 37 having, by way of example only, a generally dove-tailed cross-sectional shape. The engagement elements 37 are dimensioned to engage with receiving portions on the respective retractor blades 12, 16, 18. In a preferred embodiment, each of the shim element 22 and/or the retractor extenders 24/25 are provided with an elongate slot 43 for engagement with an insertion tool (not shown). Each tab member 27 is also equipped with an enlarged tooth element 49 which engages within corresponding grooves 29 provided along the inner surface of the retractor blades 12, 16, 18.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism shown generally at 30. The cephalad-most retractor blade 16 is rigidly coupled (generally perpendicularly) to the end of the first arm member 26. The caudal-most retractor blade 18 is rigidly coupled (generally perpendicularly) to the end of the second arm member 28. The posterior retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Figure 8:
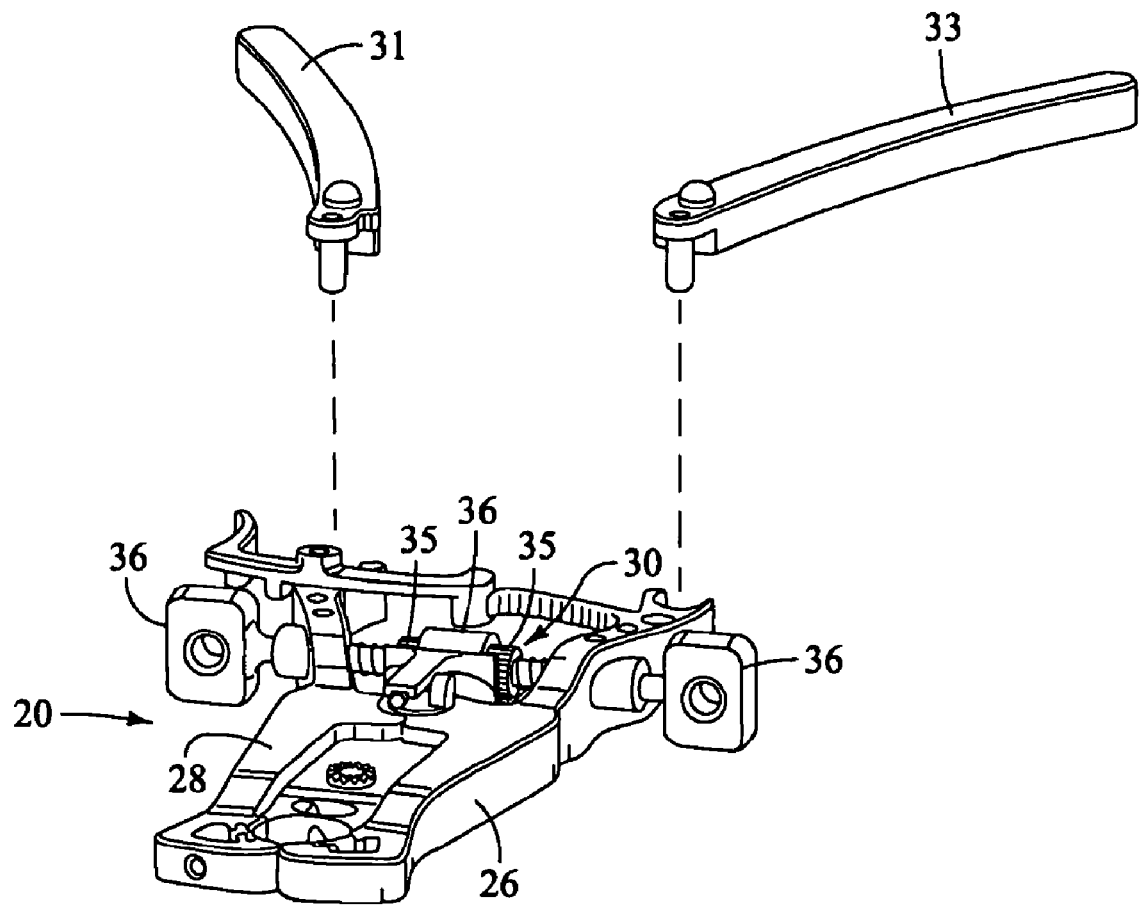
FIG. 8 is a perspective, partially exploded view of the retractor assembly of the present invention, without the retractor blades.

Through the use of handle extenders 31, 33 (FIG. 8), the arms 26, 28 may be simultaneously opened such that the cephalad-most and caudal-most retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, and/or an oval cross-section. Optional light emitting devices 39 may be coupled to one or more of the retractor blades 12, 16, 18 to direct light down the operative corridor 15.

Figure 9:
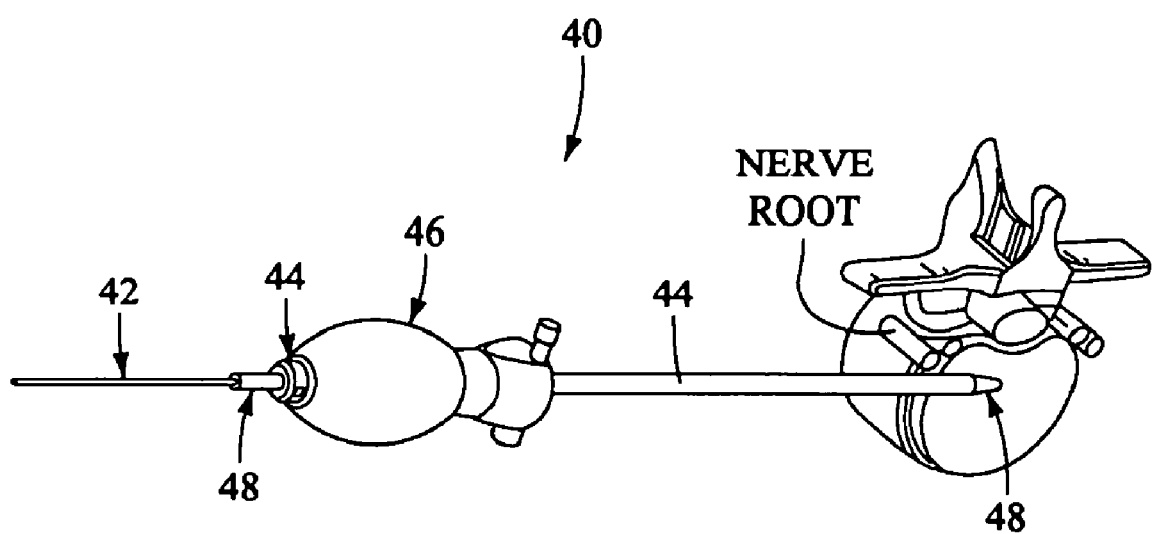
FIG. 9 is a perspective view illustrating the components and use of an initial distraction assembly (i.e. K-wire, an initial dilating cannula with handle, and a split-dilator housed within the initial dilating cannula) forming part of the surgical access system according to the present invention, for use in distracting to a surgical target site (i.e. annulus)
Figure 10:
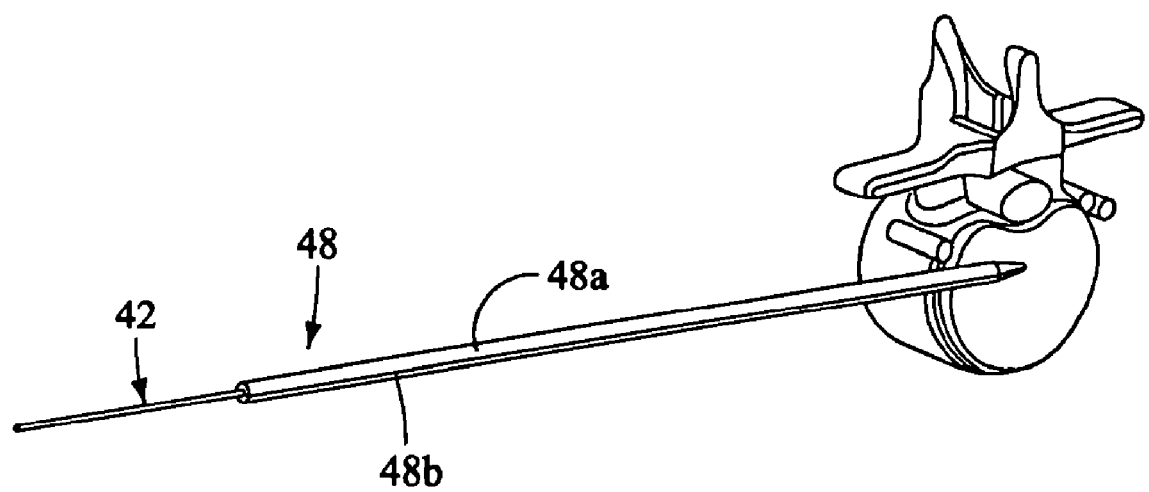
FIG. 10 is a perspective view illustrating the K-wire and split-dilator of the initial distraction assembly with the initial dilating cannula and handle removed.
Figure 11:
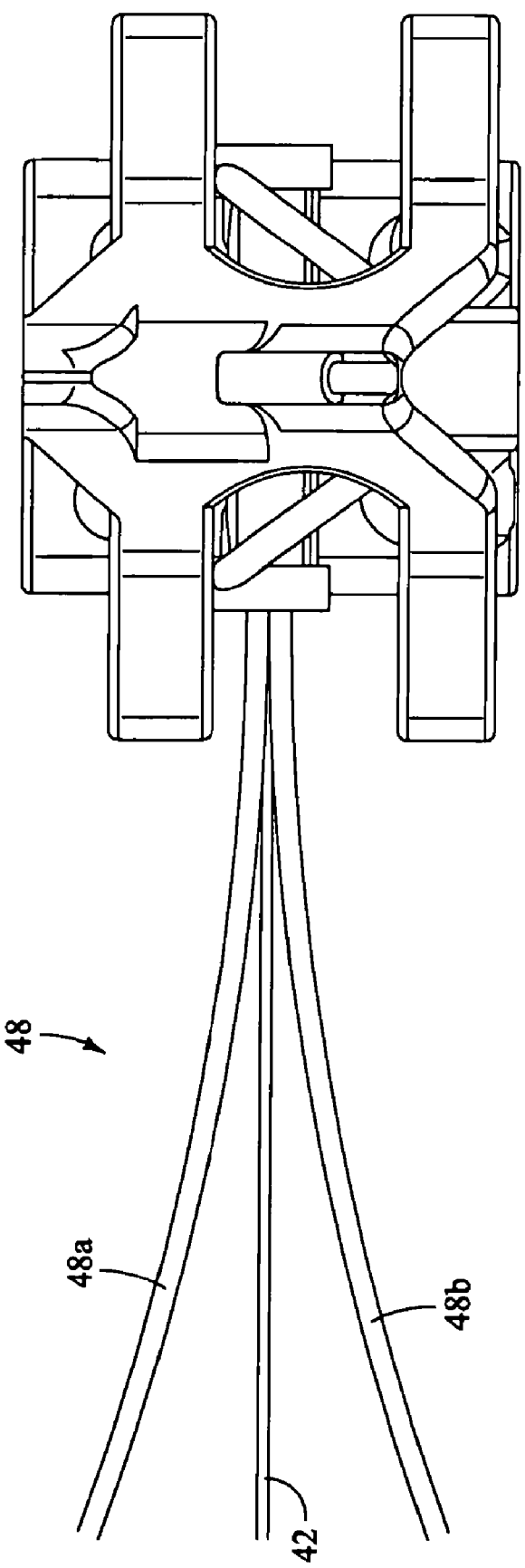
FIG. 11 is a posterior view of the vertebral target site illustrating the split-dilator of the present invention in use distracting in a generally cephalad-caudal fashion according to one aspect of the present invention.

FIG. 9 illustrates an initial distraction assembly 40 forming part of the surgical access system according to the present invention. The initial distraction assembly 40 includes a K-wire 42, an initial dilating cannula 44 with handle 46, and a split-dilator 48 housed within the initial dilating cannula 44. In use, the K-wire 42 and split-dilator 48 are disposed within the initial dilating cannula 44 and the entire assembly 40 advanced through the tissue towards the surgical target site (i.e. annulus). One exemplary method for advancing an initial dilator towards a spinal target site is described in more detail later in connection with FIGS. 23-50. Again, this is preferably accomplished while employing the nerve detection and/or direction features described above. After the initial dilating assembly 40 is advanced such that the distal ends of the split-dilator 48 and initial dilator 44 are positioned within the disc space (FIG. 9), the initial dilator 44 and handle 46 are removed (FIG. 10) to thereby leave the split-dilator 48 and K-wire 42 in place. As shown in FIG. 11, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion. Each dilator halve 48a, 48b may be, according to the present invention, provided with one or more electrodes (preferably at their distal regions) equipped for use with a nerve surveillance system, such as, by way of example, the type shown and described in the NeuroVision PCT Applications.

Figure 12:
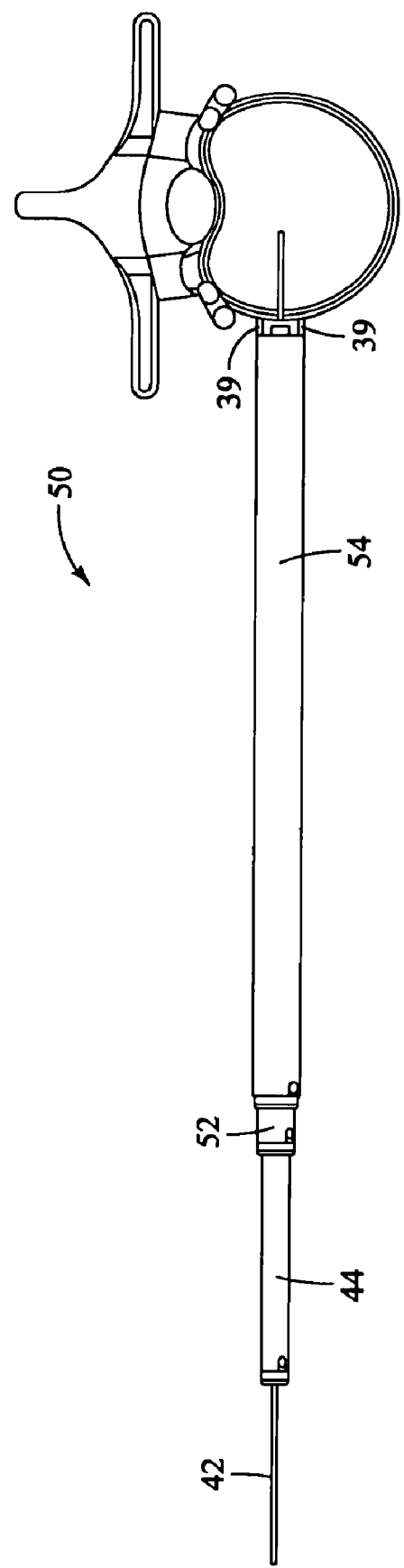
FIG. 12 is a side view illustrating the use of a secondary distraction assembly (comprising a plurality of dilating cannulae over the K-wire) to further distract tissue between the skin of the patient and the surgical target site according to the present invention.

Following this initial distraction, a secondary distraction may be optionally undertaken, such as via a sequential dilation system 50 as shown in FIG. 12. According to the present invention, the sequential dilation system 50 may include the K-wire 42, the initial dilator 44, and one or more supplemental dilators 52, 54 for the purpose of further dilating the tissue down to the surgical target site. Once again, each component of the secondary distraction assembly 50 (namely, the K-wire 42, the initial dilator 44, and the supplemental dilators 52, 54 may be, according to the present invention, provided with one or more electrodes (preferably at their distal regions) equipped for use with a nerve surveillance system, such as, by way of example, the type shown and described in the Neuro-Vision PCT Applications.

Figure 13:
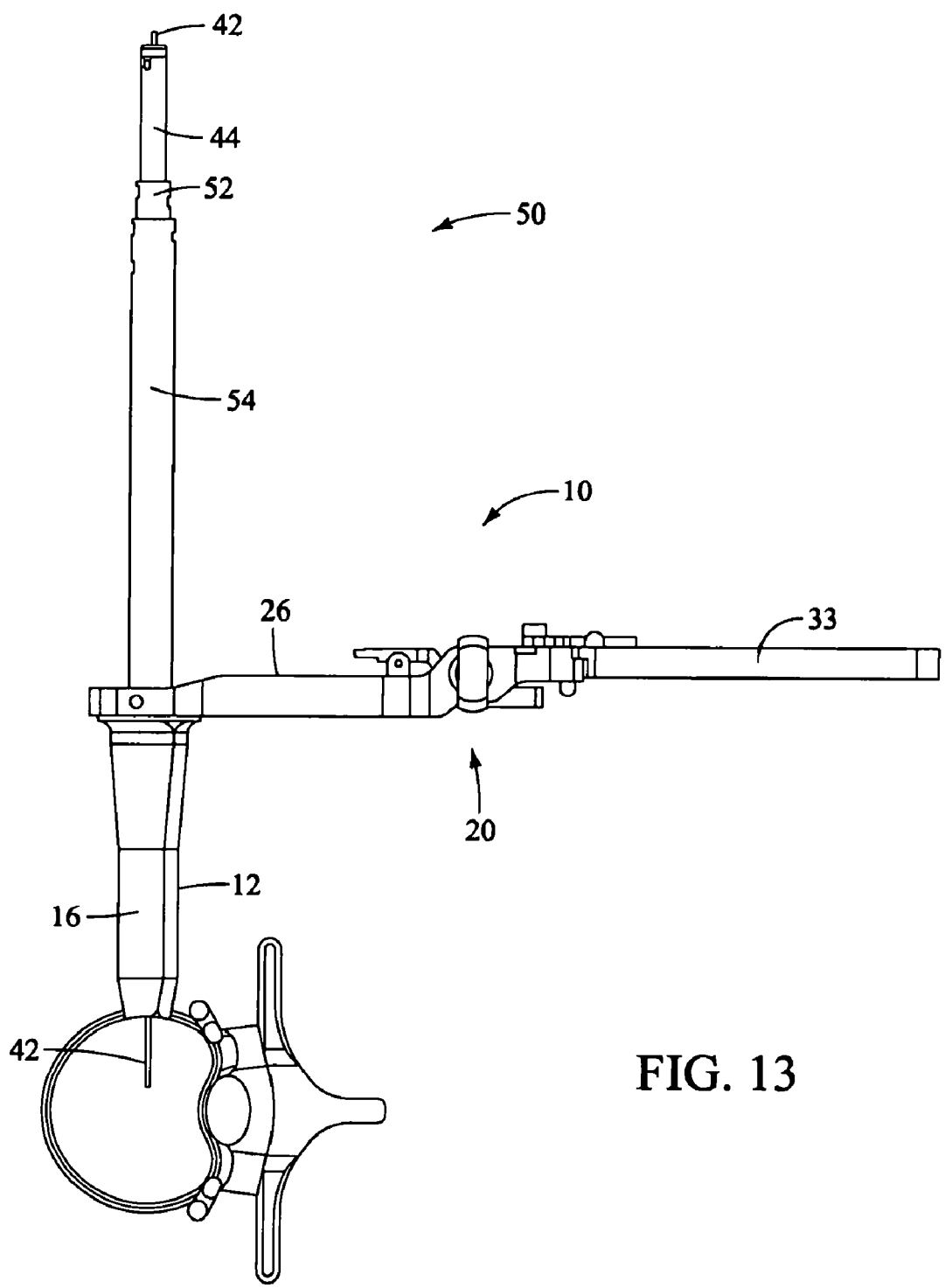
FIG. 13 is a side view of a retractor assembly according to the present invention, comprising a handle assembly having three (3) retractor blades extending there from (posterior, cephalad-most, and caudal-most) disposed over the secondary distraction assembly of FIG. 12 (shown in a first, closed position)
Figure 14:
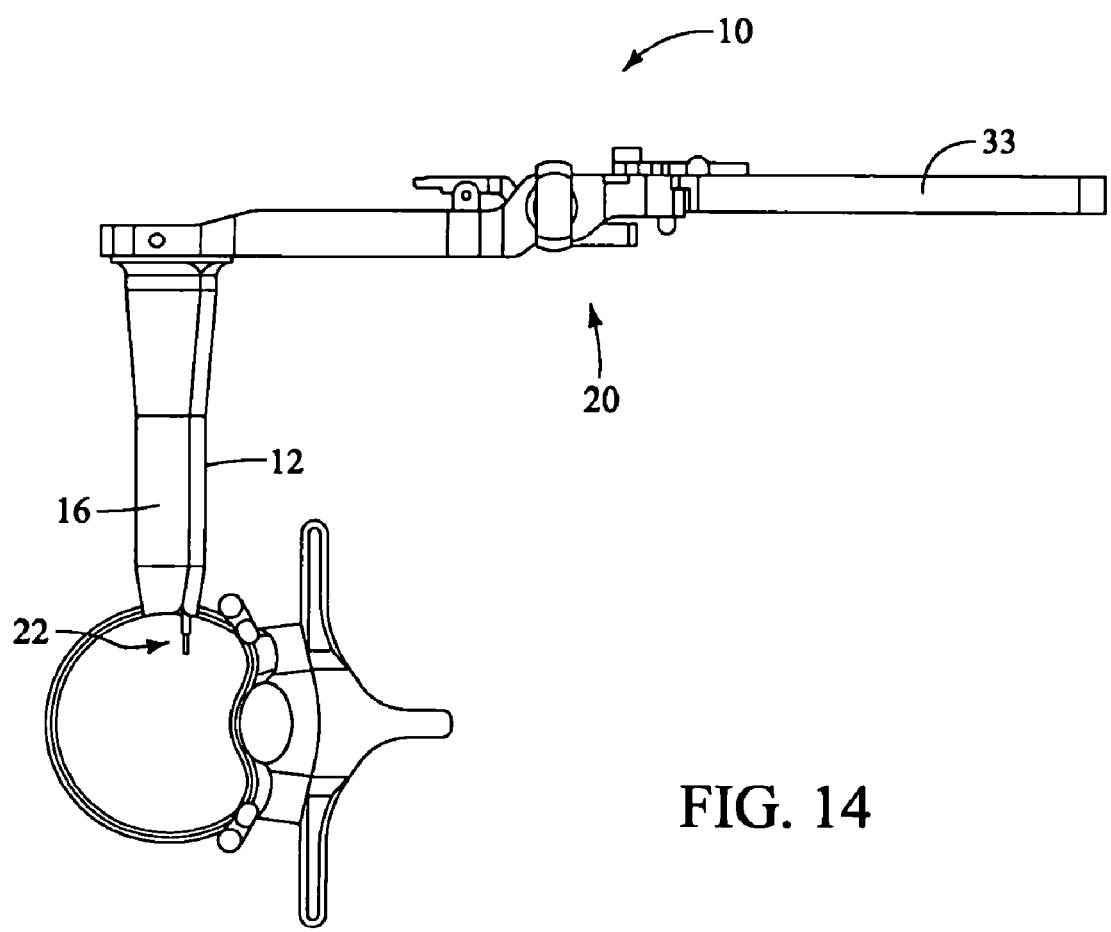
FIG. 14 is a side view of a retractor assembly according to the present invention, comprising a handle assembly having three (3) retractor blades extending there from (posterior, cephalad-most, and caudal-most) with the secondary distraction assembly of FIG. 12 removed and shim element introduced.
Figure 15:
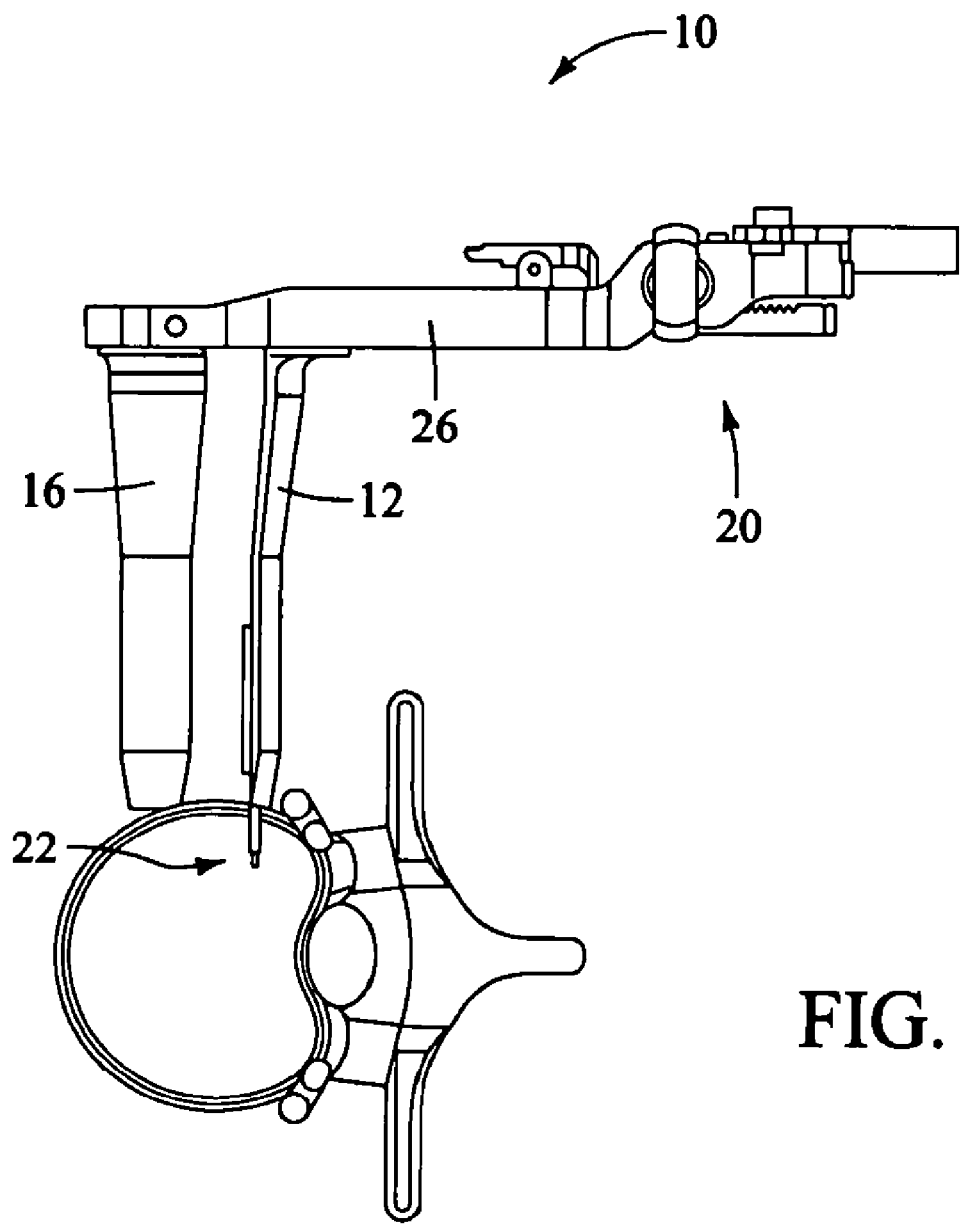
FIGS. 15-16 are perspective and top views, respectively, of the retractor assembly in a second, opened (i.e. retracted) position to thereby create an operative corridor to a surgical target site according to the present invention.
Figure 16:
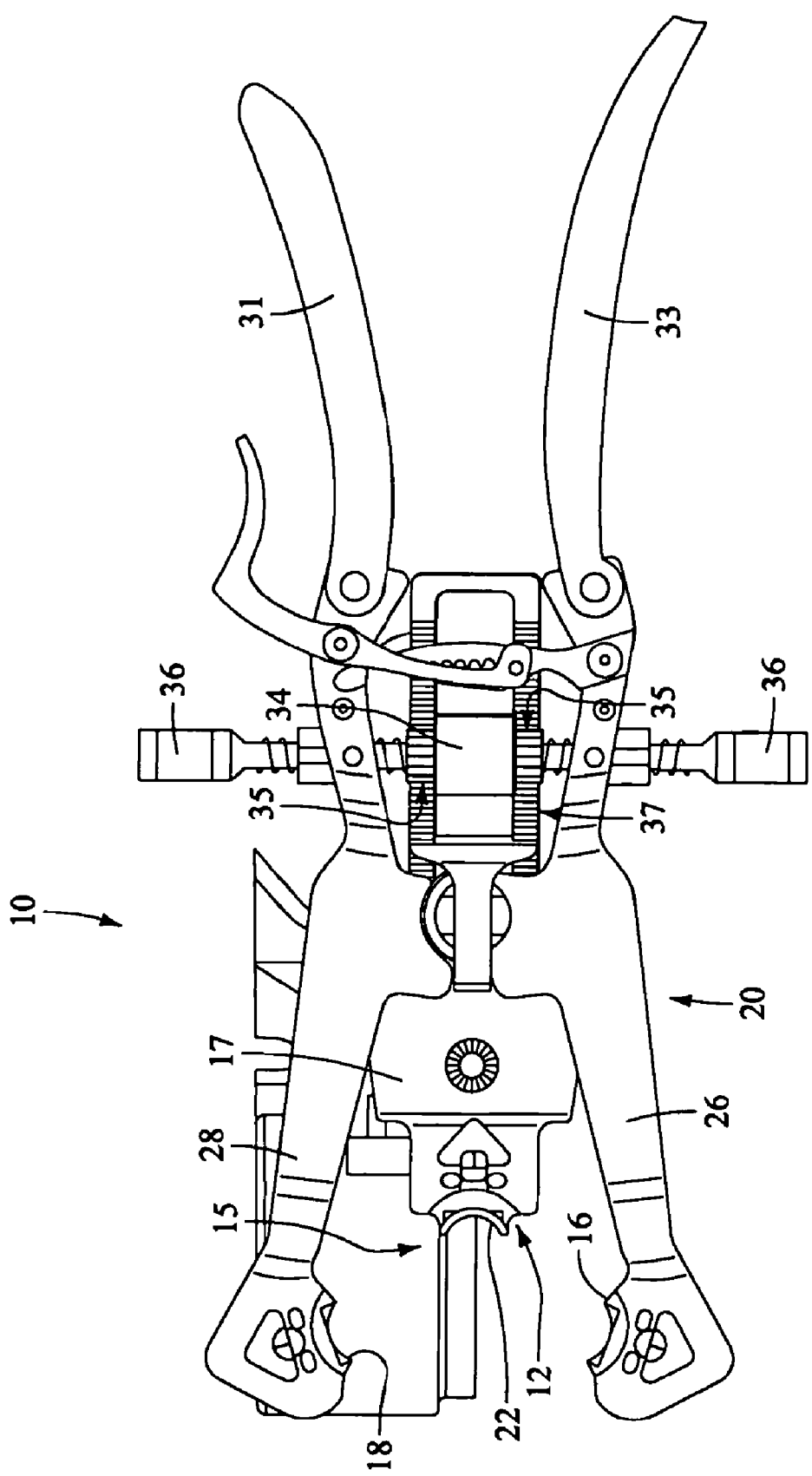
Figure 17:
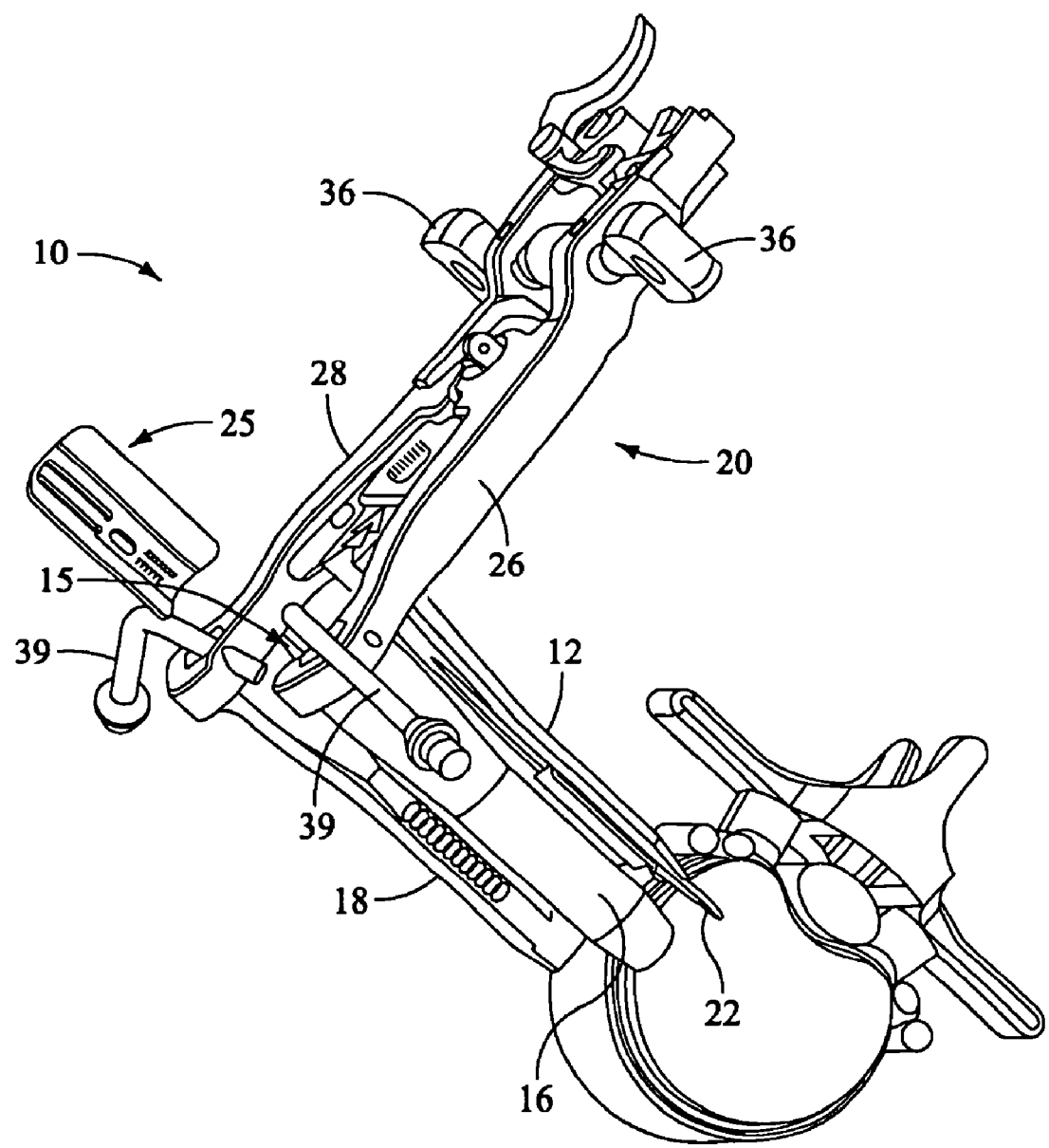
FIGS. 17-18 are perspective and side views, respectively, of the retractor assembly in the second, opened (i.e. retracted) position (with the secondary distraction assembly removed) and with the retractor extenders of FIGS. 4-5 and 6-7 coupled to the retractor according to the present invention.
Figure 18:
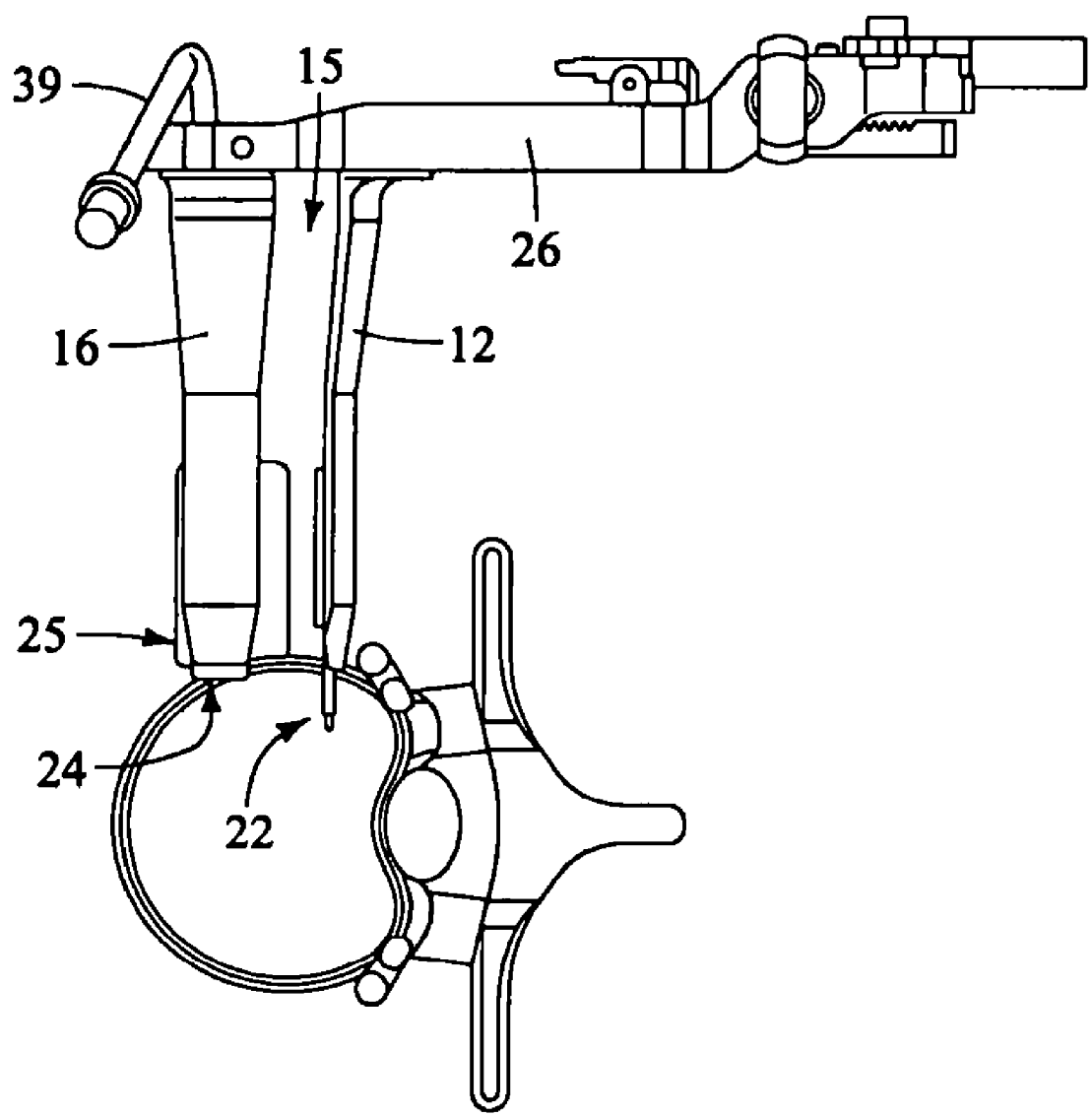

As shown in FIG. 13, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another). Once advanced to the surgical target site, the sequential dilation assembly 50 may be removed and the shim element 22 engaged with the posterior retractor blade 12 such that the distal end thereof extends into the disc space as shown in FIG. 14. At this point, the handle assembly 20 may be operated to move the retractor blades 16, 18 into a second, open or "retracted" position as shown generally in FIGS. 15-16. As one can see, the posterior retractor blade 12 is allowed to stay in the same general position during this process, such that the cephalad-most and caudal-most retractor blades 14, 16 move away from the posterior retractor blade 12. At this point, the narrow and wide retractor extenders 24, 25 may be engaged with the caudal-most retractor blade 18 and cephalad-most retractor blade 16, respectively, as shown in FIGS. 17-18.

As mentioned above, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist). Such monitoring may also be carried out via the surgeon-driven EMG monitoring system shown and described in the following commonly owned and co-pending NeuroVision PCT Applications referenced above. In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed. For example, the surgical access system may be advantageously used to traverse tissue through the retroperitoneal space and the psoas muscle during a substantially lateral, retroperitoneal approach to the lumbar spine, as shown in FIGS. 23-50.

Figure 19:
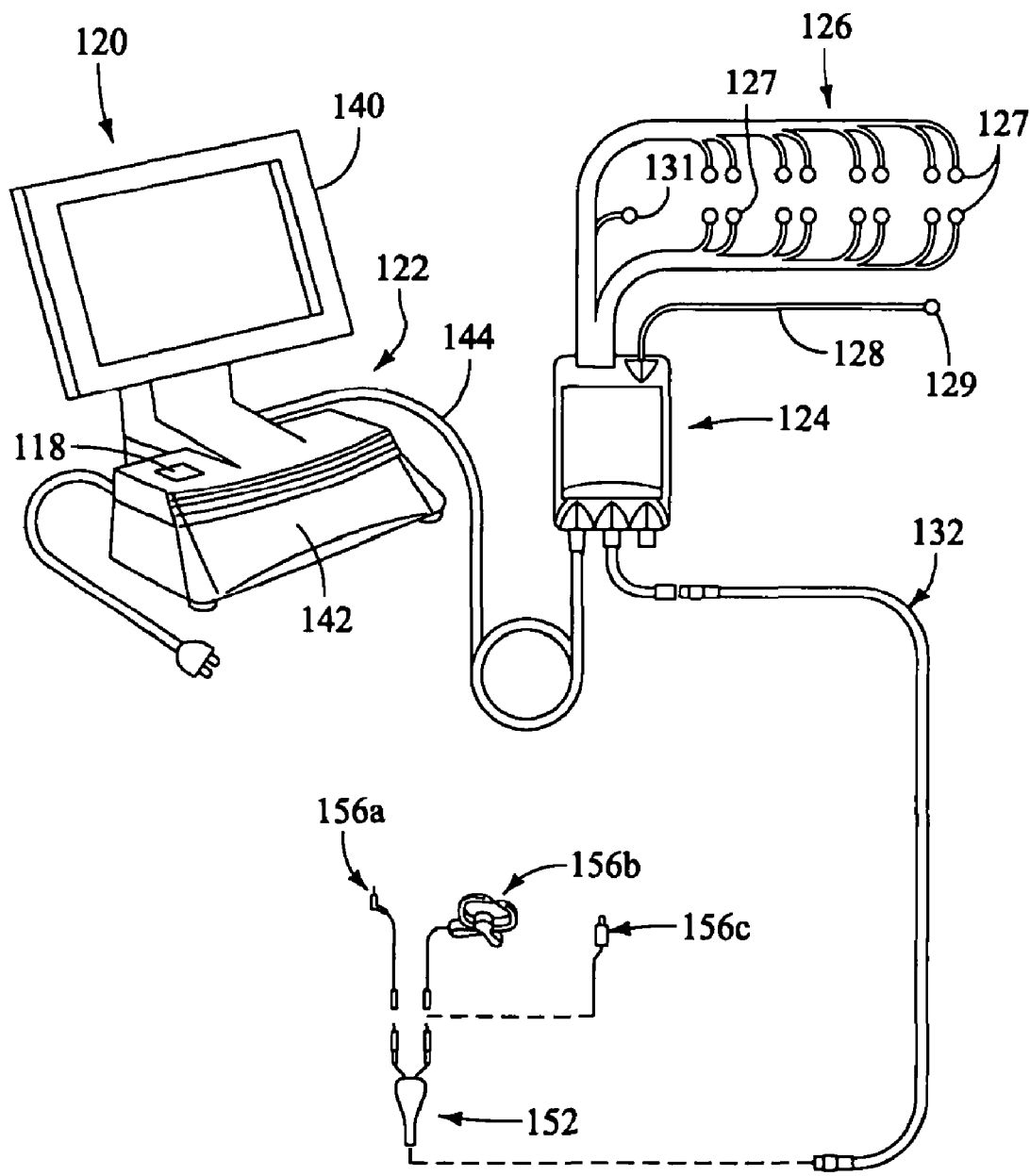
FIG. 19 is a perspective view of an exemplary nerve monitoring system capable of performing nerve monitoring before, during and after the creating of an operative corridor to a surgical target site using the surgical access system in accordance with the present invention.
Figure 20:
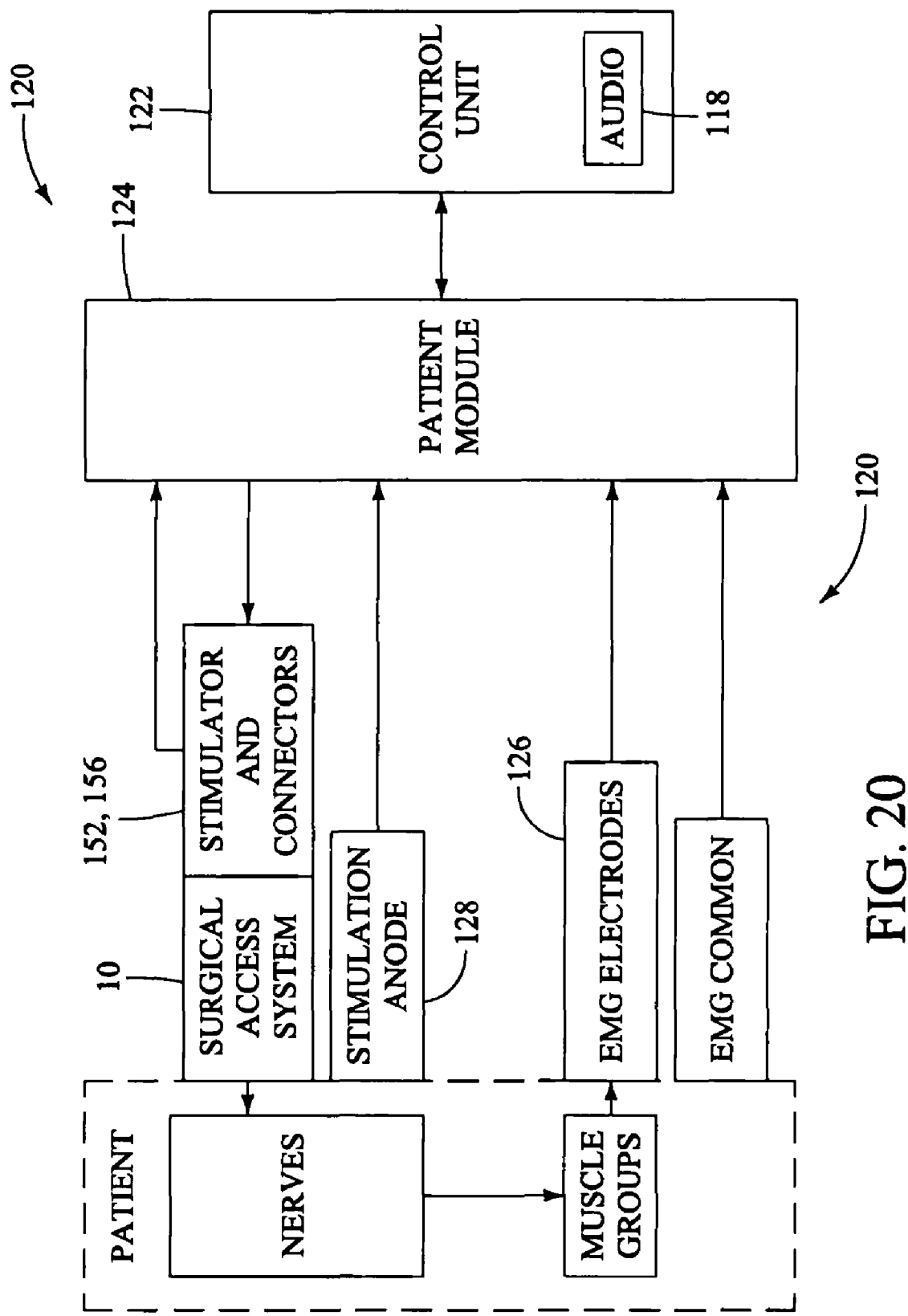
FIG. 20 is a block diagram of the nerve monitoring system shown in FIG. 19.

FIGS. 19-20 illustrate, by way of example only, a monitoring system 120 of the type disclosed in the NeuroVision PCT Applications suitable for use with the surgical access system 10 of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system of the present invention (retractor assembly 10 of FIG. 1 and distraction assemblies 40, 50 of FIGS. 9-12). More specifically, this electrical communication can be achieved by providing, by way of example only, a hand-held stimulation controller 152 capable of selectively providing a stimulation signal (due to the operation of manually operated buttons on the hand-held stimulation controller 152)

to one or more connectors 156a, 156b, 156c. The connectors 156a, 156b, 156c are suitable to establish electrical communication between the hand-held stimulation controller 152 and (by way of example only) the stimulation electrodes on the K-wire 42, the dilators 44, 48, 52, 54, the retractor blades 12, 16, 18 and/or the shim members 22, 24, 25 (collectively "surgical access instruments").

In order to use the monitoring system 120, then, these surgical access instruments must be connected to the connectors 156a, 156b and/or 156c, at which point the user may selectively initiate a stimulation signal (preferably, a current signal) from the control unit 122 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical element with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the K-wire 42, the dilators 44, 48, 52, 54, the retractor blades 12, 16, 18 and/or the shim elements 22, 24, 25 before, during and/or following the creation of an operative corridor to a surgical target site. Monitoring system 120 accomplishes this by having the control unit 122 and patient module 124 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column. For example, one such operative corridor to an intervertebral target site may be established through the retroperitoneal space and the psoas muscle during a substantially lateral, retroperitoneal approach to the lumbar spine, as shown in FIGS. 23-50.

Figure 21:
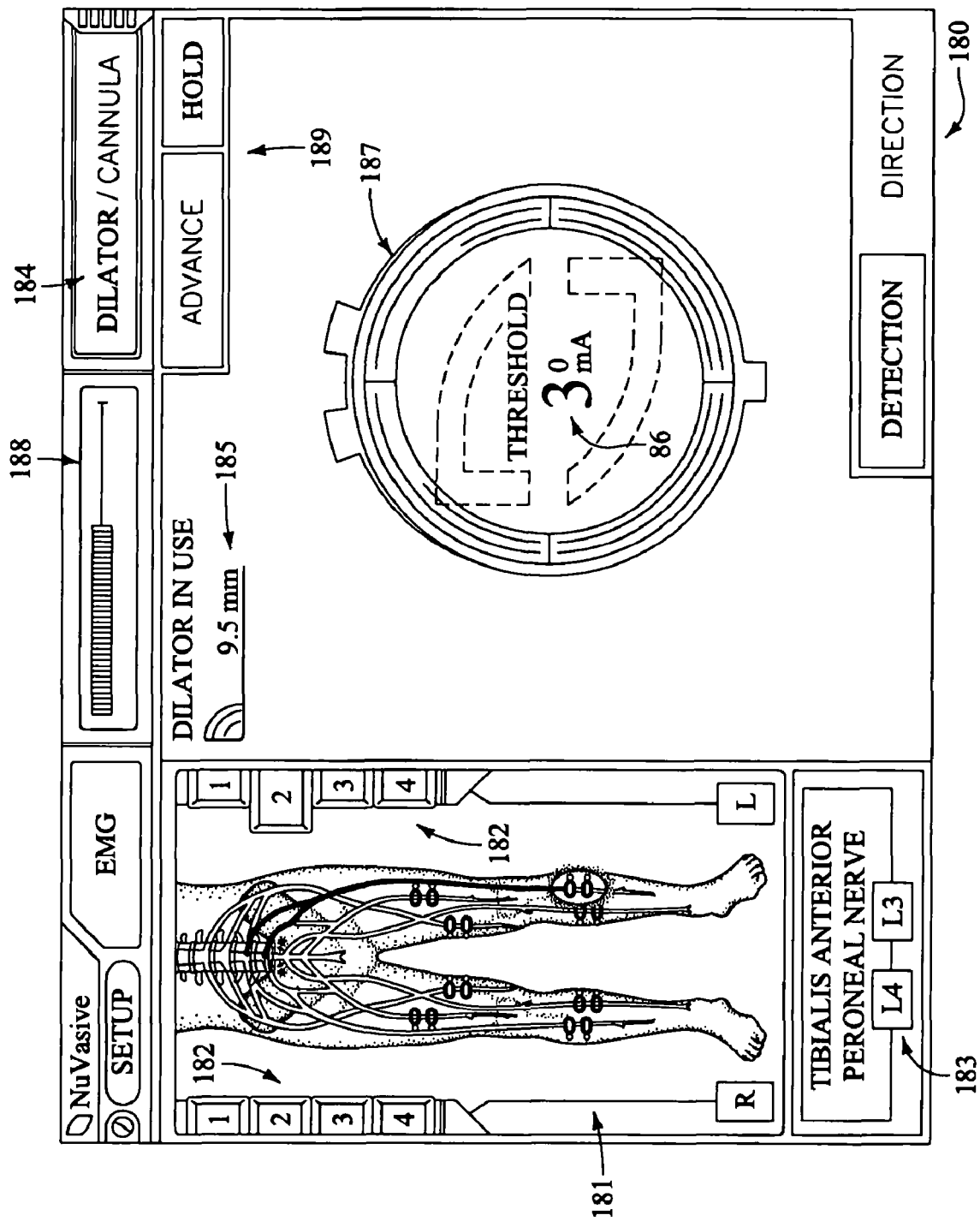
FIGS. 21-22 are screen displays illustrating exemplary features and information communicated to a user during the use of the nerve monitoring system of FIG. 19.
Figure 22:
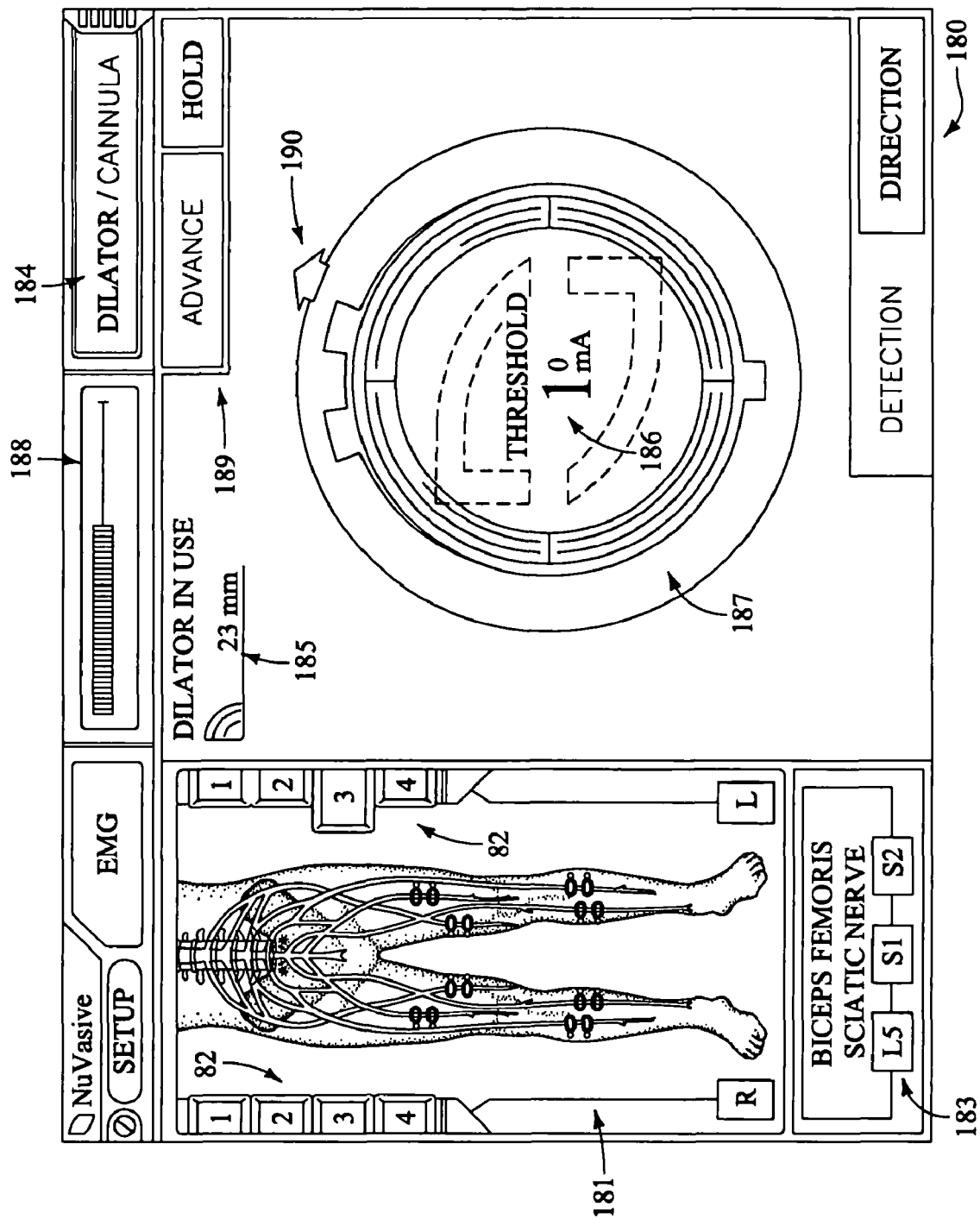

FIGS. 21-22 are exemplary screen displays (to be shown on the display 140) illustrating one embodiment of the nerve direction feature of the monitoring system shown and described with reference to FIGS. 19-20. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (in this case, a dilator 46, 48), the size of the instrument being used 185, the stimulation threshold current 186, a graphical representation of the instrument being used 187 (in this case, a cross-sectional view of a dilator 44, 48) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 22) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various instruments forming the surgical access system 10 of the present invention, including the initial distraction assembly 40 (i.e. the K-wire 42 and dilators 44, 48) and/or the retractor blades 12, 16, 18 and/or the shim elements 22, 24, 25.

Referring now to FIGS. 23-50, some embodiments of the surgical access system 10 may be particularly suited for establishing an operative corridor to a surgical target site in the spine. Such an operative corridor may be established through the retroperitoneal space and the psoas muscle during a direct lateral, retroperitoneal approach to the spine. A surgeon may have direct visualization of the patient's anatomy without the cumbersome requirements associated with using endoscopes or operating coaxial through narrow tubes. Moreover, when using the access system 10 through a lateral approach to the spine, the potential of damaging nerves while advancing instruments through the psoas muscle may be substantially reduced. It will, of course, be appreciated that the surgical access system and related methods of the present invention may find applicability in any of a variety of surgical and/or medical applications such that the following description relative to the direct lateral, retroperitoneal approach to the spine is not to be limiting of the overall scope of the present invention.

When accessing a spinal target site via the substantially lateral, retroperitoneal approach described in connection with FIGS. 23-50, the surgeon should consider several anatomical reference points, such as the iliac crest, the twelfth rib, and the lateral border of the erector spinae muscle groups. In certain embodiments, blunt finger dissection is used to pass between these muscle groups and access the retroperitoneal space. Such a technique offers simple access to the retroperitoneal space while minimizing the potential of visceral lesion. Furthermore, in such embodiments, the finger may be used to escort one or more dilators through the retroperitoneal space, thus reducing the potential of peritoneal disruption. In some instances, each dilator is preferably advanced through the psoas muscle between the middle and anterior third of the muscle so that the nerves of the lumbar plexus are located posterior and outside the operative corridor. A monitoring system 120 of the type disclosed in the NeuroVision PCT Applications may be used to avoid damage to any peripheral nerves embedded throughout the psoas muscle as the dilator is advanced through the muscle to the surgical target site in the spine.

Figure 23:
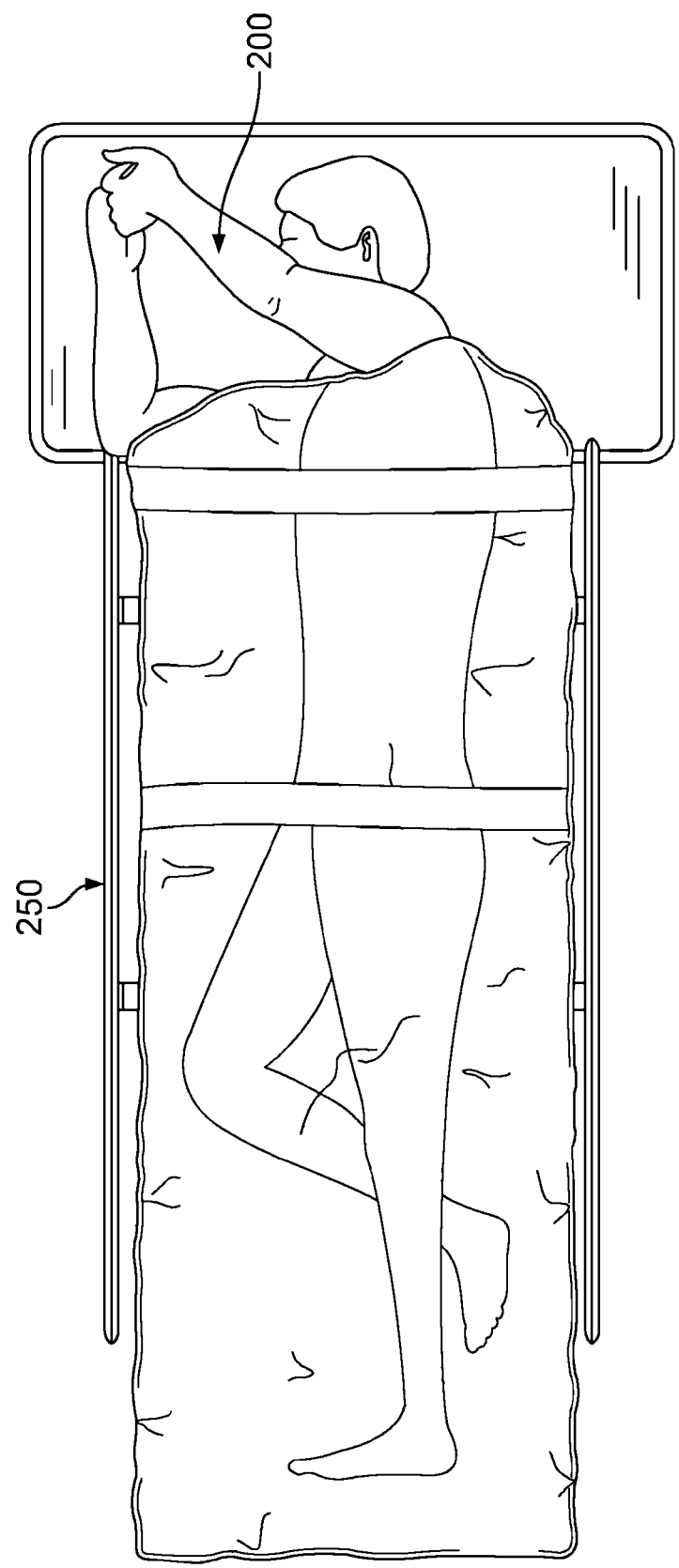
FIGS. 23-50 illustrate a method for accessing a surgical target site in the spine using a substantially lateral, retroperitoneal approach.
Figure 24:
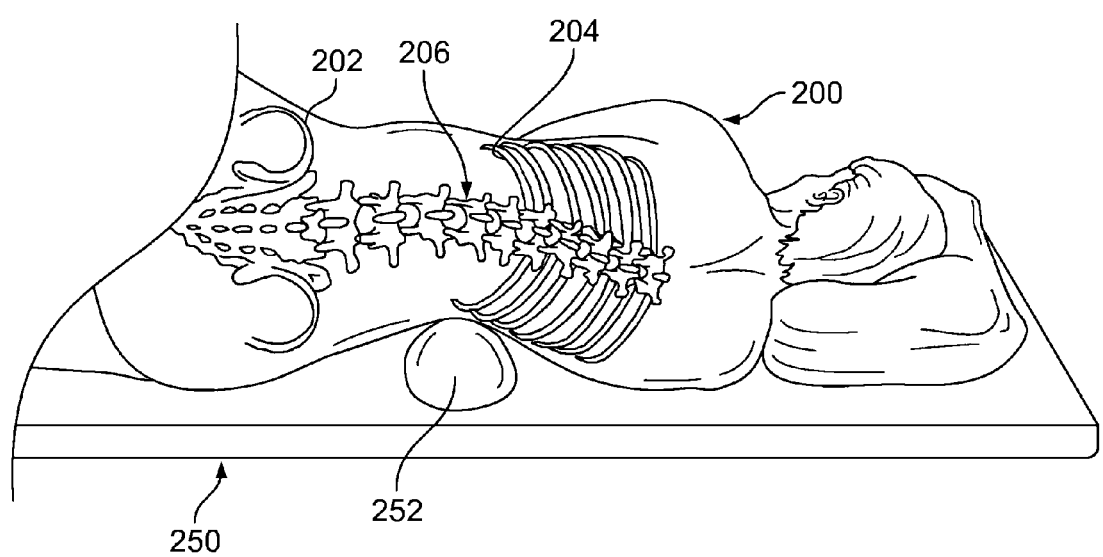

Referring now to FIGS. 23-24, a patient 200 is positioned on a surgical table 250 in preparation of spinal surgery. In some embodiments, a cushion 252 is positioned between the patient's lateral side and the surgical table 250 to arrange the patient 200 in such a way as to increase the distance between the patient's iliac crest 202 and rib cage 204. Alternatively, a flexion of the surgical table 250 may be used to accomplish the desired arrangement. Such an arrangement helps to open the invertebral disc space 206 at or near the surgical target site.

Figure 25:
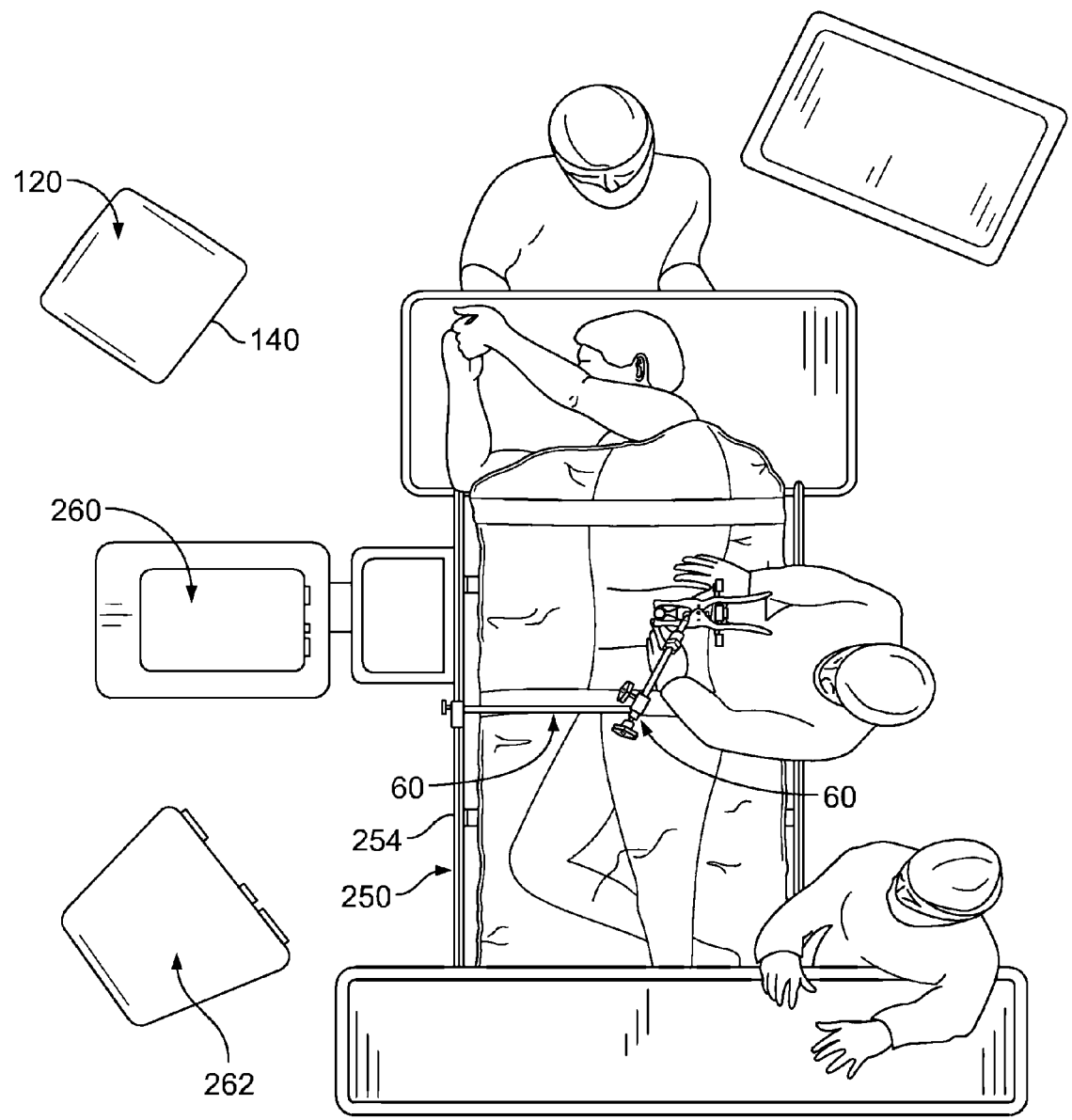

Referring to FIG. 25, an articulating arm assembly 60 is coupled to the surgical table 250 to maintain the access system 10 in a substantially fixed position relative to the surgical target site when the operative corridor has been established. In this embodiment, the articulating arm assembly 60 is mounted to a bedrail 254 of the surgical table 250. In some instances, a fluoroscopy system 260 is disposed proximal to the surgical table 250 to provide the surgeon with visualization of the surgical target area. This fluoroscopy system 260 includes a display monitor 262 that is positioned such that the surgeon may view the monitor 262 during the operation. In addition, a monitoring system 120 of the type disclosed in the NeuroVision PCT Applications may be positioned near the surgical table 250 so that the surgeon may view a display 140 of the monitoring system 120 during the operation.

Figure 26:
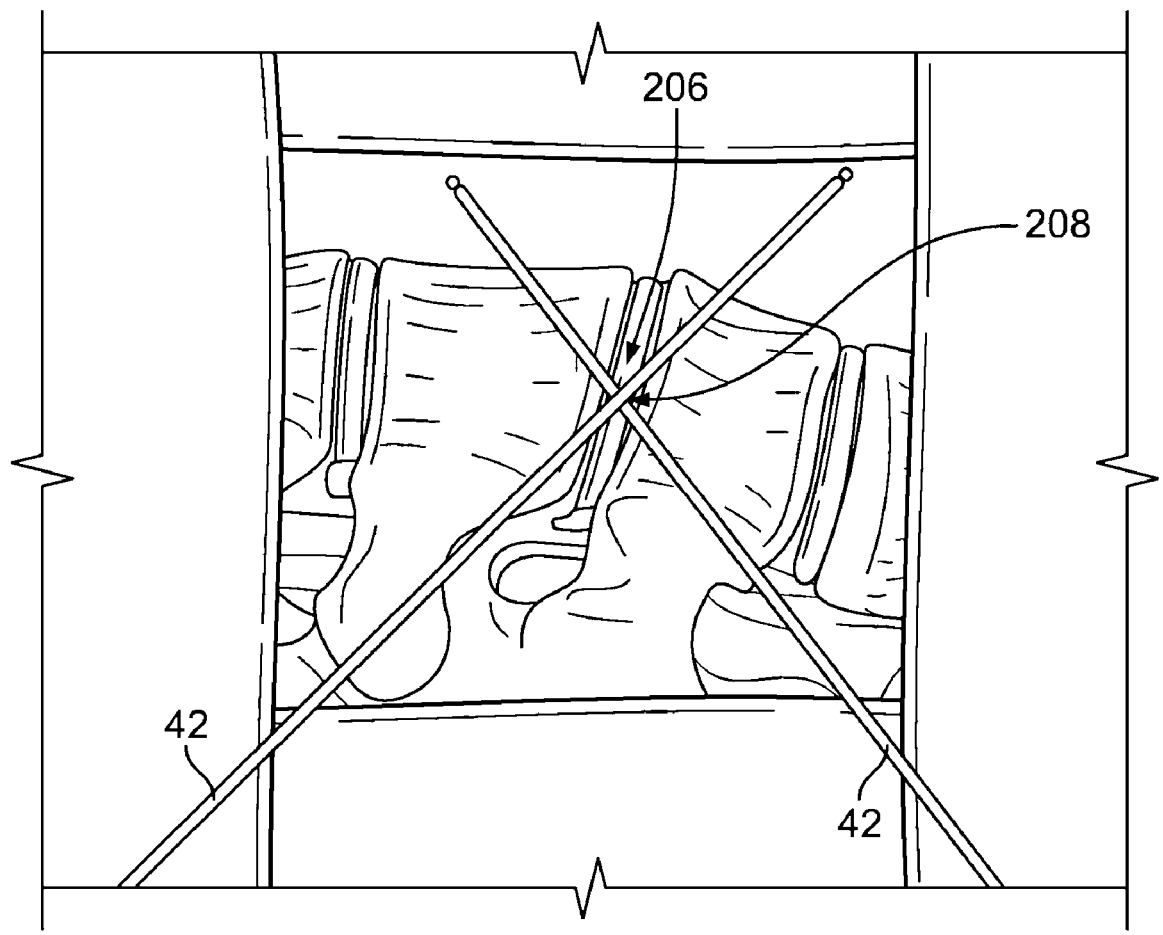
Figure 27:
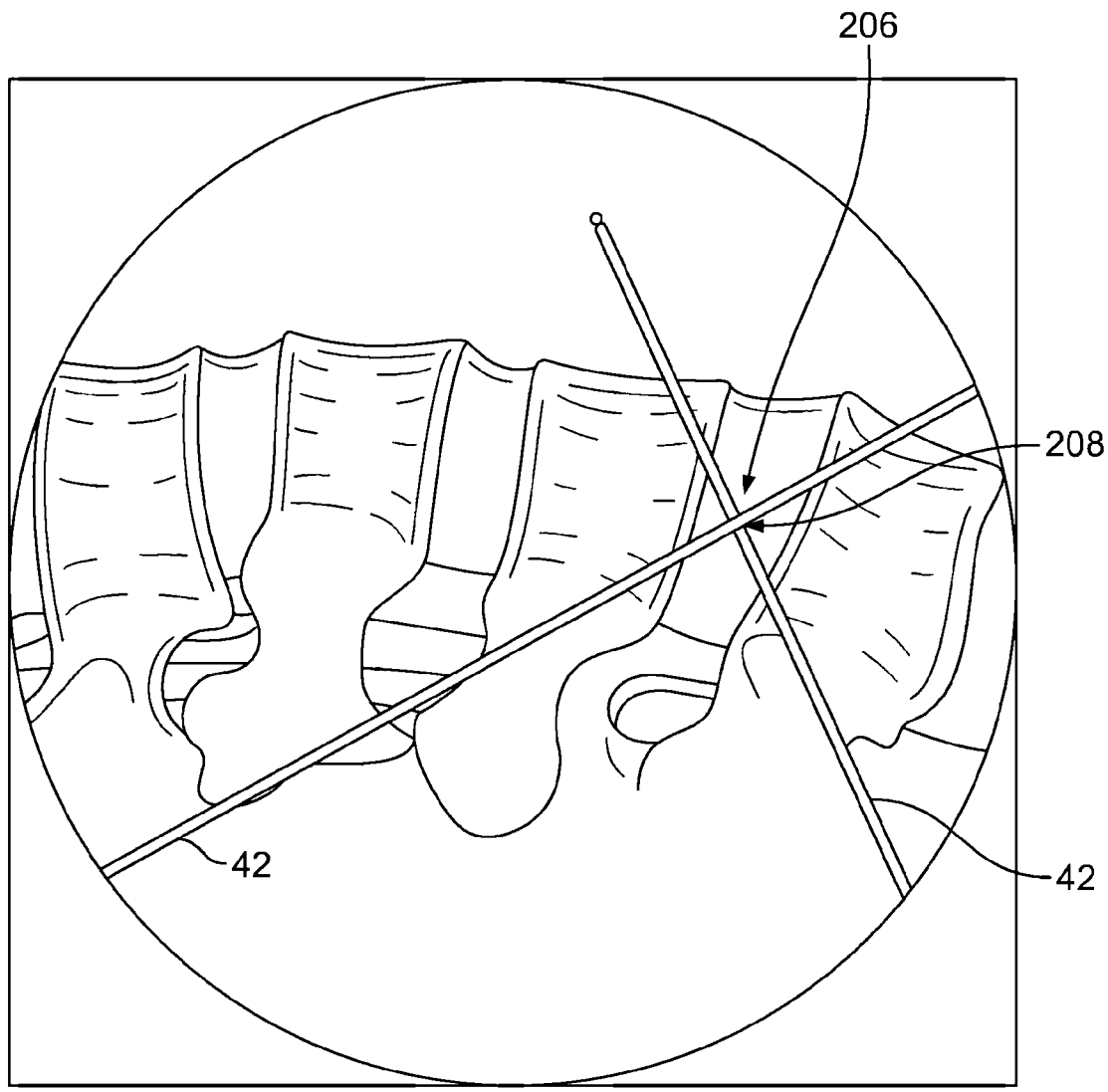
Figure 28:
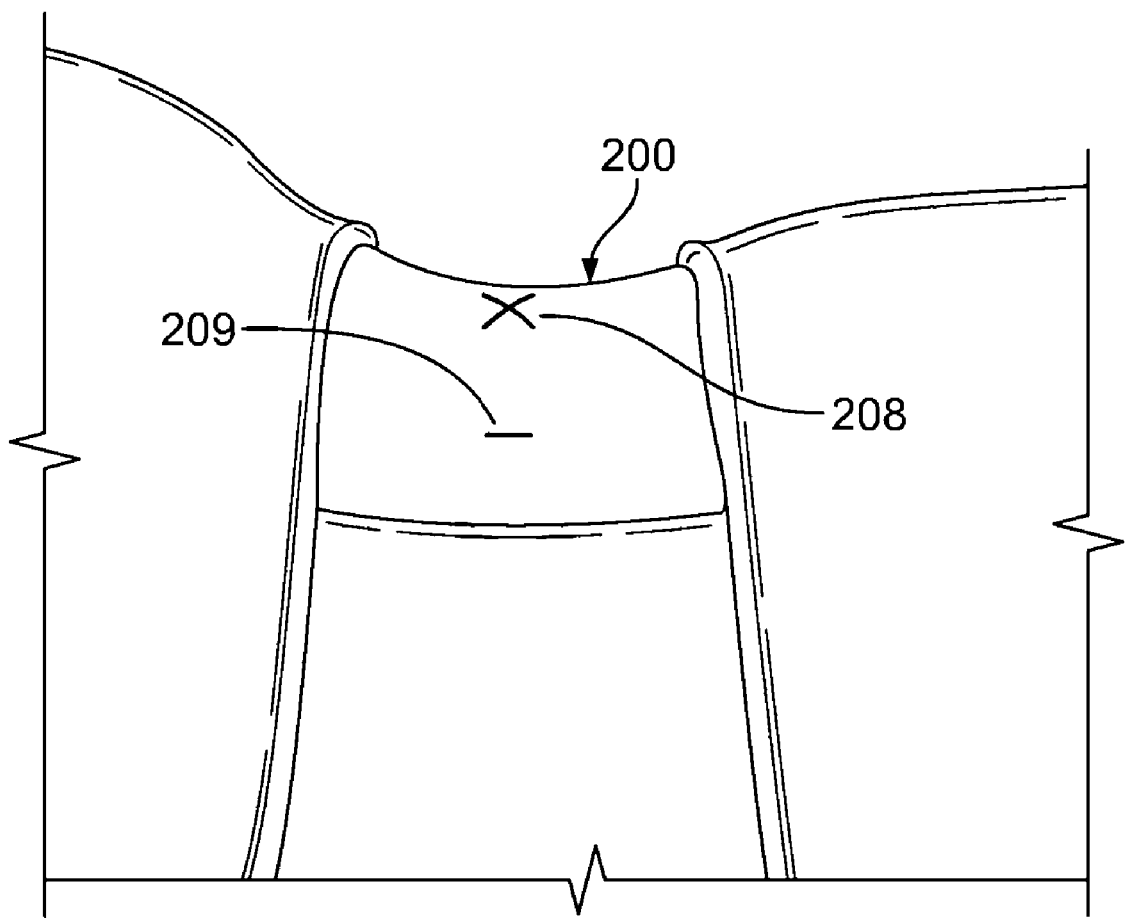

Referring now to FIGS. 26-28, one or more instruments, such as K-wires 42, are positioned laterally over an area of the patient 200 and then viewed using the lateral fluoroscopy. The instruments are used to identify a lateral incision location 208 that is substantially lateral to the surgical target site (e.g., the invertebral disc space 206). As shown in FIG. 28, a first mark is made on the patient 200 at the lateral incision location 208. In addition, a second mark is made on the patient at a posteriolateral incision location 209 near the lateral incision location 208. In this embodiment, the posteriolateral incision location 209 is approximately at the lateral border of the erector spine muscle. Preferably, the posteriolateral incision location 209 is within a finger's length of the lateral incision location 208.

Figure 29:
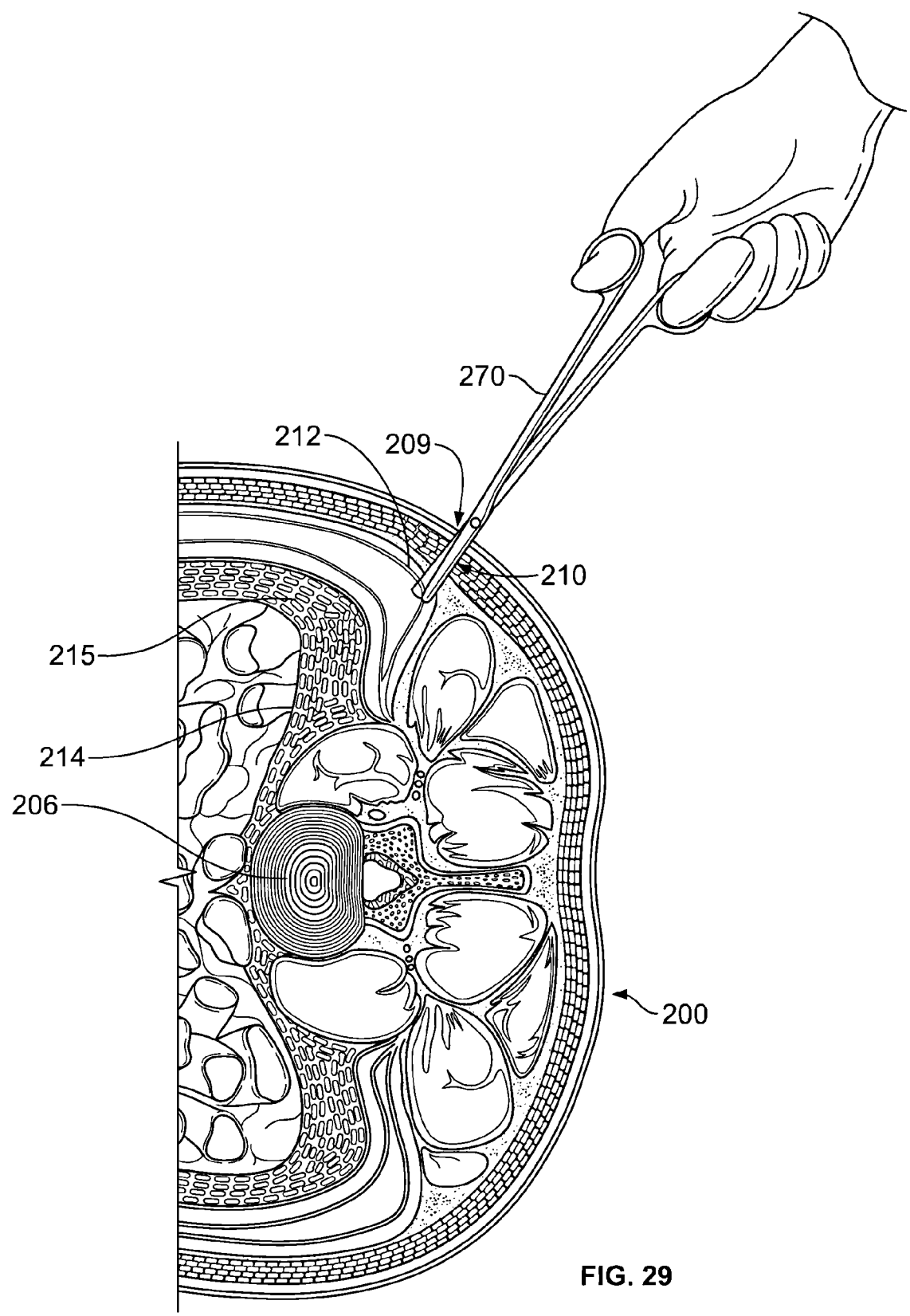

Referring to FIG. 29, an incision is made at the posteriolateral incision location 209, and the subcutaneous layers 210 are dissected until reaching the muscular masses 212. A dissection instrument, such as blunt dissection scissors 270, is used to spread the muscle fibers 212 until the retroperitoneal space 215 is reached. Preferably, the surgeon uses great caution to avoid perforation of the peritoneum 214.

Figure 30:
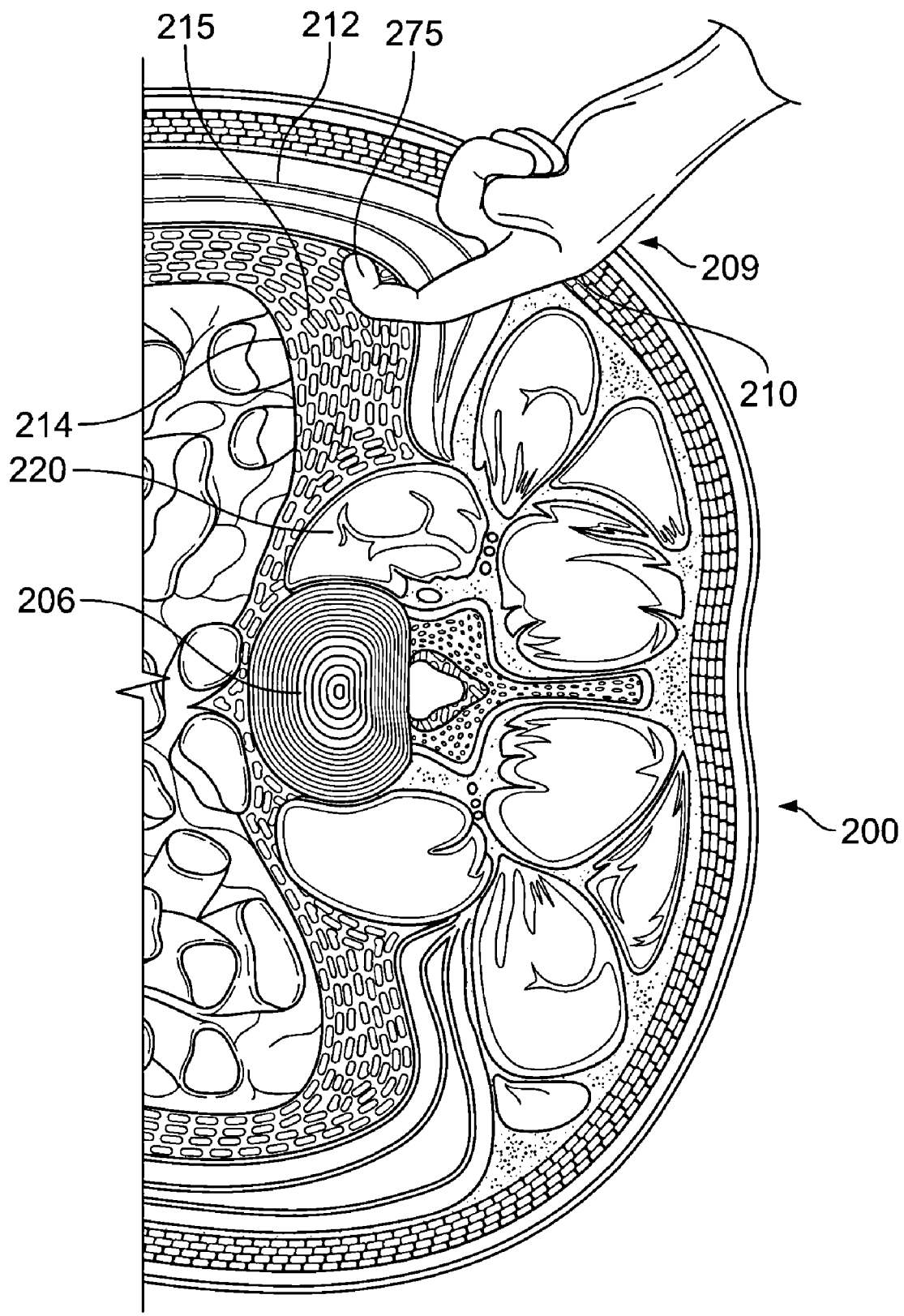
Figure 31:
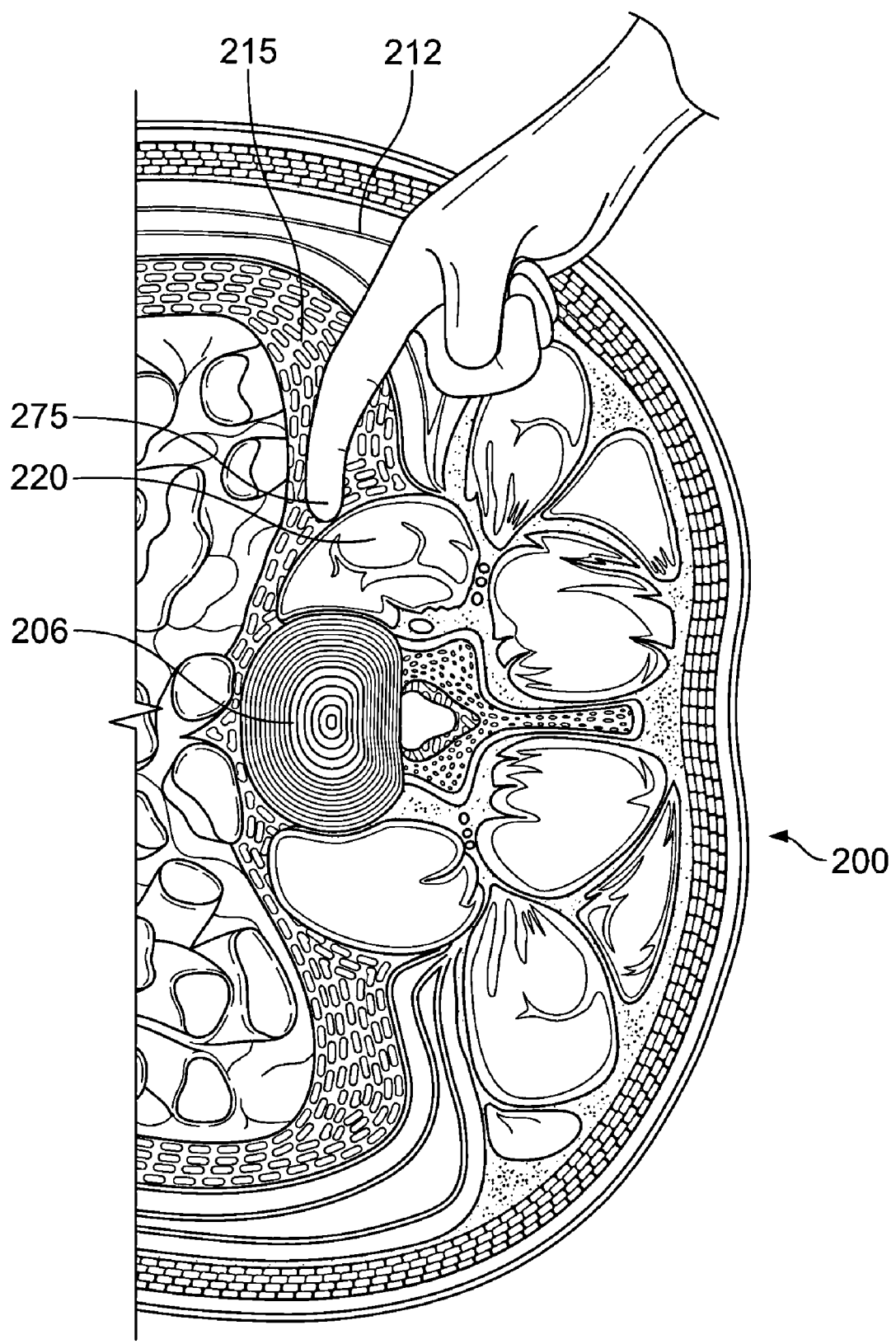

Referring to FIGS. 30-31, after the retroperitoneal space 215 is reached, a guide member 275 is inserted through the posteriolateral incision 209 into the retroperitoneal space 215. In a presently preferred embodiment, the guide member is a finger 275 of the surgeon, which is preferably covered with a surgical glove for hygienic purposes. In other embodiments, the guide member 275 may be an instrument or tool configured to extend and maneuver in the retroperitoneal space as described herein. As shown in FIGS. 30-31, the finger 275 may sweep a portion of the retroperitoneal space 215 and then palpate down to the psoas muscle 220. This motion of the finger 275 in the retroperitoneal space 215 may loosen some fatty tissue before a dilator is advanced therethrough.

Figure 32:
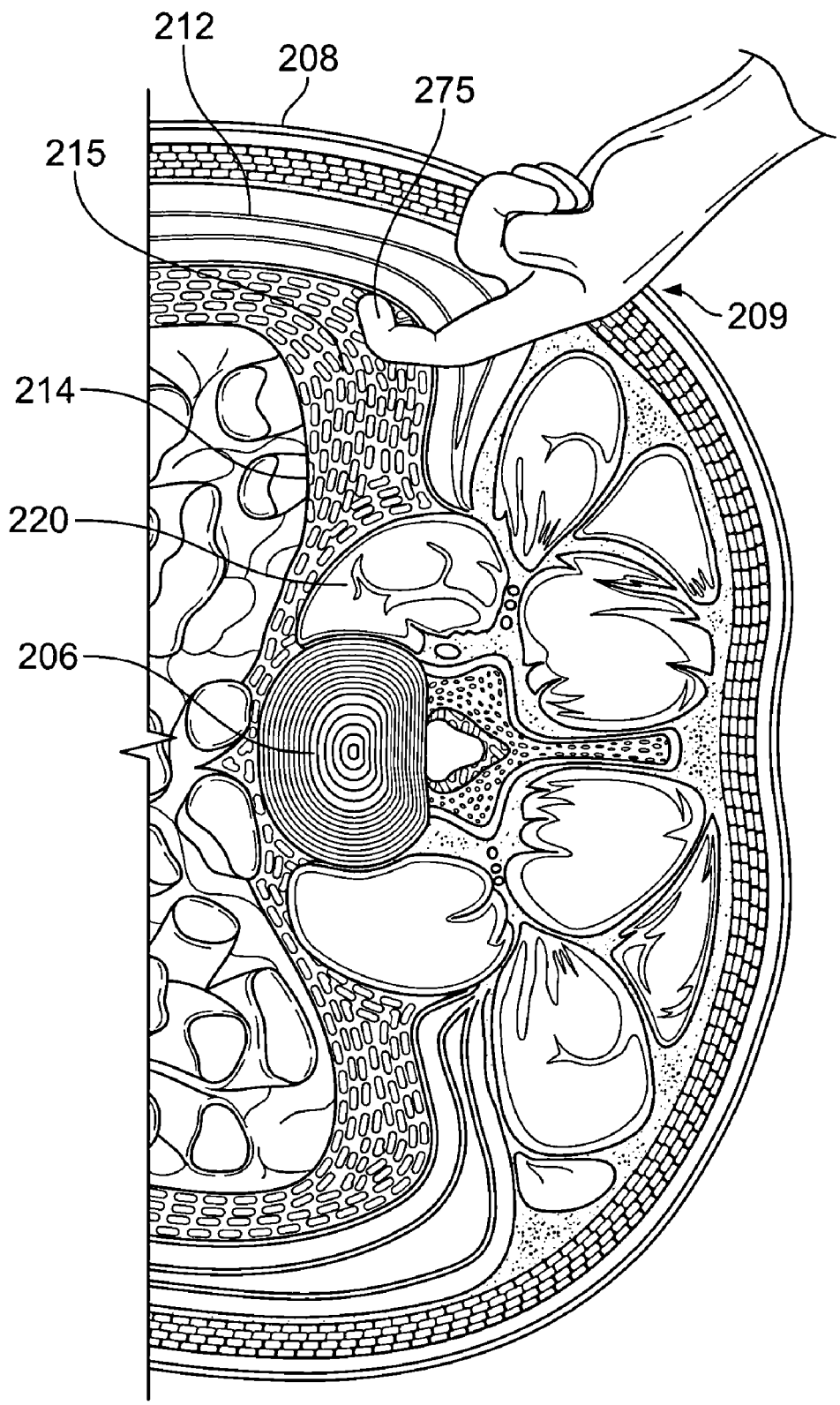
Figure 33:
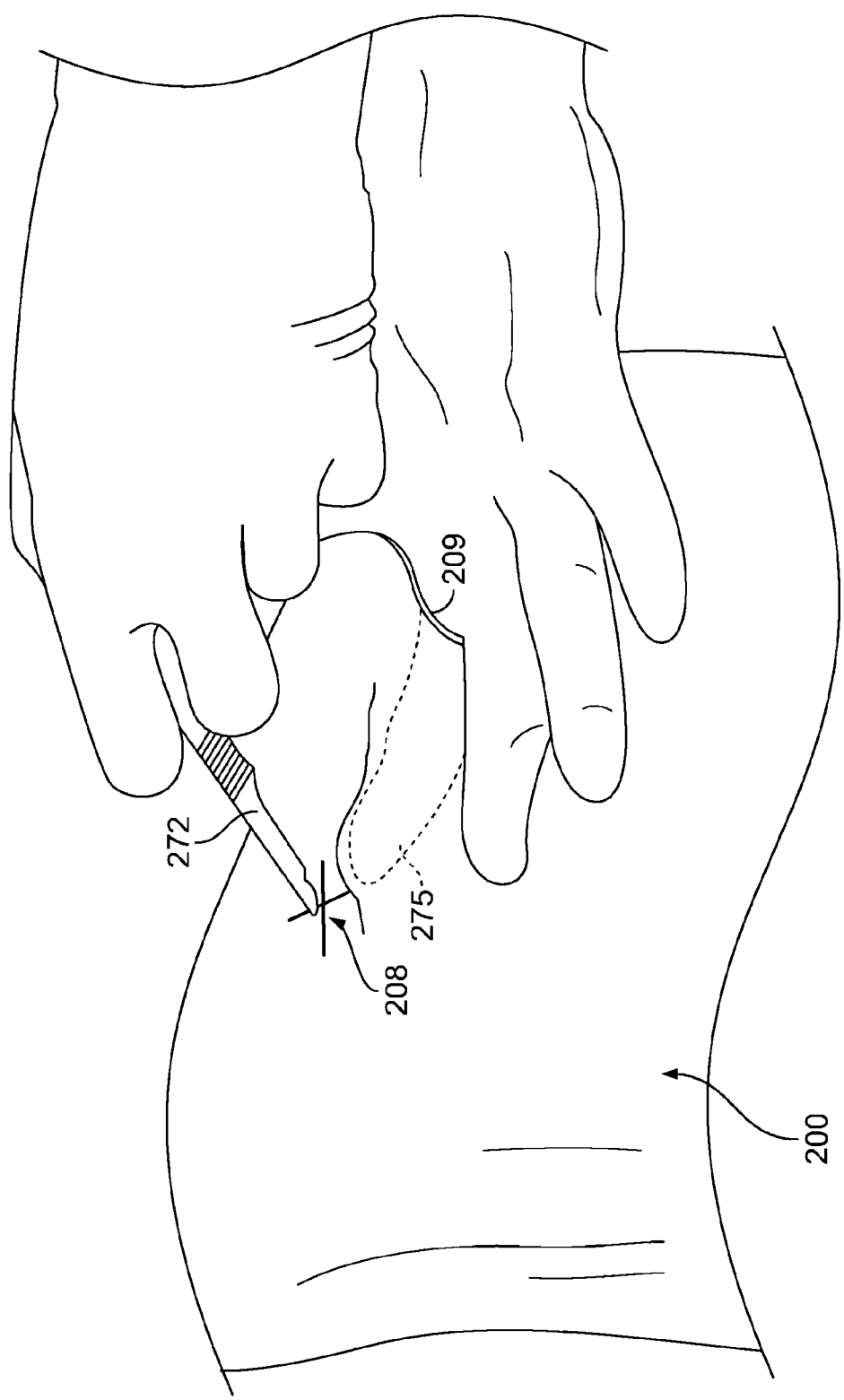

Referring to FIGS. 32-33, after the psoas muscle 220 is identified, the finger 275 is swept away from the psoas muscle 220 toward the lateral incision location 208. A scalpel 272 or other like instrument is used to make and incision at this location 208. The incision should be of a sufficient size to receive a distal end 41 an initial dilator 40.

Figure 34:
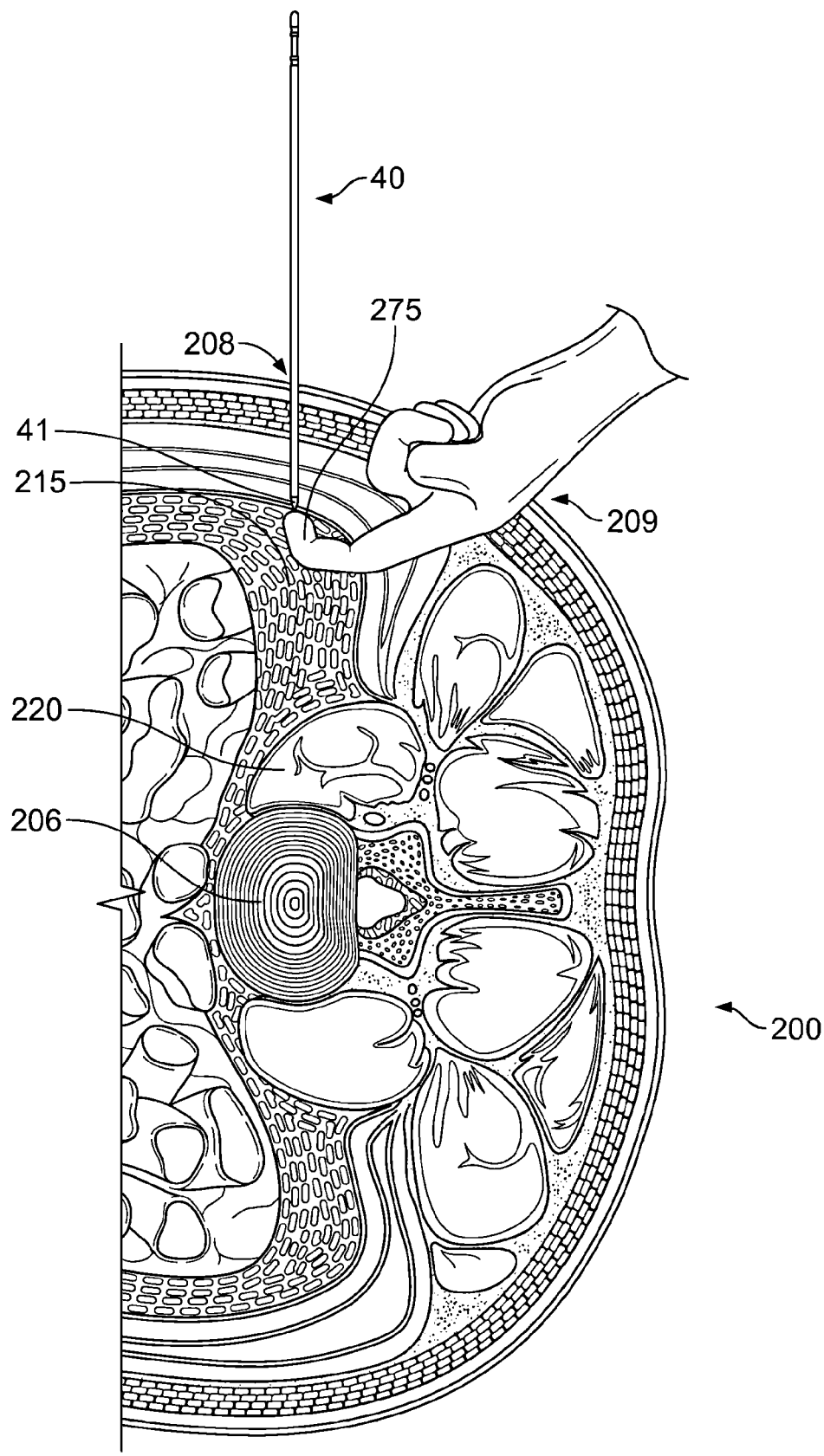
Figure 35:
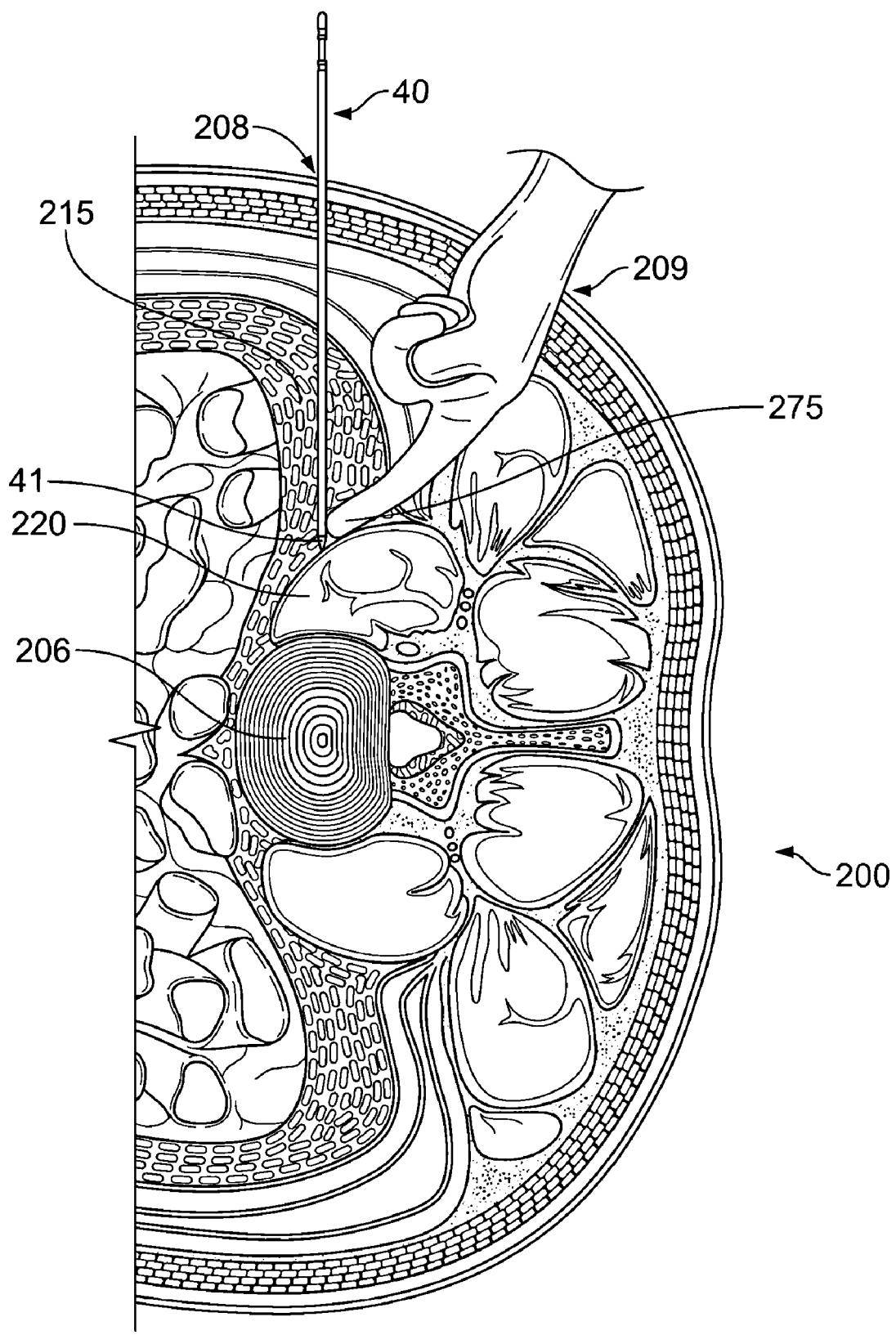

Referring to FIGS. 34-35, the finger 275 is used to direct the distal end 41 of the initial dilator 40 through the retroperitoneal space 215 toward the psoas muscle 220. In the presently preferred embodiment, the initial dilator 40 includes at least a K-wire 42 and may also include a split-dilator 48 slideably passed over the K-wire 42 (see, for example, FIG. 10). As shown in FIG. 34, the distal end 41 is introduced through the lateral incision location 208 and directed to the finger 275 in the retroperitoneal space 215. As shown in FIG. 35, the finger 275 engages the initial dilator 40 proximal to the distal end 41 and guides the distal end 41 to the psoas muscle 220. By escorting the dilator 40 through the retroperitoneal space 215 using the finger 275, the potential for breaching or disrupting the peritoneal is reduced. Upon reaching the psoas muscle 220, the location of the distal end 41 relative to the target site may be verified using an imaging system, such as an image intensifier.

Figure 36:
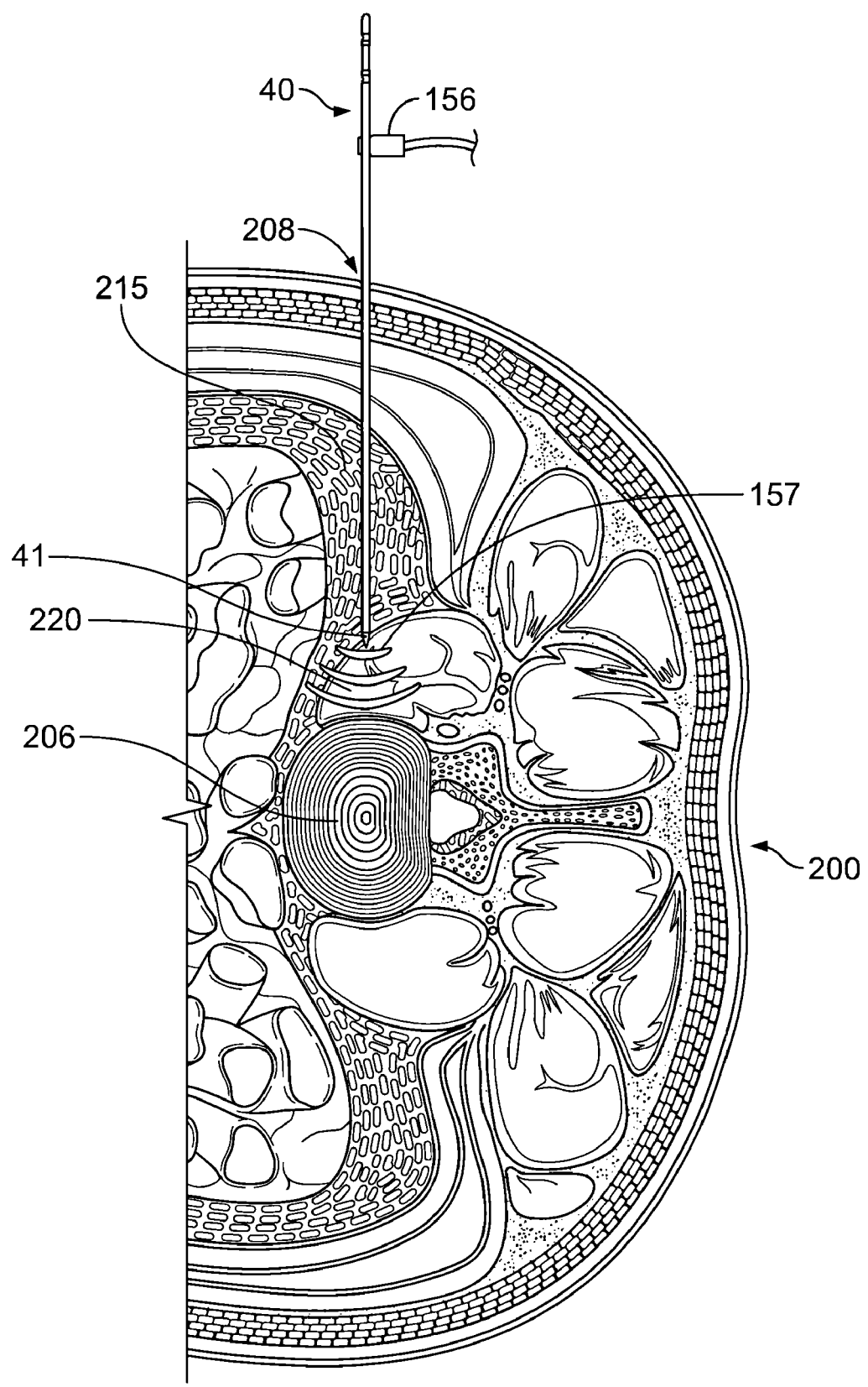
Figure 37:
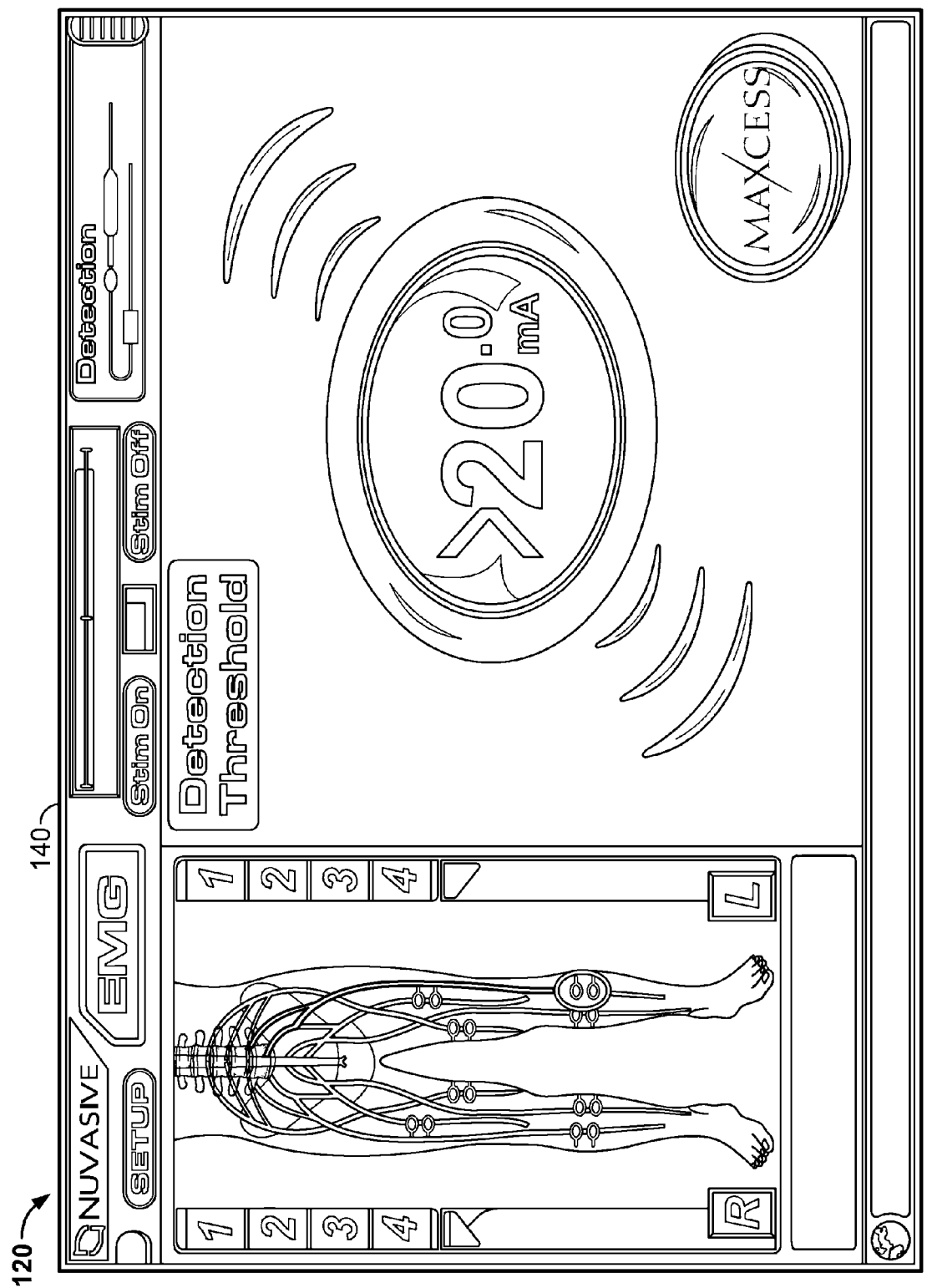

Referring to FIGS. 36-37, the distal end 41 of the initial dilator 40 is advanced in a substantially lateral direction through the psoas muscle 220 toward the invertebral disc space 206 at or near the surgical target site. In the presently preferred embodiment, the fibers of the psoas muscle 220 are split using blunt dissection and NeuroVision neurophysiologic monitoring of the type disclosed in the NeuroVision PCT Applications. A stimulation connector 156 of the NeuroVision monitoring system 120 (see FIG. 19) is coupled to the initial dilator 40 to provide a stimulation signal 157 as the dilator 40 is advanced through the psoas muscle 220. It should be understood that the stimulation signal 157 is depicted in FIG. 36 for illustrative purposes and is generally not visible.

Descending nerves of the lumbar plexus normally lie in the posterior one-third of the psoas muscle 220. The NeuroVision monitoring system 120 of the type disclosed in the NeuroVision PCT Applications assists with the safe passage by these nerves and/or confirmation of the nerves' posterior location. The NeuroVision monitoring system 120 will continuously search for the stimulus threshold that elicits an EMG response on the myotomes monitored and then reports such thresholds on a display 140 as shown in FIG. 37. As the dilator is advanced through the psoas muscle 220, the stimulus necessary to elicit an EMG response will vary with distance from the nerve. In the presently preferred embodiment, experience has shown that threshold values greater than 10 mA indicate a distance that allows for safe passage through the psoas muscle 220 and continued nerve safety.

Figure 38:
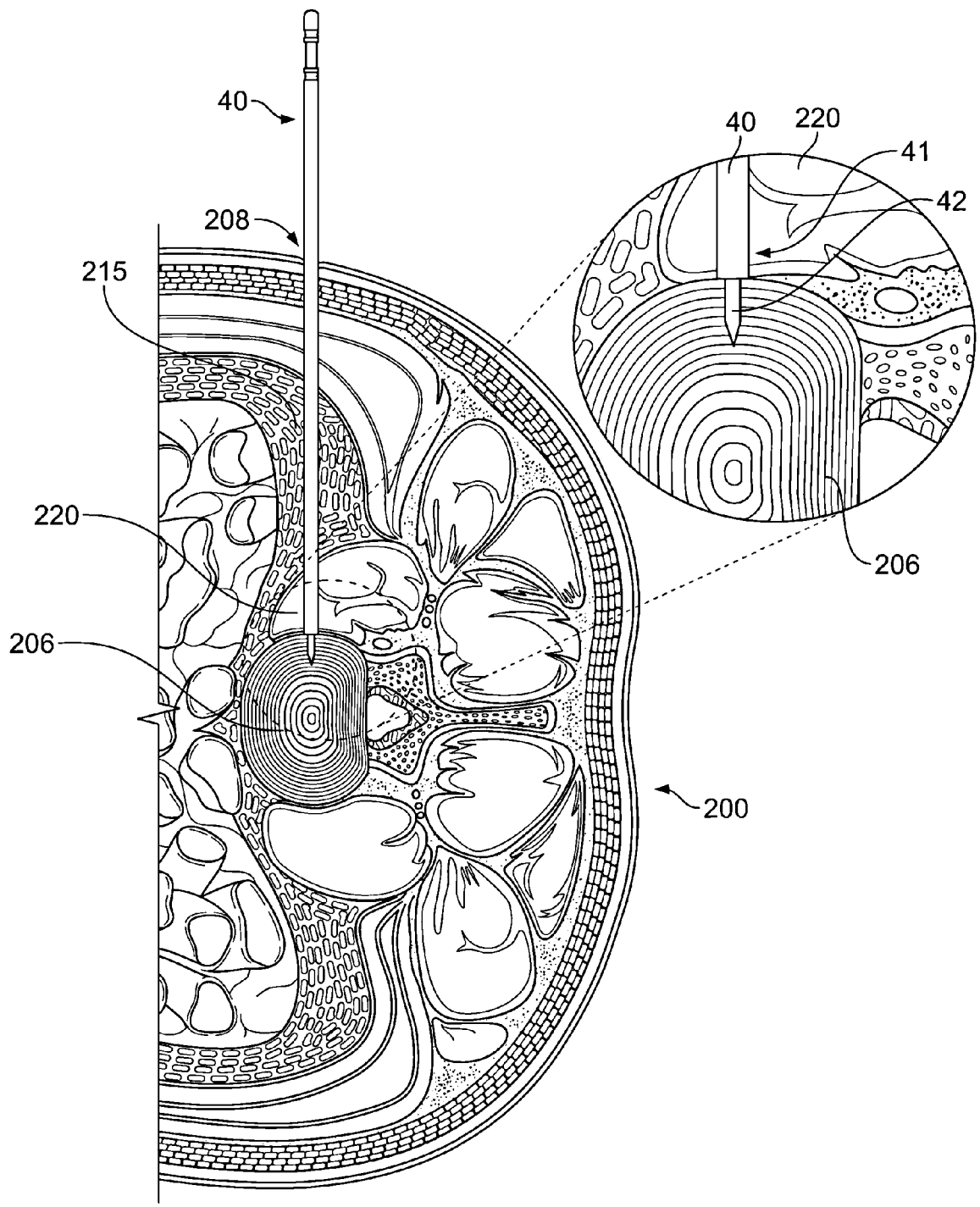
Figure 39:
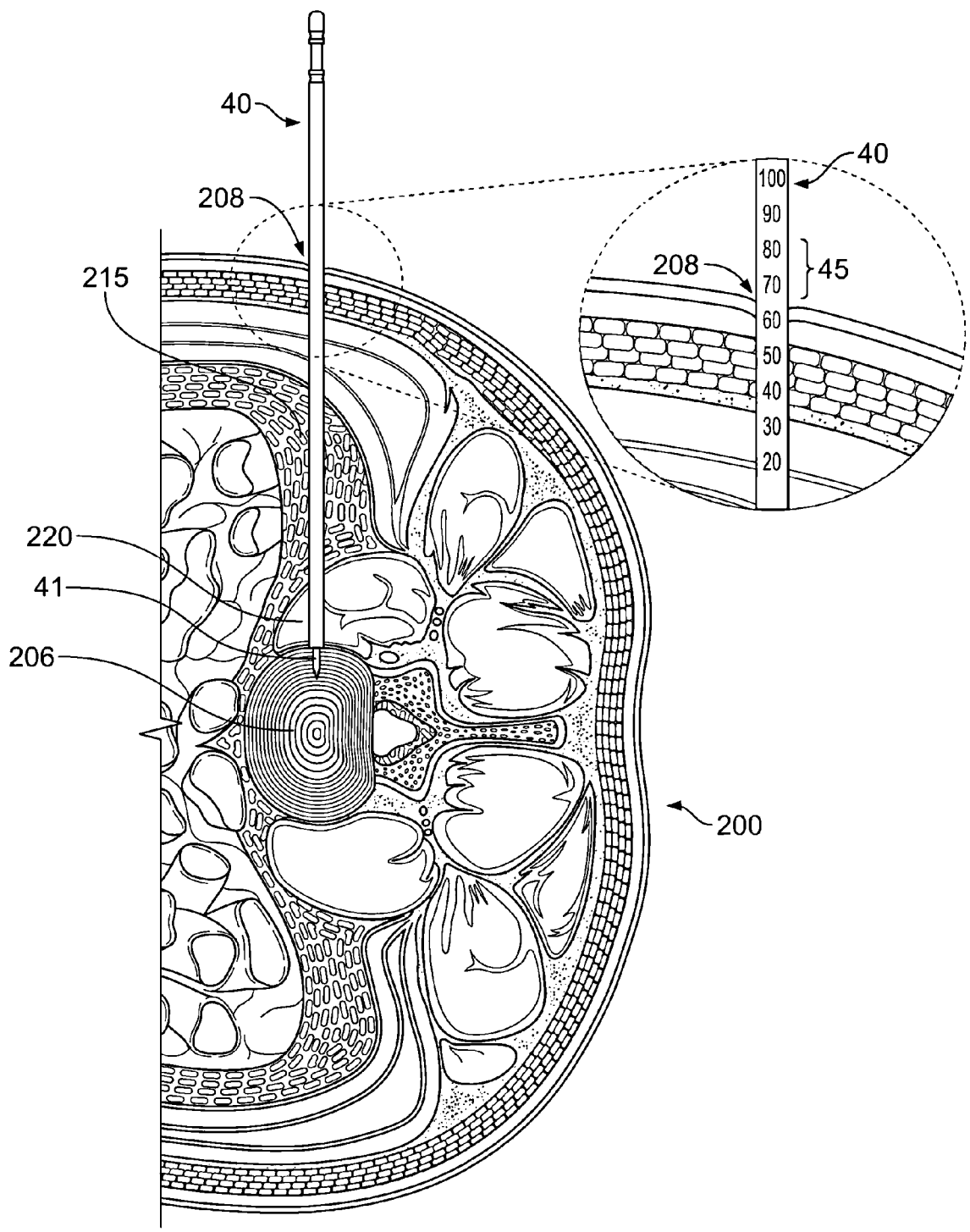
Figure 40:
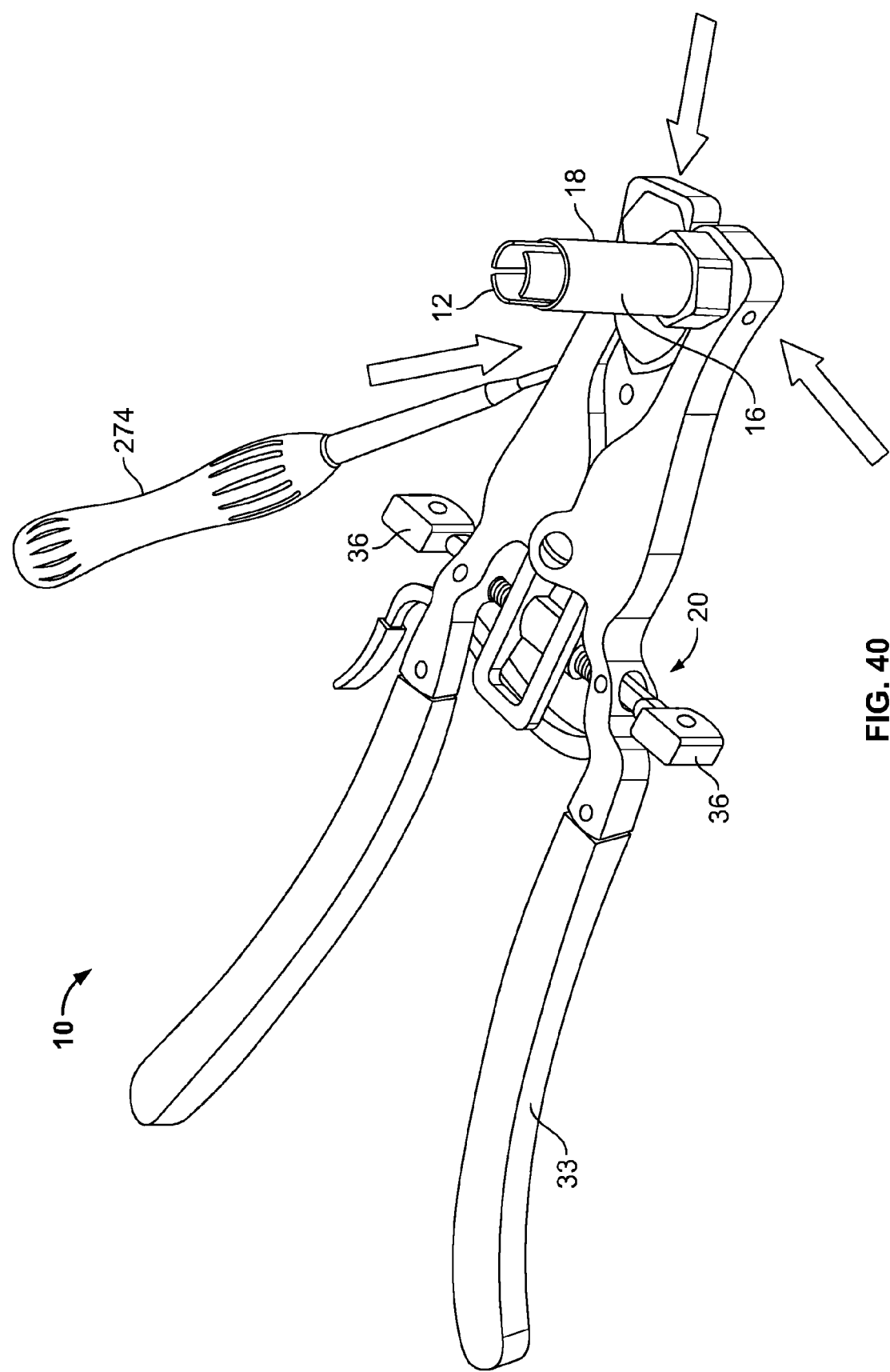

Referring to FIGS. 38-40, a K-wire 42 of the initial dilator 40 is introduced into the targeted disc space 206 after the dilator 40 is passed through the psoas muscle 220. Preferably, the position of the distal end 41 of the dilator 40 is confirmed using fluoroscopic imaging before the K-wire 42 is introduced into the disc space 206. After a distal portion of the K-wire 42 is inserted into the targeted disc space 206, depth markings 45 (FIG. 39) on the dilator 40 may be read at the skin level to determine the appropriate length of retractor blades 12, 16, 18 that will be used with the handle assembly 20 of the access system 10. As shown in FIG. 40, the appropriate length blades 12, 16, and 18 may be secured to the handle portion 20 by tightening fasteners with a driver instrument 274.

Figure 41:
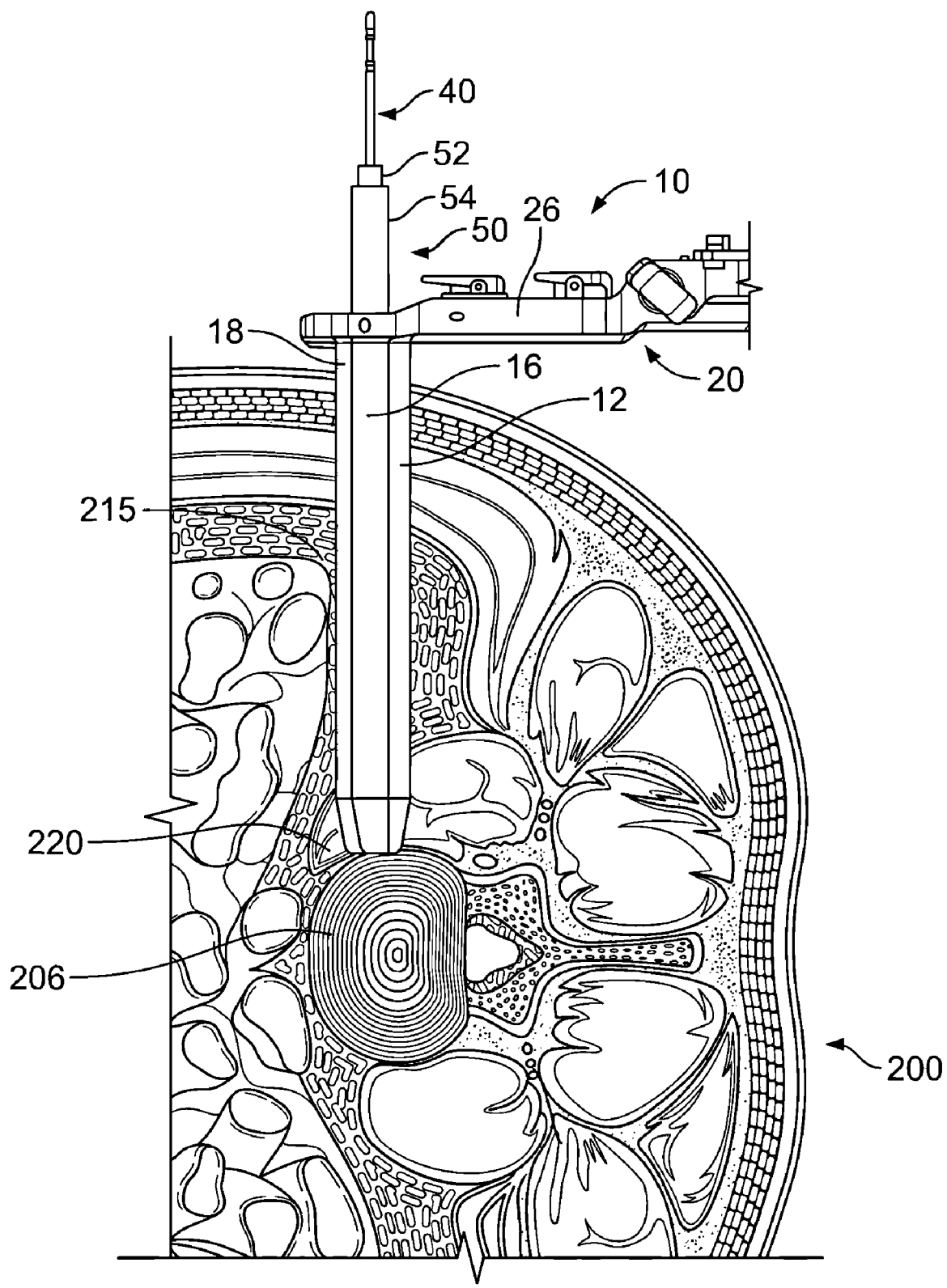

Referring to FIG. 41, the sequential dilation system 50 (previously described in connection with FIG. 12), including one or more supplemental dilators 52, 54, may be guided over the initial dilator 40 for the purpose of further dilating the tissue down to the surgical target site. In the presently preferred embodiment, the NeuroVision monitoring system 120 of the type disclosed in the NeuroVision PCT Applications is used with the supplemental dilators 52, 54 to provide safe passage through the psoas muscle 220. The initial dilator 40 and the supplemental dilators 52, 54 are advanced through the lateral incision location 208 to the targeted disc space 206 in a substantially lateral direction to create a distraction corridor.

Still referring to FIG. 41, the retractor blades 12, 16, 18 of the access system 10 are introduced over the supplemental dilator 54 (or the initial dilator 40 if the sequential dilation system 50 is not employed) toward the disc space 206; Again, the NeuroVision monitoring system 120 of the type disclosed in the NeuroVision PCT Applications may be used with the blades 12, 16, 18 to provide safe passage through the psoas muscle 220. In some embodiments, the posterior shim element 22 and/or the retractor extenders 24, 25 are engaged with the retractor blades 12, 16, 18 (as previously described in connection with FIGS. 1-7). After the retractor blades 12, 16, 18 are introduced along the distraction corridor, fluoroscopic imaging may be used to confirm the position of the blades 12, 16, 18 proximal to the disc space 206.

Figure 42:
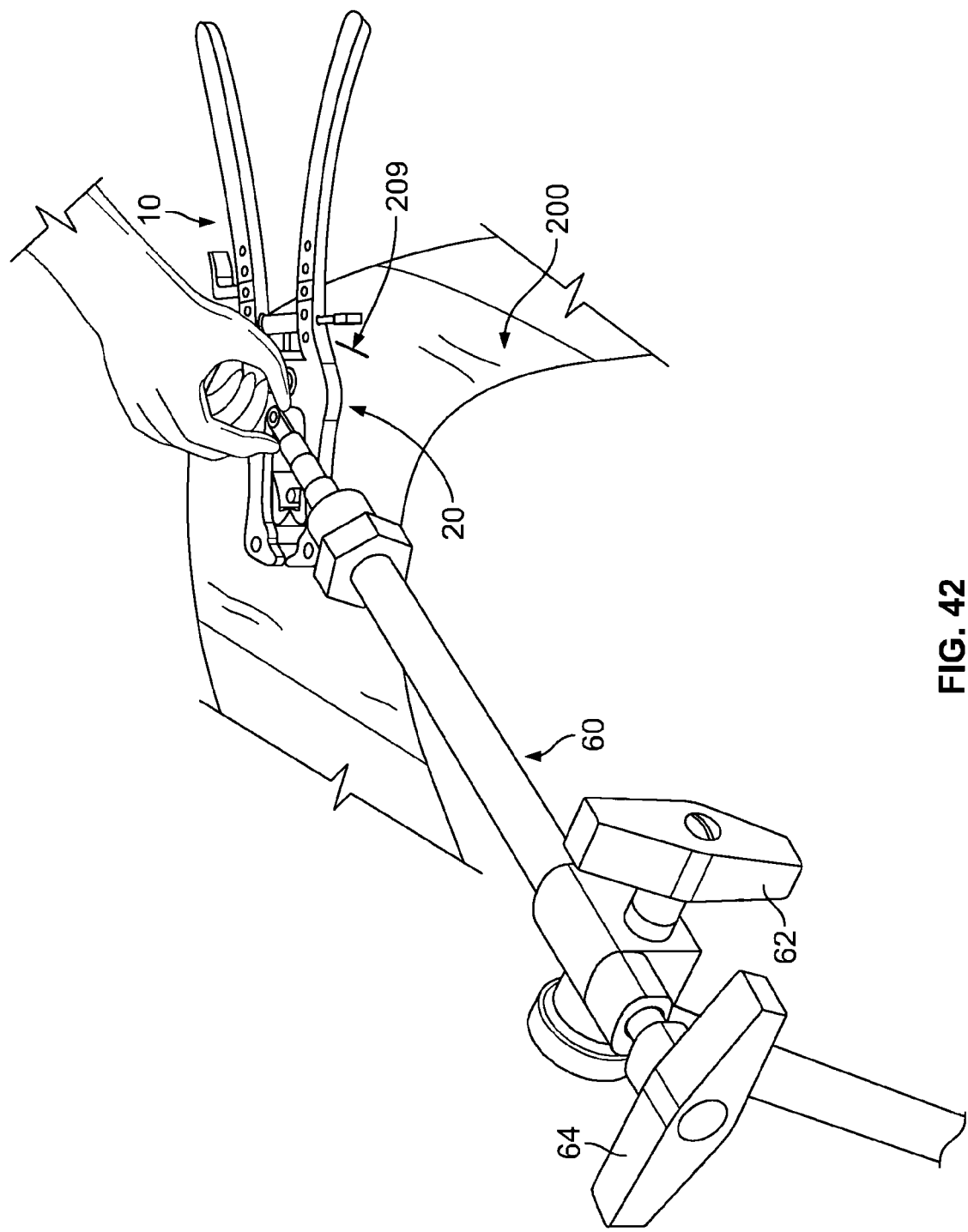

Referring to FIG. 42, the articulating arm assembly 60 is coupled to the handle member 20 of the access system 10. As previous described in connection with FIG. 25, the articulating arm assembly 60 is also coupled to the surgical table 250 so as to maintain the access system 10 in a substantially fixed position. Handles 62 and 64 may be turned to substantially fix the position of articulating arm assembly 60.

Figure 43:
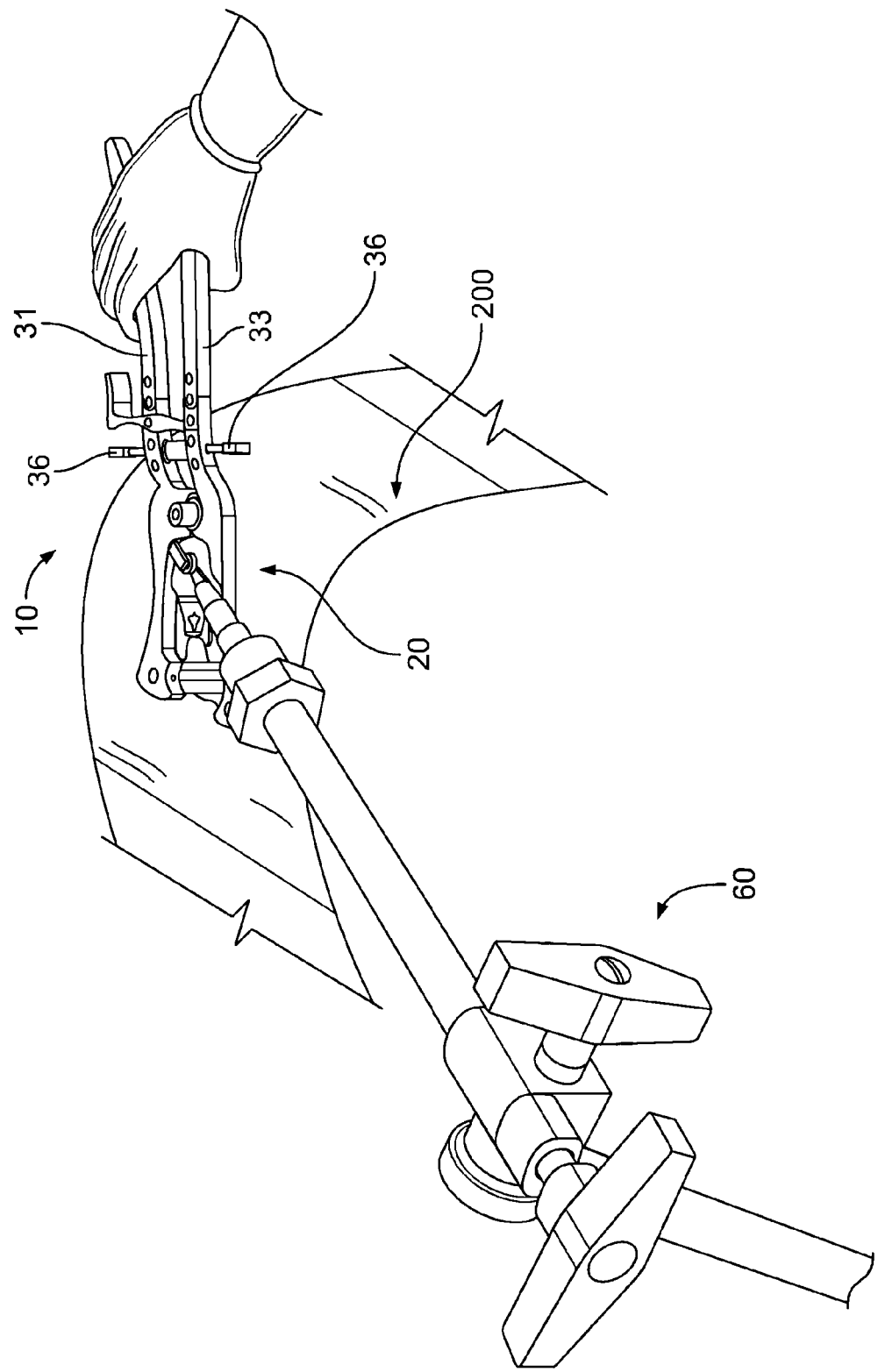
Figure 44:
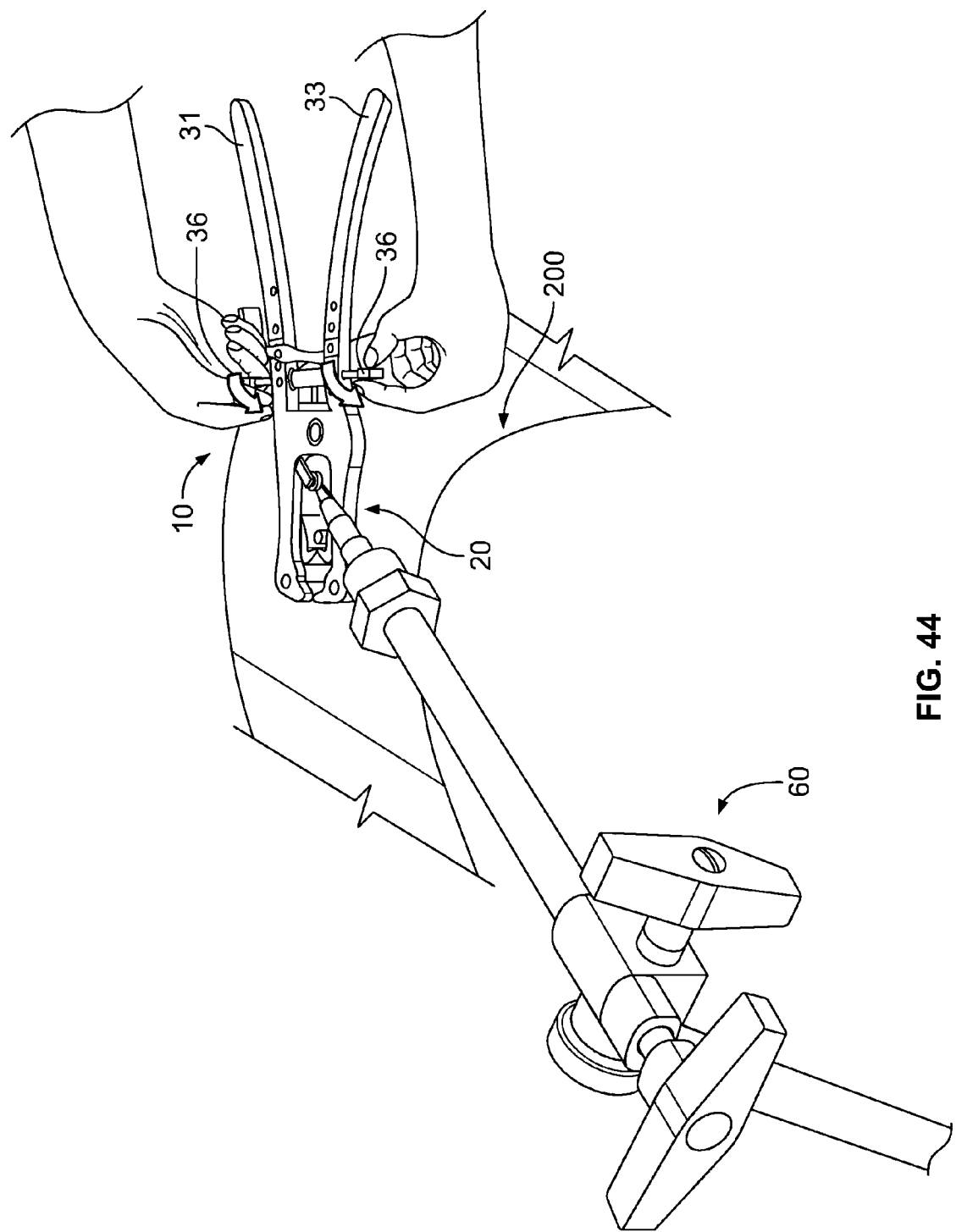

Referring now to FIGS. 43-44, handle extenders 31 and 33 may be squeeze to spread the blades 12, 16, 18 and knob members 36 may be turned to selectively adjust the posterior retractor blade 12 (previously described in connection with FIGS. 13-18). Such movement by the blades 12, 16, 18 retracts the distraction corridor so as to form an operative corridor 15.

Figure 45:
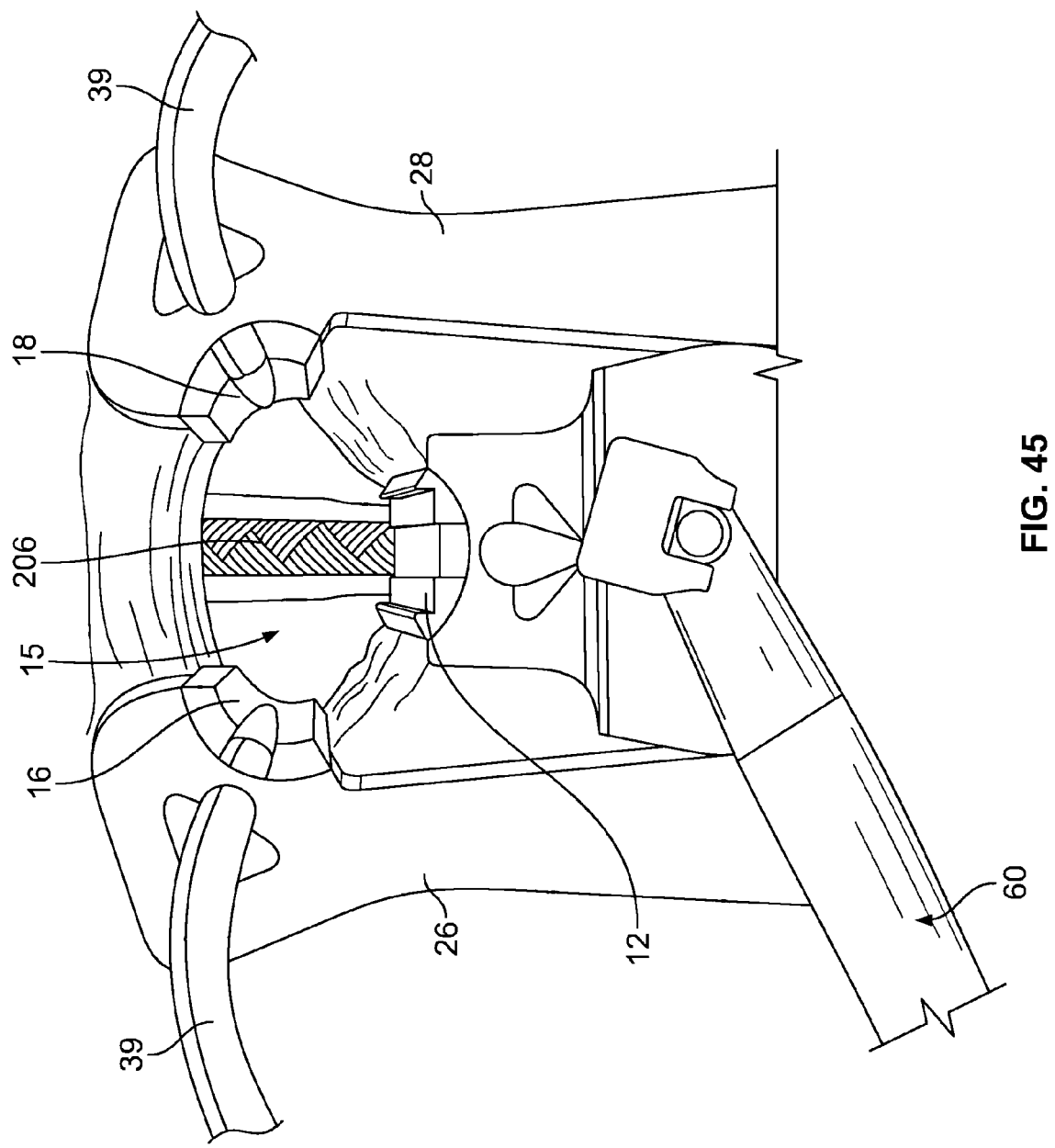

FIG. 45 shows a lateral view of the operative corridor 15 down to the targeted disc space 206 in the patient's spine. Light emitting devices 39 may be coupled to one or more of the retractor blades 12, 16, 18 to direct light down the operative corridor 15. In this embodiment, the light emitting devices 39 are coupled to a xenon arthroscopy light source. The surgeon may use direct visualization and/or a NeuroVision probe of the type disclosed in the NeuroVision PCT Applications to confirm that the operative corridor 15 is neurologically clear.

Referring to FIGS. 46-50, various instruments may be inserted through the operative corridor 15 to prepare the targeted disc space 206. In the presently preferred embodiment, the operative corridor 15 has a 15-20 mm annulotomy to provide ample space for the various instruments. In other embodiments, the operative corridor 15 may have other configurations, depending on the surgical task to be performed.

Figure 46:
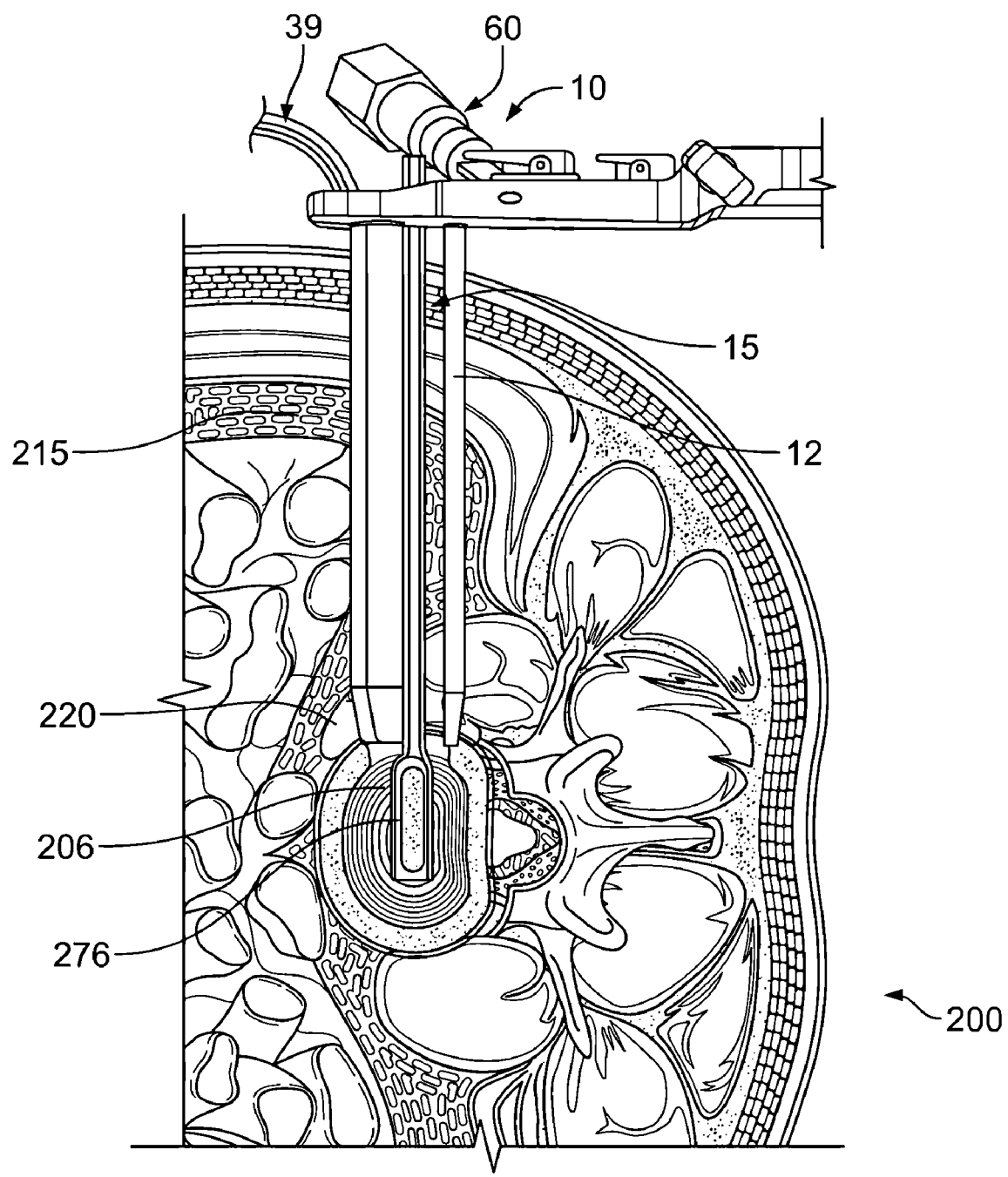
Figure 47:
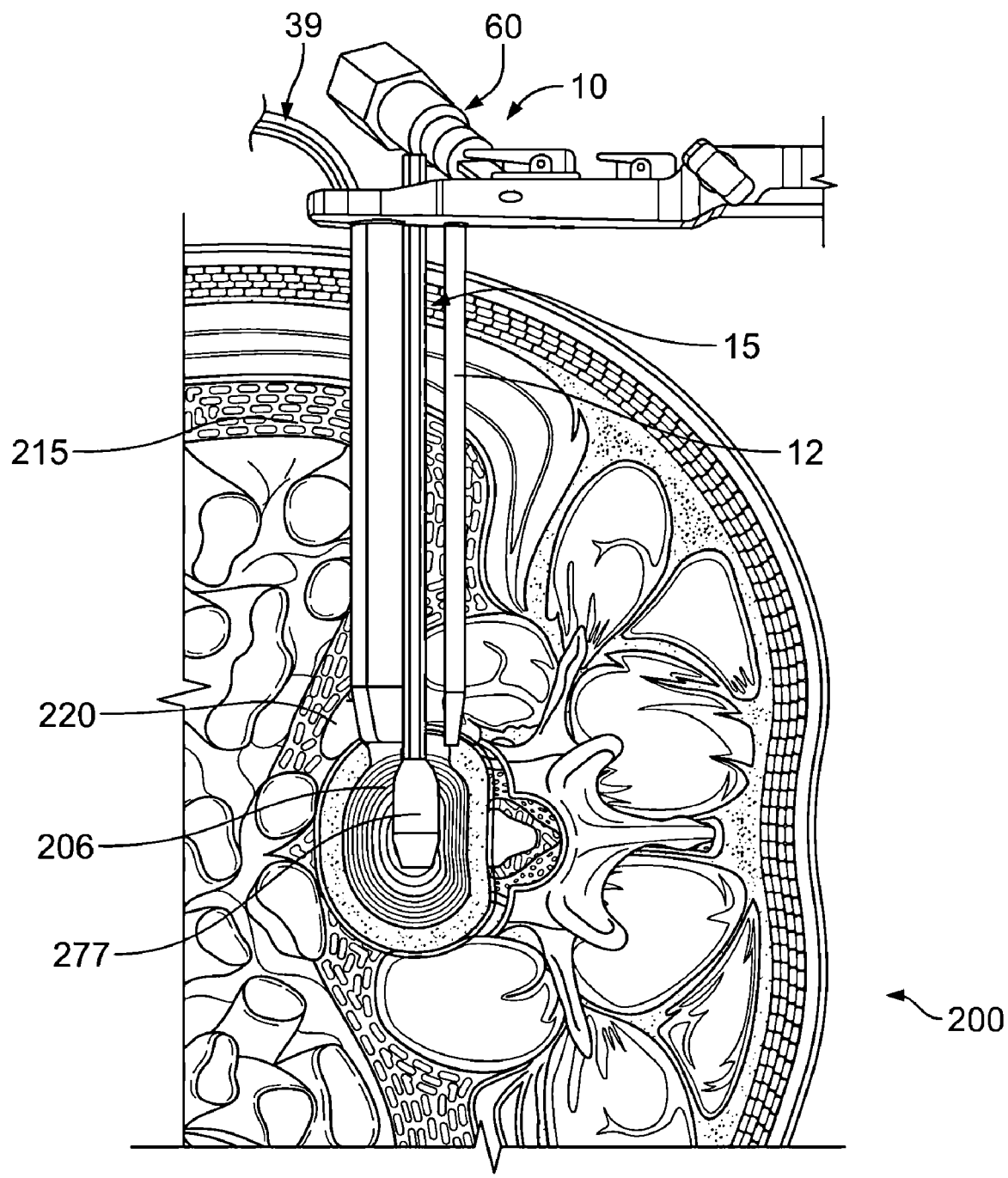
Figure 48:
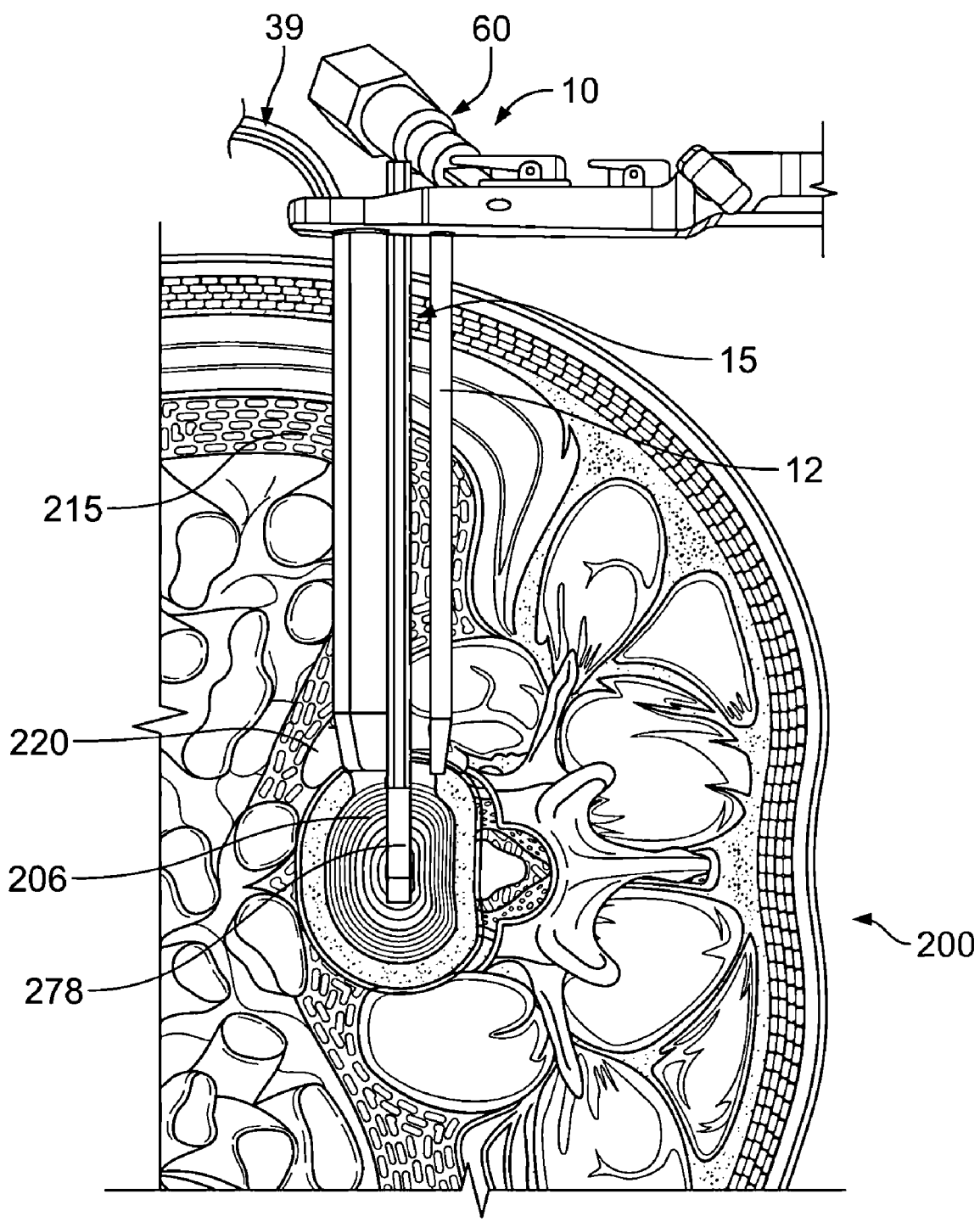

In this embodiment depicted in FIGS. 46-50, the disc space 206 is undergoing a discectomy and insertion of a spinal implant. As shown in FIG. 46, at least one preparation tool 276 such as a disc cutter, pituitary, scraper, curette, or the like is inserted through the operative corridor 15 to prepare the disc space 206. Referring more closely to FIG. 47, one or more sizers 277 are inserted to the disc space 206 to provide appropriate disc height restoration. As shown in FIG. 48, a broach 278 may be used in the disc space 206 to remove osteophytes and to facilitate implant insertion.

Figure 49:
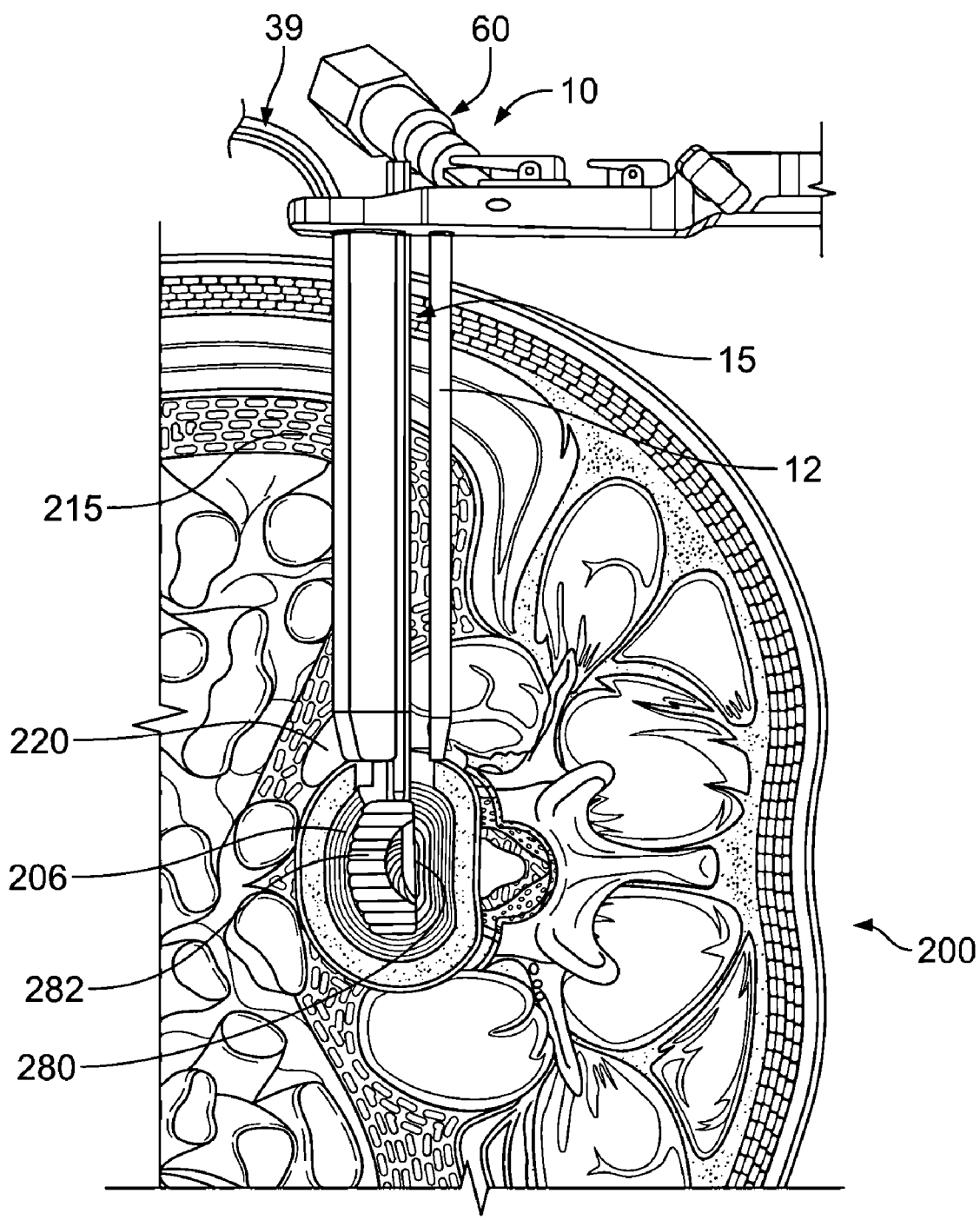
Figure 50:
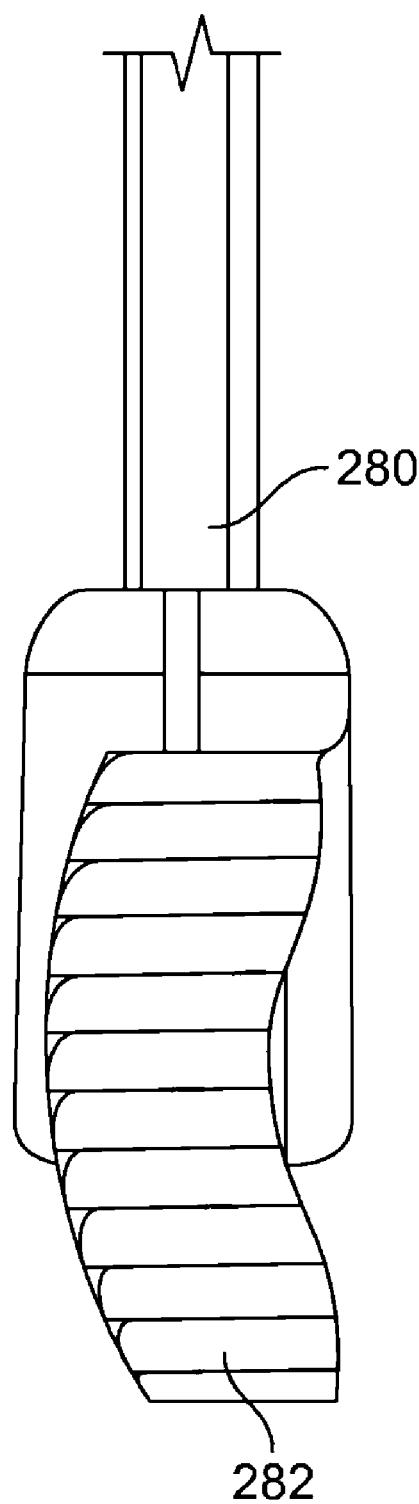

Referring now to FIGS. 49-50, an appropriately sized implant 282 is advanced into the disc space 206 with an inserter tool 280. The implant 282 is releasably secured to the inserter tool 280 such that the surgeon may release the implant when it is properly positioned in the disc space 206. The implant may comprise a material that facilitates bone fusion (such as allograft or autograft), and autograft or graft extenders may be used in the disc space 206 after the implant is inserted.

After the procedure on the targeted disc space 206 is complete, the access system 10 is carefully removed from the operative corridor 15. Direct visualization may be used to confirm the absence of significant bleeding in the disc space 206 or the psoas muscle 220. The skin around the operative corridor may be closed using a suturing method, such as a subcuticular suture.

Accordingly, certain methods of using the access system 10 can safely and effectively establish a minimally invasive operative corridor through the retroperitoneal space 215 and the psoas muscle 220 via a direct lateral, retroperitoneal approach to the spine. Such a method allows the surgeon to directly visualize the patient's anatomy without the cumbersome requirements associated with using endoscopes or operating coaxial through narrow, artificial tube. Moreover, when employing such a method to laterally approach the spine, the potential of damaging nerves while advancing dilators and other instruments through the psoas muscle 220 may be substantially reduced.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction of bone products (such as allograft or autograft) and/or devices having ceramic, metal and/or plastic construction (such as mesh) and/or compounds such as bone morphogenic protein), total disc replacement, etc. . . . ).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

What is claimed is:

1. A method included in providing surgical access to a spinal target site in a human patient through a substantially lateral, retroperitoneal approach, the method comprising:
  inserting at least a portion of a finger of a surgeon through a first, posteriolateral incision and into a retroperitoneal space;
  sweeping at least a portion of the finger in the retroperitoneal space;
  inserting a distal tip of a dilation member through a second, substantially lateral incision and into the retroperitoneal space;
  using at least a portion of the finger to guide the distal tip of the dilation member within the retroperitoneal space toward a psoas muscle; and
  advancing the distal tip of the dilation member in a substantially lateral direction through the psoas muscle toward a spinal target site while using a stimulation electrode on the dilation member to monitor for the presence of nerves in the vicinity of the dilation member.

2. The method of claim 1, wherein the dilation member is an initial dilator.

3. The method of claim 1, further comprising operating a control unit to electrically stimulate said stimulation electrode, sensing a response of a nerve depolarized by said stimulation, and determining a direction from the dilation member to the nerve based upon the sensed response.

4. The method of claim 1, further comprising creating a distraction corridor by advancing one or more secondary dilators over the dilation member to sequentially widen said distraction corridor.

5. The method of claim 4, wherein creating said distraction corridor comprises monitoring for the presence of nerves using at least one stimulation electrode on at least one of the secondary dilators.

6. The method of claim 5, wherein said monitoring for the presence of nerves that is part of said creating of said distraction corridor includes operating a control unit to electrically stimulate said at least one stimulation electrode on the at least one of the secondary dilators, sensing a response of a nerve depolarized by said stimulation, and determining a direction from said at least one of the secondary dilators to the nerve based upon the sensed response.

7. The method of claim 1, further comprising retracting a distraction corridor to produce a substantially lateral operative corridor to said spinal target site.

8. The method of claim 7, wherein retracting said distraction corridor comprises:
  simultaneously introducing a plurality of retractor blades into said distraction corridor; and
  opening said plurality of retractor blades to create an operative corridor to said spinal target site.

9. A method of accessing a spinal target site in a human patient, comprising:
  creating a distraction corridor to a spinal target site through a substantially lateral, retroperitoneal approach, comprising:
    inserting at least a portion of a finger of an operating surgeon through a first, posteriolateral incision and into a retroperitoneal space,
    sweeping at least a portion of the finger in the retroperitoneal space;
    inserting a distal end of a dilation member through a second, substantially lateral incision and into the retroperitoneal space, using at least a portion of the finger to guide the distal end of the dilation member within the retroperitoneal space, and
    advancing the dilation member in a substantially lateral direction toward the spinal target site; and
  retracting said distraction corridor to produce an operative corridor to said spinal target site.

10. The method of claim 9, wherein the dilation member is an initial dilator.

11. The method of claim 10, wherein the initial dilator includes at least a K-wire.

12. The method of claim 9, wherein creating said distraction corridor includes operating one or more secondary dilators to sequentially widen said distraction corridor.

13. The method of claim 9, wherein at least one of creating said distraction corridor and retracting said distraction corridor comprises monitoring for the presence of nerves using at least one stimulation electrode.

14. The method of claim 13, wherein monitoring for the presence of nerves includes operating a control unit to electrically stimulate said at least one stimulation electrode, sensing a response of a nerve depolarized by said stimulation, and determining a direction from at least one of the dilation member and a retractor to the nerve based upon the sensed response.

15. The method of claim 9, wherein retracting said distraction corridor comprises:
  simultaneously introducing a plurality of retractor blades into said distraction corridor; and
  opening said plurality of retractor blades to create an operative corridor to said surgical target site.

16. The method of claim 15, wherein the plurality of retractor blades are simultaneously introduced to the surgical target site while in a generally closed position.

17. The method of claim 15, wherein the plurality of retractor blades are opened by selectively moving said retractor blades to create a customized operative corridor to said surgical target site.

18. The method of claim 1, wherein the patient is positioned in a lateral decubitus position during the method.

19. The method of claim 1, further comprising using at least a portion of the finger to palpate a lateral aspect of the psoas muscle prior to inserting the distal tip of the dilation member.

20. The method of claim 1, wherein the step of sweeping at least a portion of the finger comprises sweeping the peritoneal cavity anteriorly.

21. The method claim 1, wherein the step of sweeping at least a portion of the finger comprises loosening fatty tissue in the retroperitoneal space.

22. The method claim 1, wherein the spinal target site comprises an intervertebral disc space in a lumbar spine.

23. The method of claim 1, further comprising inserting a plurality of sequential dilators over the dilation member in the substantially lateral direction through the psoas muscle.

24. The method of claim 9, wherein the patient is positioned in a lateral decubitus position during the method.

25. The method of claim 9, further comprising using at least a portion of the finger to palpate a lateral aspect of a psoas muscle prior to inserting the distal end of the dilation member.

26. The method of claim 9, wherein the step of sweeping at least a portion of the finger comprises sweeping the peritoneal cavity anteriorly.

27. The method claim 9, wherein the step of sweeping at least a portion of the finger comprises loosening fatty tissue in the retroperitoneal space.

28. The method claim 9, wherein the spinal target site comprises an intervertebral disc space in a lumbar spine.

29. The method of claim 9, wherein the step of creating the distraction corridor further comprises inserting a plurality of sequential dilators over the dilation member in the substantially lateral direction through the psoas muscle.

30. The method of claim 2, wherein the initial dilator includes at least a K-wire.

* * * * *